US009365527B2

(12) United States Patent
Chesworth et al.

(10) Patent No.: US 9,365,527 B2
(45) Date of Patent: Jun. 14, 2016

(54) ARGININE METHYLTRANSFERASE INHIBITORS AND USES THEREOF

(71) Applicant: Epizyme, Inc., Cambridge, MA (US)

(72) Inventors: Richard Chesworth, Concord, MA (US); Lorna Helen Mitchell, Cambridge, MA (US); Gideon Shapiro, Gainesville, FL (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 14/213,272

(22) Filed: Mar. 14, 2014

(65) Prior Publication Data

US 2014/0315961 A1    Oct. 23, 2014

Related U.S. Application Data

(60) Provisional application No. 61/781,059, filed on Mar. 14, 2013.

(51) Int. Cl.
| | |
|---|---|
| *C07D 233/64* | (2006.01) |
| *C07D 231/12* | (2006.01) |
| *C07D 285/10* | (2006.01) |
| *C07D 233/54* | (2006.01) |
| *C07D 405/12* | (2006.01) |
| *C07D 249/06* | (2006.01) |
| *C07D 263/32* | (2006.01) |
| *C07D 285/06* | (2006.01) |
| *C07D 261/08* | (2006.01) |

(52) U.S. Cl.
CPC ............ *C07D 285/10* (2013.01); *C07D 231/12* (2013.01); *C07D 233/54* (2013.01); *C07D 233/64* (2013.01); *C07D 249/06* (2013.01); *C07D 261/08* (2013.01); *C07D 263/32* (2013.01); *C07D 285/06* (2013.01); *C07D 405/12* (2013.01)

(58) Field of Classification Search
CPC ............................ C07D 233/64; C07D 231/12
See application file for complete search history.

(56) References Cited

U.S. PATENT DOCUMENTS

| | | | |
|---|---|---|---|
| 5,011,849 A | 4/1991 | Gassner et al. | |
| 5,204,482 A | 4/1993 | Gassner et al. | |
| 5,932,737 A | 8/1999 | Itoh et al. | |
| 6,566,376 B1 | 5/2003 | Baxter et al. | |
| 6,914,160 B1 | 7/2005 | Armour et al. | |
| 7,485,722 B2 | 2/2009 | Egle et al. | |
| 7,629,294 B2 | 12/2009 | Gebauer et al. | |
| 7,632,855 B2 | 12/2009 | Barrilalonso et al. | |
| 7,759,336 B2 | 7/2010 | Habashita et al. | |
| 8,063,071 B2 | 11/2011 | Kerns et al. | |
| 8,097,708 B2 | 1/2012 | Sugimoto et al. | |
| 8,133,904 B2 | 3/2012 | McElroy et al. | |
| 8,153,625 B2 | 4/2012 | Habashita et al. | |
| 8,338,437 B2 | 12/2012 | Wahhab et al. | |
| 8,952,026 B2 | 2/2015 | Mitchell et al. | |
| 9,023,883 B2 | 5/2015 | Kuntz et al. | |
| 9,045,455 B2 | 6/2015 | Mitchell et al. | |
| 9,120,757 B2 | 9/2015 | Chesworth et al. | |
| 9,133,189 B2 | 9/2015 | Chesworth et al. | |
| 2002/0090627 A1 | 7/2002 | Meyers | |
| 2005/0032794 A1 | 2/2005 | Padia et al. | |
| 2005/0187224 A1 | 8/2005 | Gebauer et al. | |
| 2006/0128724 A1 | 6/2006 | Cui et al. | |
| 2006/0235037 A1 | 10/2006 | Purandare et al. | |
| 2006/0239990 A1 | 10/2006 | Nabel et al. | |
| 2006/0264419 A1 | 11/2006 | Schiemann et al. | |
| 2007/0060589 A1 | 3/2007 | Purandare et al. | |
| 2008/0214615 A1 | 9/2008 | Muller et al. | |
| 2008/0214654 A1 | 9/2008 | Lampe et al. | |
| 2008/0280925 A1 | 11/2008 | Wahhab et al. | |
| 2008/0312298 A1 | 12/2008 | Foreman et al. | |
| 2009/0012031 A1 | 1/2009 | Chinnaiyan et al. | |
| 2009/0036435 A1 | 2/2009 | Curry et al. | |
| 2009/0143372 A1 | 6/2009 | Deng et al. | |
| 2009/0298910 A1 | 12/2009 | Griffey et al. | |
| 2009/0306201 A1 | 12/2009 | Reinberg et al. | |
| 2010/0151506 A1 | 6/2010 | Thompson et al. | |
| 2011/0021362 A1 | 1/2011 | Trojer et al. | |
| 2011/0065681 A1 | 3/2011 | Wei et al. | |

(Continued)

FOREIGN PATENT DOCUMENTS

| | | |
|---|---|---|
| DE | 10149370 A1 | 4/2003 |
| EP | 1571146 A1 | 9/2005 |

(Continued)

OTHER PUBLICATIONS

International Search Report and Written Opinion for International Application No. PCT/US2014/029009 mailed May 28, 2014.

(Continued)

*Primary Examiner* — Michael Barker
*Assistant Examiner* — Karen Cheng
(74) *Attorney, Agent, or Firm* — Wolf, Greenfield & Sacks, P.C.

(57) ABSTRACT

Described herein are compounds of Formula (I), pharmaceutically acceptable salts thereof, and pharmaceutical compositions thereof. Compounds of the present invention are useful for inhibiting arginine methyltransferase activity. Methods of using the compounds for treating arginine methyltransferase-mediated disorders are also described.

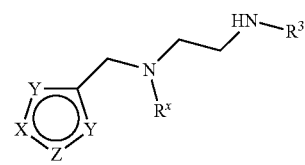

33 Claims, No Drawings

(56) References Cited

U.S. PATENT DOCUMENTS

| | | |
|---|---|---|
| 2011/0160293 A1 | 6/2011 | Nakamura et al. |
| 2011/0251216 A1 | 10/2011 | Chinnaiyan et al. |
| 2011/0269770 A1 | 11/2011 | Gross et al. |
| 2012/0071418 A1 | 3/2012 | Copeland et al. |
| 2012/0142625 A1 | 6/2012 | Olhava et al. |
| 2012/0156219 A1 | 6/2012 | Habashita et al. |
| 2012/0264734 A1 | 10/2012 | Kuntz et al. |
| 2013/0345268 A1 | 12/2013 | Ratner et al. |
| 2014/0288105 A1 | 9/2014 | Chesworth et al. |
| 2014/0288124 A1 | 9/2014 | Chesworth et al. |
| 2014/0288128 A1 | 9/2014 | Mitchell et al. |
| 2014/0288129 A1 | 9/2014 | Mitchell et al. |
| 2014/0288140 A1 | 9/2014 | Mitchell et al. |
| 2014/0288141 A1 | 9/2014 | Kuntz et al. |
| 2014/0315904 A1 | 10/2014 | Chesworth et al. |
| 2014/0323537 A1 | 10/2014 | Chesworth et al. |
| 2015/0284334 A1 | 10/2015 | Kuntz et al. |

FOREIGN PATENT DOCUMENTS

| | | |
|---|---|---|
| EP | 2 221 053 A1 | 8/2010 |
| EP | 2 226 315 A1 | 9/2010 |
| JP | 2009-179616 A | 8/2009 |
| WO | WO 96/16981 A2 | 6/1996 |
| WO | WO 03/031435 A1 | 4/2003 |
| WO | WO 2004/020414 A1 | 3/2004 |
| WO | WO 2004/052862 A1 | 6/2004 |
| WO | WO 2004/089931 A1 | 10/2004 |
| WO | WO 2004/096212 A1 | 11/2004 |
| WO | WO 2006/025832 A1 | 3/2006 |
| WO | WO 2006/033995 A2 | 3/2006 |
| WO | WO 2006/040136 A1 | 4/2006 |
| WO | WO 2006/069155 A2 | 6/2006 |
| WO | WO 2007/091393 A1 | 8/2007 |
| WO | WO 2008/001076 A1 | 1/2008 |
| WO | WO 2008/008286 A2 | 1/2008 |
| WO | WO 2008/104077 A1 | 9/2008 |
| WO | WO 2008/137834 A2 | 11/2008 |
| WO | WO 2009/033125 A1 | 3/2009 |
| WO | WO 2009/126537 A1 | 10/2009 |
| WO | WO 2010/034737 A1 | 4/2010 |
| WO | WO 2010/094009 A2 | 8/2010 |
| WO | WO 2010/094609 A1 | 8/2010 |
| WO | WO 2011/079236 A1 | 6/2011 |
| WO | WO 2011/082098 A1 | 7/2011 |
| WO | WO 2011/096210 A1 | 8/2011 |
| WO | WO 2011/096211 A1 | 8/2011 |
| WO | WO 2011/140324 A1 | 11/2011 |
| WO | WO 2012/005805 A1 | 1/2012 |
| WO | WO 2012/060760 A1 | 5/2012 |
| WO | WO 2012/068589 A2 | 5/2012 |
| WO | WO 2012/075080 A1 | 6/2012 |
| WO | WO 2012/075492 A2 | 6/2012 |
| WO | WO 2012/075500 A2 | 6/2012 |
| WO | WO 2012/082436 A2 | 6/2012 |
| WO | WO 2012/118812 A2 | 9/2012 |
| WO | WO 2012/142513 A1 | 10/2012 |
| WO | WO 2013/174947 A1 | 11/2013 |
| WO | WO 2014/144659 A1 | 9/2014 |
| WO | WO 2014/153090 A1 | 9/2014 |
| WO | WO 2014/153172 A1 | 9/2014 |
| WO | WO 2014/153208 A1 | 9/2014 |
| WO | WO 2014/153214 A1 | 9/2014 |
| WO | WO 2014/153226 A1 | 9/2014 |
| WO | WO 2014/153235 A2 | 9/2014 |
| WO | WO 2014/178954 A1 | 11/2014 |

OTHER PUBLICATIONS

International Search Report and Written Opinion for International Application No. PCT/US2014/029160 mailed May 28, 2014.
International Search Report and Written Opinion for International Application No. PCT/US2014/029583 mailed Jul. 29, 2014.
International Search Report and Written Opinion for International Application No. PCT/US2014/029605 mailed Jul. 23, 2014.
International Search Report and Written Opinion for International Application No. PCT/US2014/029665 mailed Jul. 23, 2014.
International Search Report and Written Opinion for International Application No. PCT/US2014/029710 mailed Jul. 15, 2014.
International Search Report and Written Opinion for International Application No. PCT/US2014/029062 mailed Sep. 17, 2014.
International Search Report and Written Opinion for International Application No. PCT/US2014/029750 mailed Oct. 2, 2014.
International Search Report and Written Opinion for International Application No. PCT/US2014/029408 mailed Jun. 17, 2014.
Al-Dhaheri et al., CARM1 is an important determinant of ERα-dependent breast cancer cell differentiation and proliferation in breast cancer cells. Cancer Res. Mar. 15, 2011;71(6):2118-28. doi: 10.1158/0008-5472.CAN-10-2426. Epub Jan. 31, 2011.
Blanchet et al., CD28 costimulatory signal induces protein arginine methylation in T cells. J Exp Med. Aug. 1, 2005;202(3):371-7.
Boger, Asymmetric dimethylarginine (ADMA): a novel risk marker in cardiovascular medicine and beyond. Ann Med. 2006;38(2):126-36.
Bratenko et al., Synthesis and antimicrobial activities of 1,3-bis(4-pyrazolylmethyl)-2-(4-nitrophenyl) imidazolidines and hexahydropyrimidines. Farmatsevtichnii Zhurnal. 2007;5:66-70.
CAS Registry Accession No. 1340581-60-3. Nov. 3, 2011.
CAS Registry Accession No. 1342545-59-8. Nov. 8, 2011.
CAS Registry File RN 1524901-21-0, STN Entry Date: Oct, 10, 2013.
CAS Registry File RN 1547978-57-3, STN Entry Date: Jul. 3, 2013.
CAS Registry File RN 1551294-59-7, STN Entry Date: Oct. 10, 2013.
CAS Registry File RN 1564967-49-2, STN Entry Date: Oct. 10, 2013.
CAS Registry File RN 1564977-15-6, STN Entry Date: Oct. 10, 2013.
CAS Registry File RN 1565645-75-1. Dated Mar. 10, 2014.
CAS Registry File RN 1566071-28-0, STN Entry Date: Oct. 10, 2013.
CAS Registry File RN 1566350-70-6, STN Entry Date: Oct. 10, 2013.
Chen et al., Expression of nitric oxide related enzymes in coronary heart disease. Basic Res Cardiol. Jul. 2006;101(4):346-53. Epub May 16, 2006.
Cheung et al., Protein arginine-methyltransferase-dependent oncogenesis. Nat Cell Biol. Oct. 2007;9(10):1208-15. Epub Sep. 23, 2007.
Choi et al., Protein arginine methyltransferase 1 regulates hepatic glucose production in a FoxO1-dependent manner. Hepatology. Oct. 2012;56(4):1546-56. doi: 10.1002/hep.25809.
Copeland, Protein methyltransferase inhibitors as personalized cancer therapeutics. Drug Discov Today Ther Strateg. 2012;9:e83-e90.
Covic et al., Arginine methyltransferase CARM1 is a promoter-specific regulator of NF-kappaB-dependent gene expression. EMBO J. Jan. 12, 2005;24(1):85-96. Epub Dec. 16, 2004.
Davies et al., Oculopharyngeal muscular dystrophy: potential therapies for an aggregate-associated disorder. Int J Biochem Cell Biol. 2006;38(9):1457-62. Epub Feb. 28, 2006.
Engelmann et al., The dark side of E2F1: in transit beyond apoptosis. Cancer Res. Feb. 1, 2012;72(3):571-5. doi: 10.1158/0008-5472.CAN-11-2575.
Forbes et al., COSMIC: mining complete cancer genomes in the Catalogue of Somatic Mutations in Cancer. Nucleic Acids Res. Jan. 2011;39(Database issue):D945-50. doi: 10.1093/nar/gkq929. Epub Oct. 15, 2010.
Frietze et al., CARM1 regulates estrogen-stimulated breast cancer growth through up-regulation of E2F1. Cancer Res. Jan. 1, 2008;68(1):301-6. doi: 10.1158/0008-5472.CAN-07-1983.
Fuchi et al., A library synthesis of pyrazoles by azomethine imine cycloaddition to the polymer-supported vinylsulfone. Chem Lett. 2005;34(3):438-9.
Hong et al., Aberrant expression of CARM1, a transcriptional coactivator of androgen receptor, in the development of prostate carcinoma and androgen-independent status. Cancer. Jul. 1, 2004;101(1):83-9.

(56) References Cited

OTHER PUBLICATIONS

Jacobi et al., Asymmetrical dimethylarginine in renal disease: limits of variation or variation limits? A systematic review. Am J Nephrol. 2008;28(2):224-37. Epub Oct. 24, 2007.
Kleinschmidt et al., Cell cycle regulation by the PRMT6 arginine methyltransferase through repression of cyclin-dependent kinase inhibitors. PLoS One. 2012;7(8):e41446. doi: 10.1371/journal.pone. 0041446. Epub Aug. 20, 2012.
Le Romancer et al., Methylation, a key step for nongenomic estrogen signaling in breast tumors. Steroids. Aug.-Sep. 2010;75(8-9):560-4. doi: 10.1016/j.steroids.2010.01.013. Epub Jan. 29, 2010.
Le Romancer et al., Regulation of estrogen rapid signaling through arginine methylation by PRMT1. Mol Cell. Jul. 25, 2008;31(2):212-21. doi: 10.1016/j.molcel.2008.05.025.
Leovac et al., Copper(II) complexes with reduced Schiff base: Synthesis, spectroscopic, thermal, X-ray, and cytotoxic studies of novel copper(II) complexes with an arylpyrazole ligand. Austrailian J Chem. 2007;60(8):615-20.
Majumder et al., Involvement of arginine methyltransferase CARM1 in androgen receptor function and prostate cancer cell viability. Prostate. Sep. 1, 2006;66(12):1292-301.
Michaud-Levesque et al., Thrombospondin-1 is a transcriptional repression target of PRMT6. J Biol Chem. Aug. 7, 2009;284(32):21338-46. doi: 10.1074/jbc.M109.005322. Epub Jun. 9, 2009.
Nagahata et al., Expression profiling to predict postoperative prognosis for estrogen receptor-negative breast cancers by analysis of 25,344 genes on a cDNA microarray. Cancer Sci. Mar. 2004;95(3):218-25.
Perreault et al., Regulation of the nuclear poly(A)-binding protein by arginine methylation in fission yeast. J Biol Chem. Mar. 9, 2007;282(10):7552-62. Epub Jan. 9, 2007.
Rappsilber et al., Detection of arginine dimethylated peptides by parallel precursor ion scanning mass spectrometry in positive ion mode. Anal Chem. Jul. 1, 2003;75(13):3107-14.
Richard et al., Arginine methylation regulates IL-2 gene expression: a role for protein arginine methyltransferase 5 (PRMT5). Biochem J. May 15, 2005;388(Pt 1):379-86.
Seligson et al., Global histone modification patterns predict risk of prostate cancer recurrence. Nature. Jun. 30, 2005;435(7046):1262-6.
Shia et al., PRMT1 interacts with AML1-ETO to promote its transcriptional activation and progenitor cell proliferative potential. Blood. May 24, 2012;119(21):4953-62. doi: 10.1182/blood2011-04-347476. Epub Apr. 12, 2012.
Singh et al., DAL-1/4.1B tumor suppressor interacts with protein arginine N-methyltransferase 3 (PRMT3) and inhibits its ability to methylate substrates in vitro and in vivo. Oncogene. Oct. 14, 2004;23(47):7761-71.
Sydow et al., Insulin resistance: potential role of the endogenous nitric oxide synthase inhibitor ADMA. Vasc Med. Jul. 2005;10 Suppl 1:S35-43.
Therrien et al., 1,2-Diamines as inhibitors of co-activator associated arginine methyltransferase 1 (CARM1). Bioorg Med Chem Lett. Dec. 1, 2009;19(23):6725-32. doi: 10.1016/j.bmcl.2009.09.110. Epub Oct. 2, 2009.
Vallance et al., Accumulation of an endogenous inhibitor of nitric oxide synthesis in chronic renal failure. Lancet. Mar. 7, 1992;339(8793):572-5.
Vallance et al., Endogenous dimethylarginine as an inhibitor of nitric oxide synthesis. J Cardiovasc Pharmacol. 1992;20 Suppl 12:S60-2.
Wang et al., CARM1/PRMT4 is necessary for the glycogen gene expression programme in skeletal muscle cells. Biochem J. Jun. 1, 2012;444(2):323-31. doi: 10.1042/BJ20112033.
Yoshimatsu et al., Dysregulation of PRMT1 and PRMT6, Type I arginine methyltransferases, is involved in various types of human cancers. Int J Cancer. Feb. 1, 2011;128(3):562-73. doi: 10.1002/ijc. 25366.
Zakrzewicz et al., From arginine methylation to ADMA: a novel mechanism with therapeutic potential in chronic lung diseases. BMC Pulm Med. Jan. 29, 2009;9:5. doi: 10.1186/1471-2466-9-5.
Invitation to Pay Additional Fees, and Where Applicable, Protest Fee for International Application No. PCT/US2015/050750 mailed Nov. 19, 2015.
International Search Report and Written Opinion for International Application No. PCT/US2015/050675 mailed Dec. 17, 2015.
International Search Report and Written Opinion for International Application No. PCT/US2015/050659 mailed Dec. 21, 2015.
PUBCHEM Submission; NIH/NCBI, Substance Identifier 107215563. Akos Consulting & Solutions. Feb. 22, 2011. 6 pages.
PUBCHEM Submission; NIH/NCBI, Substance Identifier 151630580. Akos Consulting & Solutions. Oct. 24, 2012. 10 pages.
Wan et al., Benzo[d]imidazole inhibitors of Coactivator Associated Arginine Methyltransferase 1 (CARM1)—Hit to Lead studies. Bioorg Med Chem Lett. Sep. 1, 2009;19(17):5063-6. doi: 10.1016/j.bmcl.2009.07.040. Epub Jul. 10, 2009.

SEQUENCE LISTING

```
<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 1

Xaa Arg Leu Ala Arg Arg Gly Gly Val Lys Arg Ile Ser Gly Leu Ile
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 2

Asp Tyr Lys Asp Asp Asp Asp Lys
1               5

<210> SEQ ID NO 3
<211> LENGTH: 230
<212> TYPE: PRT
<213> ORGANISM: Artificial Sequence
<220> FEATURE:
<223> OTHER INFORMATION: Synthetic Polypeptide

<400> SEQUENCE: 3
```

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Glu Asn Leu Tyr
    210                 215                 220

Phe Gln Gly Gly Asn Ser
225                 230

<210> SEQ ID NO 4
<211> LENGTH: 609
<212> TYPE: PRT
<213> ORGANISM: Artificial Sequence
<220> FEATURE:
<223> OTHER INFORMATION: Synthetic Polypeptide

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

```
Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Glu Asn Leu Tyr
            210                 215                 220

Phe Gln Gly Gly Asn Ser Asp Tyr Lys Asp Asp Asp Lys Met Ala
225                 230                 235                 240

Ala Ala Glu Ala Ala Asn Cys Ile Met Glu Asn Phe Val Ala Thr Leu
                245                 250                 255

Ala Asn Gly Met Ser Leu Gln Pro Pro Leu Glu Glu Val Ser Cys Gly
                260                 265                 270

Gln Ala Glu Ser Ser Glu Lys Pro Asn Ala Glu Asp Met Thr Ser Lys
            275                 280                 285

Asp Tyr Tyr Phe Asp Ser Tyr Ala His Phe Gly Ile His Glu Glu Met
            290                 295                 300

Leu Lys Asp Glu Val Arg Thr Leu Thr Tyr Arg Asn Ser Met Phe His
305                 310                 315                 320

Asn Arg His Leu Phe Lys Asp Lys Val Val Leu Asp Val Gly Ser Gly
                325                 330                 335

Thr Gly Ile Leu Cys Met Phe Ala Ala Lys Ala Gly Ala Arg Lys Val
                340                 345                 350

Ile Gly Ile Glu Cys Ser Ser Ile Ser Asp Tyr Ala Val Lys Ile Val
            355                 360                 365

Lys Ala Asn Lys Leu Asp His Val Val Thr Ile Ile Lys Gly Lys Val
            370                 375                 380

Glu Glu Val Glu Leu Pro Val Glu Lys Val Asp Ile Ile Ser Glu
385                 390                 395                 400

Trp Met Gly Tyr Cys Leu Phe Tyr Glu Ser Met Leu Asn Thr Val Leu
                405                 410                 415

Tyr Ala Arg Asp Lys Trp Leu Ala Pro Asp Gly Leu Ile Phe Pro Asp
                420                 425                 430

Arg Ala Thr Leu Tyr Val Thr Ala Ile Glu Asp Arg Gln Tyr Lys Asp
            435                 440                 445

Tyr Lys Ile His Trp Trp Glu Asn Val Tyr Gly Phe Asp Met Ser Cys
            450                 455                 460

Ile Lys Asp Val Ala Ile Lys Glu Pro Leu Val Asp Val Val Asp Pro
465                 470                 475                 480

Lys Gln Leu Val Thr Asn Ala Cys Leu Ile Lys Glu Val Asp Ile Tyr
                485                 490                 495

Thr Val Lys Val Glu Asp Leu Thr Phe Thr Ser Pro Phe Cys Leu Gln
                500                 505                 510

Val Lys Arg Asn Asp Tyr Val His Ala Leu Val Ala Tyr Phe Asn Ile
            515                 520                 525

Glu Phe Thr Arg Cys His Lys Arg Thr Gly Phe Ser Thr Ser Pro Glu
530                 535                 540
```

```
Ser Pro Tyr Thr His Trp Lys Gln Thr Val Phe Tyr Met Glu Asp Tyr
545                 550                 555                 560

Leu Thr Val Lys Thr Gly Glu Glu Ile Phe Gly Thr Ile Gly Met Arg
                565                 570                 575

Pro Asn Ala Lys Asn Asn Arg Asp Leu Asp Phe Thr Ile Asp Leu Asp
                580                 585                 590

Phe Lys Gly Gln Leu Cys Glu Leu Ser Cys Ser Thr Asp Tyr Arg Met
                595                 600                 605

Arg

<210> SEQ ID NO 5
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 5

Xaa Arg Leu Ala Arg Arg Gly Gly Val Lys Arg Ile Ser Gly Leu Ile
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 6

Met Asp Tyr Lys Asp Asp Asp Asp Lys
1               5

<210> SEQ ID NO 7
<211> LENGTH: 389
<212> TYPE: PRT
<213> ORGANISM: Artificial Sequence
<220> FEATURE:
<223> OTHER INFORMATION: Synthetic Polypeptide

<400> SEQUENCE: 7

Met Asp Tyr Lys Asp Asp Asp Asp Lys Ser Gln Pro Lys Lys Arg Lys
1               5                   10                  15

Leu Glu Ser Gly Gly Gly Gly Glu Gly Gly Gly Thr Glu Glu Glu
                20                  25                  30

Asp Gly Ala Glu Arg Glu Ala Ala Leu Glu Arg Pro Arg Arg Thr Lys
            35                  40                  45

Arg Glu Arg Asp Gln Leu Tyr Tyr Glu Cys Tyr Ser Asp Val Ser Val
        50                  55                  60

His Glu Glu Met Ile Ala Asp Arg Val Arg Thr Asp Ala Tyr Arg Leu
65                  70                  75                  80

Gly Ile Leu Arg Asn Trp Ala Ala Leu Arg Gly Lys Thr Val Leu Asp
                85                  90                  95

Val Gly Ala Gly Thr Gly Ile Leu Ser Ile Phe Cys Ala Gln Ala Gly
                100                 105                 110

Ala Arg Arg Val Tyr Ala Val Glu Ala Ser Ala Ile Trp Gln Gln Ala
            115                 120                 125

Arg Glu Val Val Arg Phe Asn Gly Leu Glu Asp Arg Val His Val Leu
```

```
                130                 135                 140
Pro Gly Pro Val Glu Thr Val Glu Leu Pro Glu Gln Val Asp Ala Ile
145                 150                 155                 160

Val Ser Glu Trp Met Gly Tyr Gly Leu Leu His Glu Ser Met Leu Ser
                165                 170                 175

Ser Val Leu His Ala Arg Thr Lys Trp Leu Lys Glu Gly Leu Leu
            180                 185                 190

Leu Pro Ala Ser Ala Glu Leu Phe Ile Ala Pro Ile Ser Asp Gln Met
            195                 200                 205

Leu Glu Trp Arg Leu Gly Phe Trp Ser Gln Val Lys Gln His Tyr Gly
    210                 215                 220

Val Asp Met Ser Cys Leu Glu Gly Phe Ala Thr Arg Cys Leu Met Gly
225                 230                 235                 240

His Ser Glu Ile Val Val Gln Gly Leu Ser Gly Glu Asp Val Leu Ala
                245                 250                 255

Arg Pro Gln Arg Phe Ala Gln Leu Glu Leu Ser Arg Ala Gly Leu Glu
            260                 265                 270

Gln Glu Leu Glu Ala Gly Val Gly Gly Arg Phe Arg Cys Ser Cys Tyr
        275                 280                 285

Gly Ser Ala Pro Met His Gly Phe Ala Ile Trp Phe Gln Val Thr Phe
    290                 295                 300

Pro Gly Gly Glu Ser Glu Lys Pro Leu Val Leu Ser Thr Ser Pro Phe
305                 310                 315                 320

His Pro Ala Thr His Trp Lys Gln Ala Leu Leu Tyr Leu Asn Glu Pro
                325                 330                 335

Val Gln Val Glu Gln Asp Thr Asp Val Ser Gly Glu Ile Thr Leu Leu
            340                 345                 350

Pro Ser Arg Asp Asn Pro Arg Arg Leu Arg Val Leu Arg Tyr Lys
        355                 360                 365

Val Gly Asp Gln Glu Glu Lys Thr Lys Asp Phe Ala Met Glu Asp His
    370                 375                 380

His His His His His
385

<210> SEQ ID NO 8
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 8

Xaa Lys Pro Ala Ile Arg Arg Leu Ala Arg Arg Gly Gly Val Lys Arg
1               5                   10                  15

<210> SEQ ID NO 9
<211> LENGTH: 229
<212> TYPE: PRT
<213> ORGANISM: Artificial Sequence
<220> FEATURE:
<223> OTHER INFORMATION: Synthetic Polypeptide

<400> SEQUENCE: 9

Met Ser Pro Ile Leu Gly Tyr Trp Lys Ile Lys Gly Leu Val Gln Pro
1               5                   10                  15
```

-continued

Thr Arg Leu Leu Leu Glu Tyr Leu Glu Glu Lys Tyr Glu Glu His Leu
        20                  25                  30

Tyr Glu Arg Asp Glu Gly Asp Lys Trp Arg Asn Lys Lys Phe Glu Leu
    35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
            85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe
225

<210> SEQ ID NO 10
<211> LENGTH: 623
<212> TYPE: PRT
<213> ORGANISM: Artificial Sequence
<220> FEATURE:
<223> OTHER INFORMATION: Synthetic Polypeptide

<400> SEQUENCE: 10

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

-continued

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
210                 215                 220

Gly Ser Pro Glu Phe Met Gly Met Lys His Ser Ser Arg Cys Leu Leu
225                 230                 235                 240

Leu Arg Arg Lys Met Ala Glu Asn Ala Ala Glu Ser Thr Glu Val Asn
                245                 250                 255

Ser Pro Pro Ser Gln Pro Pro Gln Pro Val Val Pro Ala Lys Pro Val
            260                 265                 270

Gln Cys Val His His Val Ser Thr Gln Pro Ser Cys Pro Gly Arg Gly
        275                 280                 285

Lys Met Ser Lys Leu Leu Asn Pro Glu Glu Met Thr Ser Arg Asp Tyr
290                 295                 300

Tyr Phe Asp Ser Tyr Ala His Phe Gly Ile His Glu Glu Met Leu Lys
305                 310                 315                 320

Asp Glu Val Arg Thr Leu Thr Tyr Arg Asn Ser Met Tyr His Asn Lys
                325                 330                 335

His Val Phe Lys Asp Lys Val Val Leu Asp Val Gly Ser Gly Thr Gly
            340                 345                 350

Ile Leu Ser Met Phe Ala Ala Lys Ala Gly Ala Lys Lys Val Phe Gly
        355                 360                 365

Ile Glu Cys Ser Ser Ile Ser Asp Tyr Ser Glu Lys Ile Ile Lys Ala
        370                 375                 380

Asn His Leu Asp Asn Ile Ile Thr Ile Phe Lys Gly Lys Val Glu Glu
385                 390                 395                 400

Val Glu Leu Pro Val Glu Lys Val Asp Ile Ile Ser Glu Trp Met
                405                 410                 415

Gly Tyr Cys Leu Phe Tyr Glu Ser Met Leu Asn Thr Val Ile Phe Ala
            420                 425                 430

Arg Asp Lys Trp Leu Lys Pro Gly Gly Leu Met Phe Pro Asp Arg Ala
        435                 440                 445

Ala Leu Tyr Val Val Ala Ile Glu Asp Arg Gln Tyr Lys Asp Phe Lys
        450                 455                 460

Ile His Trp Trp Glu Asn Val Tyr Gly Phe Asp Met Thr Cys Ile Arg
465                 470                 475                 480

Asp Val Ala Met Lys Glu Pro Leu Val Asp Ile Val Asp Pro Lys Gln
                485                 490                 495

Val Val Thr Asn Ala Cys Leu Ile Lys Glu Val Asp Ile Tyr Thr Val
            500                 505                 510

Lys Thr Glu Glu Leu Ser Phe Thr Ser Ala Phe Cys Leu Gln Ile Gln
        515                 520                 525

Arg Asn Asp Tyr Val His Ala Leu Val Thr Tyr Phe Asn Ile Glu Phe
        530                 535                 540

Thr Lys Cys His Lys Lys Met Gly Phe Ser Thr Ala Pro Asp Ala Pro
545                 550                 555                 560
```

```
Tyr Thr His Trp Lys Gln Thr Val Phe Tyr Leu Glu Asp Tyr Leu Thr
                565                 570                 575

Val Arg Arg Gly Glu Glu Ile Tyr Gly Thr Ile Ser Met Lys Pro Asn
            580                 585                 590

Ala Lys Asn Val Arg Asp Leu Asp Phe Thr Val Asp Leu Asp Phe Lys
        595                 600                 605

Gly Gln Leu Cys Glu Thr Ser Val Ser Asn Asp Tyr Lys Met Arg
    610                 615                 620

<210> SEQ ID NO 11
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 11

Xaa Gly Gly Arg Gly Gly Phe Gly Gly Arg Gly Gly Phe Gly Gly Arg
1               5                   10                  15

Gly Gly Phe Gly
            20

<210> SEQ ID NO 12
<211> LENGTH: 226
<212> TYPE: PRT
<213> ORGANISM: Artificial Sequence
<220> FEATURE:
<223> OTHER INFORMATION: Synthetic Polypeptide

<400> SEQUENCE: 12

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
```

```
                    195                 200                 205
Thr Phe Gly Gly Gly Asp His Pro Pro Lys Ser Asp Leu Val Pro Arg
    210                 215                 220
Gly Ser
225

<210> SEQ ID NO 13
<211> LENGTH: 756
<212> TYPE: PRT
<213> ORGANISM: Artificial Sequence
<220> FEATURE:
<223> OTHER INFORMATION: Synthetic Polypeptide

<400> SEQUENCE: 13

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Cys Ser Leu Ala Ser Gly Ala Thr Gly Gly Arg Gly Ala Val
225                 230                 235                 240

Glu Asn Glu Glu Asp Leu Pro Glu Leu Ser Asp Ser Gly Asp Glu Ala
                245                 250                 255

Ala Trp Glu Asp Glu Asp Ala Asp Leu Pro His Gly Lys Gln Gln
            260                 265                 270

Thr Pro Cys Leu Phe Cys Asn Arg Leu Phe Thr Ser Ala Glu Glu Thr
        275                 280                 285

Phe Ser His Cys Lys Ser Glu His Gln Phe Asn Ile Asp Ser Met Val
    290                 295                 300

His Lys His Gly Leu Glu Phe Tyr Gly Tyr Ile Lys Leu Ile Asn Phe
305                 310                 315                 320

Ile Arg Leu Lys Asn Pro Thr Val Glu Tyr Met Asn Ser Ile Tyr Asn
```

-continued

```
              325                 330                 335
Pro Val Pro Trp Glu Lys Glu Tyr Leu Lys Pro Val Leu Glu Asp
            340                 345                 350
Asp Leu Leu Gln Phe Asp Val Glu Asp Leu Tyr Glu Pro Val Ser
            355                 360                 365
Val Pro Phe Ser Tyr Pro Asn Gly Leu Ser Glu Asn Thr Ser Val Val
370                 375                 380
Glu Lys Leu Lys His Met Glu Ala Arg Ala Leu Ser Ala Glu Ala Ala
385                 390                 395                 400
Leu Ala Arg Ala Arg Glu Asp Leu Gln Lys Met Lys Gln Phe Ala Gln
            405                 410                 415
Asp Phe Val Met His Thr Asp Val Arg Thr Cys Ser Ser Thr Ser
            420                 425                 430
Val Ile Ala Asp Leu Gln Glu Asp Glu Asp Gly Val Tyr Phe Ser Ser
            435                 440                 445
Tyr Gly His Tyr Gly Ile His Glu Glu Met Leu Lys Asp Lys Ile Arg
450                 455                 460
Thr Glu Ser Tyr Arg Asp Phe Ile Tyr Gln Asn Pro His Ile Phe Lys
465                 470                 475                 480
Asp Lys Val Val Leu Asp Val Gly Cys Gly Thr Gly Ile Leu Ser Met
            485                 490                 495
Phe Ala Ala Lys Ala Gly Ala Lys Lys Val Leu Gly Val Asp Gln Ser
            500                 505                 510
Glu Ile Leu Tyr Gln Ala Met Asp Ile Ile Arg Leu Asn Lys Leu Glu
            515                 520                 525
Asp Thr Ile Thr Leu Ile Lys Gly Lys Ile Glu Glu Val His Leu Pro
530                 535                 540
Val Glu Lys Val Asp Val Ile Ile Ser Glu Trp Met Gly Tyr Phe Leu
545                 550                 555                 560
Leu Phe Glu Ser Met Leu Asp Ser Val Leu Tyr Ala Lys Asn Lys Tyr
            565                 570                 575
Leu Ala Lys Gly Gly Ser Val Tyr Pro Asp Ile Cys Thr Ile Ser Leu
            580                 585                 590
Val Ala Val Ser Asp Val Asn Lys His Ala Asp Arg Ile Ala Phe Trp
            595                 600                 605
Asp Asp Val Tyr Gly Phe Lys Met Ser Cys Met Lys Lys Ala Val Ile
610                 615                 620
Pro Glu Ala Val Val Glu Val Leu Asp Pro Lys Thr Leu Ile Ser Glu
625                 630                 635                 640
Pro Cys Gly Ile Lys His Ile Asp Cys His Thr Thr Ser Ile Ser Asp
            645                 650                 655
Leu Glu Phe Ser Ser Asp Phe Thr Leu Lys Ile Thr Arg Thr Ser Met
            660                 665                 670
Cys Thr Ala Ile Ala Gly Tyr Phe Asp Ile Tyr Phe Glu Lys Asn Cys
            675                 680                 685
His Asn Arg Val Val Phe Ser Thr Gly Pro Gln Ser Thr Lys Thr His
690                 695                 700
Trp Lys Gln Thr Val Phe Leu Leu Glu Lys Pro Phe Ser Val Lys Ala
705                 710                 715                 720
Gly Glu Ala Leu Lys Gly Lys Val Thr Val His Lys Asn Lys Lys Asp
            725                 730                 735
Pro Arg Ser Leu Thr Val Thr Leu Thr Leu Asn Asn Ser Thr Gln Thr
            740                 745                 750
```

```
Tyr Gly Leu Gln
        755

<210> SEQ ID NO 14
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 14

Xaa Pro Arg Lys Gln Leu Ala Thr Lys Ala Ala Arg Lys Ser Ala Pro
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 15

Glu Gly His His His His His His
1               5

<210> SEQ ID NO 16
<211> LENGTH: 601
<212> TYPE: PRT
<213> ORGANISM: Artificial Sequence
<220> FEATURE:
<223> OTHER INFORMATION: Synthetic Polypeptide

<400> SEQUENCE: 16

Met Asp Tyr Lys Asp Asp Asp Lys Ala Ala Ala Ala Ala Ala Ala Val
1               5                   10                  15

Gly Pro Gly Ala Gly Gly Ala Gly Ser Ala Val Pro Gly Gly Ala Gly
                20                  25                  30

Pro Cys Ala Thr Val Ser Val Phe Pro Gly Ala Arg Leu Leu Thr Ile
            35                  40                  45

Gly Asp Ala Asn Gly Glu Ile Gln Arg His Ala Glu Gln Gln Ala Leu
        50                  55                  60

Arg Leu Glu Val Arg Ala Gly Pro Asp Ser Ala Gly Ile Ala Leu Tyr
65                  70                  75                  80

Ser His Glu Asp Val Cys Val Phe Lys Cys Ser Val Ser Arg Glu Thr
                85                  90                  95

Glu Cys Ser Arg Val Gly Lys Gln Ser Phe Ile Ile Thr Leu Gly Cys
            100                 105                 110

Asn Ser Val Leu Ile Gln Phe Ala Thr Pro Asn Asp Phe Cys Ser Phe
        115                 120                 125

Tyr Asn Ile Leu Lys Thr Cys Arg Gly His Thr Leu Glu Arg Ser Val
    130                 135                 140

Phe Ser Glu Arg Thr Glu Glu Ser Ser Ala Val Gln Tyr Phe Gln Phe
145                 150                 155                 160

Tyr Gly Tyr Leu Ser Gln Gln Gln Asn Met Met Gln Asp Tyr Val Arg
                165                 170                 175

Thr Gly Thr Tyr Gln Arg Ala Ile Leu Gln Asn His Thr Asp Phe Lys
            180                 185                 190
```

```
Asp Lys Ile Val Leu Asp Val Gly Cys Gly Ser Gly Ile Leu Ser Phe
        195                 200                 205

Phe Ala Ala Gln Ala Gly Ala Arg Lys Ile Tyr Ala Val Glu Ala Ser
    210                 215                 220

Thr Met Ala Gln His Ala Glu Val Leu Val Lys Ser Asn Asn Leu Thr
225                 230                 235                 240

Asp Arg Ile Val Val Ile Pro Gly Lys Val Glu Val Ser Leu Pro
                245                 250                 255

Glu Gln Val Asp Ile Ile Ile Ser Glu Pro Met Gly Tyr Met Leu Phe
                260                 265                 270

Asn Glu Arg Met Leu Glu Ser Tyr Leu His Ala Lys Lys Tyr Leu Lys
            275                 280                 285

Pro Ser Gly Asn Met Phe Pro Thr Ile Gly Asp Val His Leu Ala Pro
        290                 295                 300

Phe Thr Asp Glu Gln Leu Tyr Met Glu Gln Phe Thr Lys Ala Asn Phe
305                 310                 315                 320

Trp Tyr Gln Pro Ser Phe His Gly Val Asp Leu Ser Ala Leu Arg Gly
                325                 330                 335

Ala Ala Val Asp Glu Tyr Phe Arg Gln Pro Val Val Asp Thr Phe Asp
            340                 345                 350

Ile Arg Ile Leu Met Ala Lys Ser Val Lys Tyr Thr Val Asn Phe Leu
            355                 360                 365

Glu Ala Lys Glu Gly Asp Leu His Arg Ile Glu Ile Pro Phe Lys Phe
        370                 375                 380

His Met Leu His Ser Gly Leu Val His Gly Leu Ala Phe Trp Phe Asp
385                 390                 395                 400

Val Ala Phe Ile Gly Ser Ile Met Thr Val Trp Leu Ser Thr Ala Pro
                405                 410                 415

Thr Glu Pro Leu Thr His Trp Tyr Gln Val Arg Cys Leu Phe Gln Ser
            420                 425                 430

Pro Leu Phe Ala Lys Ala Gly Asp Thr Leu Ser Gly Thr Cys Leu Leu
        435                 440                 445

Ile Ala Asn Lys Arg Gln Ser Tyr Asp Ile Ser Ile Val Ala Gln Val
        450                 455                 460

Asp Gln Thr Gly Ser Lys Ser Ser Asn Leu Leu Asp Leu Lys Asn Pro
465                 470                 475                 480

Phe Phe Arg Tyr Thr Gly Thr Thr Pro Ser Pro Pro Gly Ser His
                485                 490                 495

Tyr Thr Ser Pro Ser Glu Asn Met Trp Asn Thr Gly Ser Thr Tyr Asn
                500                 505                 510

Leu Ser Ser Gly Met Ala Val Ala Gly Met Pro Thr Ala Tyr Asp Leu
            515                 520                 525

Ser Ser Val Ile Ala Ser Gly Ser Val Gly His Asn Asn Leu Ile
        530                 535                 540

Pro Leu Gly Ser Ser Gly Ala Gln Gly Ser Gly Gly Ser Thr Ser
545                 550                 555                 560

Ala His Tyr Ala Val Asn Ser Gln Phe Thr Met Gly Gly Pro Ala Ile
                565                 570                 575
```

```
Ser Met Ala Ser Pro Met Ser Ile Pro Thr Asn Thr Met His Tyr Gly
            580                 585                 590
Ser Glu Gly His His His His His His
        595             600

<210> SEQ ID NO 17
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 17

His His His His His His
1               5
```

ARGININE METHYLTRANSFERASE INHIBITORS AND USES THEREOF

RELATED APPLICATIONS

The present application claims the benefit of and priority to U.S. Provisional Patent Application Ser. No. 61/781,059, filed Mar. 14, 2013, the entire contents of which is incorporated herein by reference.

BACKGROUND OF THE INVENTION

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., arginine methyltransferases), many of which are associated with specific genetic alterations that can cause human disease.

Disease-associated chromatin-modifying enzymes (e.g., arginine methyltransferases) play a role in diseases such as proliferative disorders, autoimmune disorders, muscular disorders, vascular disorders, metabolic disorders, and neurological disorders. Thus, there is a need for the development of small molecules that are capable of inhibiting the activity of arginine methyltransferases.

DETAILED DESCRIPTION OF CERTAIN EMBODIMENTS

Arginine methyltransferases are attractive targets for modulation given their role in the regulation of diverse biological processes. It has now been found that compounds described herein, and pharmaceutically acceptable salts and compositions thereof, are effective as inhibitors of arginine methyltransferases. Such compounds have the general Formula (I):

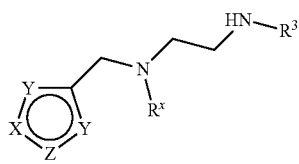

or a pharmaceutically acceptable salt thereof, wherein X, Y, Z, V, $R^3$, and $R^x$ are as defined herein.

In some embodiments, pharmaceutical compositions are provided which comprise a compound described herein (e.g., a compound of Formula (I)), or a pharmaceutically acceptable salt thereof, and optionally a pharmaceutically acceptable excipient.

In certain embodiments, compounds described herein inhibit activity of an arginine methyltransferase (RMT) (e.g., PRMT1, PRMT3, CARM1, PRMT6, and/or PRMT8). In certain embodiments, methods of inhibiting an arginine methyltransferase are provided which comprise contacting the arginine methyltransferase with an effective amount of a compound of Formula (I) or a pharmaceutically acceptable salt thereof. The RMT may be purified or crude, and may be present in a cell, tissue, or a subject. Thus, such methods encompass inhibition of RMT activity both in vitro and in vivo. In certain embodiments, the RMT is wild-type. In certain embodiments, the RMT is overexpressed. In certain embodiments, the RMT is a mutant. In certain embodiments, the RMT is in a cell. In certain embodiments, the RMT is in an animal, e.g., a human. In some embodiments, the RMT is expressed at normal levels in a subject, but the subject would benefit from RMT inhibition (e.g., because the subject has one or more mutations in an RMT substrate that causes an increase in methylation of the substrate with normal levels of RMT). In some embodiments, the RMT is in a subject known or identified as having abnormal RMT activity (e.g., overexpression).

In certain embodiments, methods of modulating gene expression in a cell are provided which comprise contacting a cell with an effective amount of a compound of Formula (I) or a pharmaceutically acceptable salt thereof, or a pharmaceutical composition thereof. In certain embodiments, the cell is in culture in vitro. In certain embodiments, cell is in an animal, e.g., a human.

In certain embodiments, methods of modulating transcription in a cell are provided which comprise contacting a cell with an effective amount of a compound of Formula (I) or a pharmaceutically acceptable salt thereof, or a pharmaceutical composition thereof. In certain embodiments, the cell is in culture in vitro. In certain embodiments, the cell is in an animal, e.g., a human.

In some embodiments, methods of treating an RMT-mediated disorder (e.g., a PRMT1, PRMT3, CARM1, PRMT6, and/or PRMT8-mediated disorder) are provided which comprise administering to a subject suffering from an RMT-mediated disorder an effective amount of a compound described herein (e.g., a compound of Formula (I)), or a pharmaceutically acceptable salt thereof, or a pharmaceutical composition thereof. In certain embodiments, the RMT-mediated disorder is a proliferative disorder. In certain embodiments, compounds described herein are useful for treating cancer. In certain embodiments, compounds described herein are useful for treating breast cancer, prostate cancer, lung cancer, colon cancer, bladder cancer, or leukemia. In certain embodiments, the RMT-mediated disorder is a muscular disorder. In certain embodiments, the RMT-mediated disorder is an autoimmune disorder. In certain embodiments, the RMT-mediated disorder is a neurological disorder. In certain embodiments, the RMT-mediated disorder is a vascular disorder. In certain embodiments, the RMT-mediated disorder is a metabolic disorder.

Compounds described herein are also useful for the study of arginine methyltransferases in biological and pathological phenomena, the study of intracellular signal transduction pathways mediated by arginine methyltransferases, and the comparative evaluation of new RMT inhibitors.

This application refers to various issued patent, published patent applications, journal articles, and other publications, all of which are incorporated herein by reference.

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

It is to be understood that the compounds of the present invention may be depicted as different tautomers. It should also be understood that when compounds have tautomeric forms, all tautomeric forms are intended to be included in the scope of the present invention, and the naming of any compound described herein does not exclude any tautomer form. An exemplary tautomerization of a compound provided in the present application is shown below:

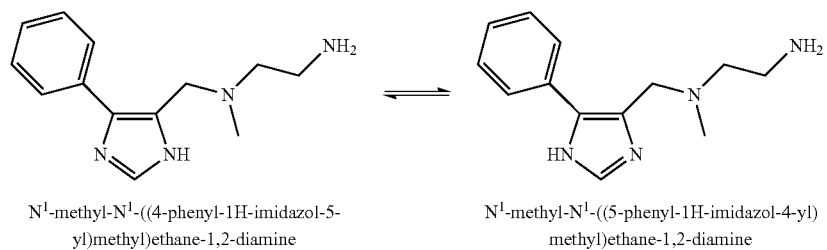 [SMILES: CN(CCN)Cc1[nH]cnc1-c1ccccc1 ; CN(CCN)Cc1nc[nH]c1-c1ccccc1]

N$^1$-methyl-N$^1$-((4-phenyl-1H-imidazol-5-yl)methyl)ethane-1,2-diamine

N$^1$-methyl-N$^1$-((5-phenyl-1H-imidazol-4-yl)methyl)ethane-1,2-diamine

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$ $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. In certain embodiments, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., —CH$_3$). In certain embodiments, the alkyl group is substituted $C_{1-10}$ alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —CF$_3$, —CF$_2$CF$_3$, —CF$_2$CF$_2$CF$_3$, —CCl$_3$, —CFCl$_2$, —CF$_2$Cl, and the like.

As used herein, "alkenyl" refers to a radical of a straight-chain or branched hydrocarbon group having from 2 to 20 carbon atoms and one or more carbon-carbon double bonds (e.g., 1, 2, 3, or 4 double bonds), and optionally one or more triple bonds (e.g., 1, 2, 3, or 4 triple bonds) ("$C_{2-20}$ alkenyl"). In certain embodiments, alkenyl does not comprise triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. In certain embodiments, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

As used herein, "alkynyl" refers to a radical of a straight-chain or branched hydrocarbon group having from 2 to 20 carbon atoms and one or more carbon-carbon triple bonds (e.g., 1, 2, 3, or 4 triple bonds), and optionally one or more double bonds (e.g., 1, 2, 3, or 4 double bonds) ("$C_{2-20}$ alkynyl"). In certain embodiments, alkynyl does not comprise double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-4}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$alkynyl groups as well as pentynyl ($C_5$), hexynyl ($C_6$), and the like. Additional examples of alkynyl include heptynyl ($C_7$), octynyl ($C_8$), and the like. In certain embodiments, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo [2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. In certain embodiments, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). In certain embodiments, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In certain embodiments, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. In certain embodiments, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary 5,6-bicyclic heteroaryl groups include, without limitation, any one of the following formulae:

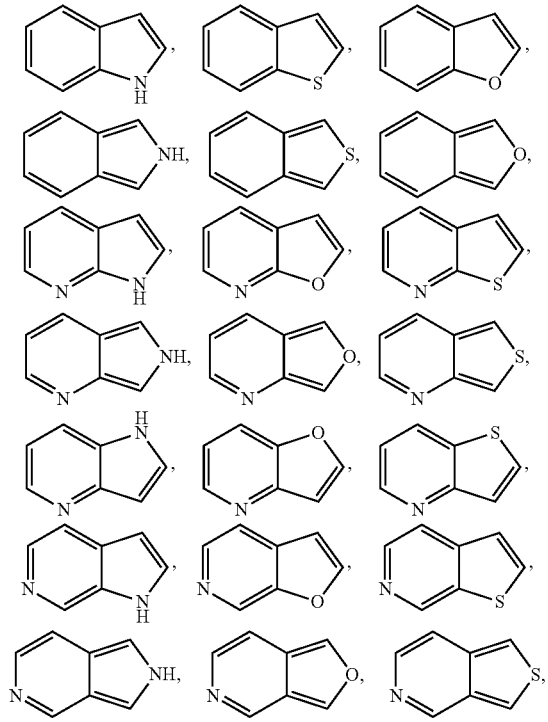

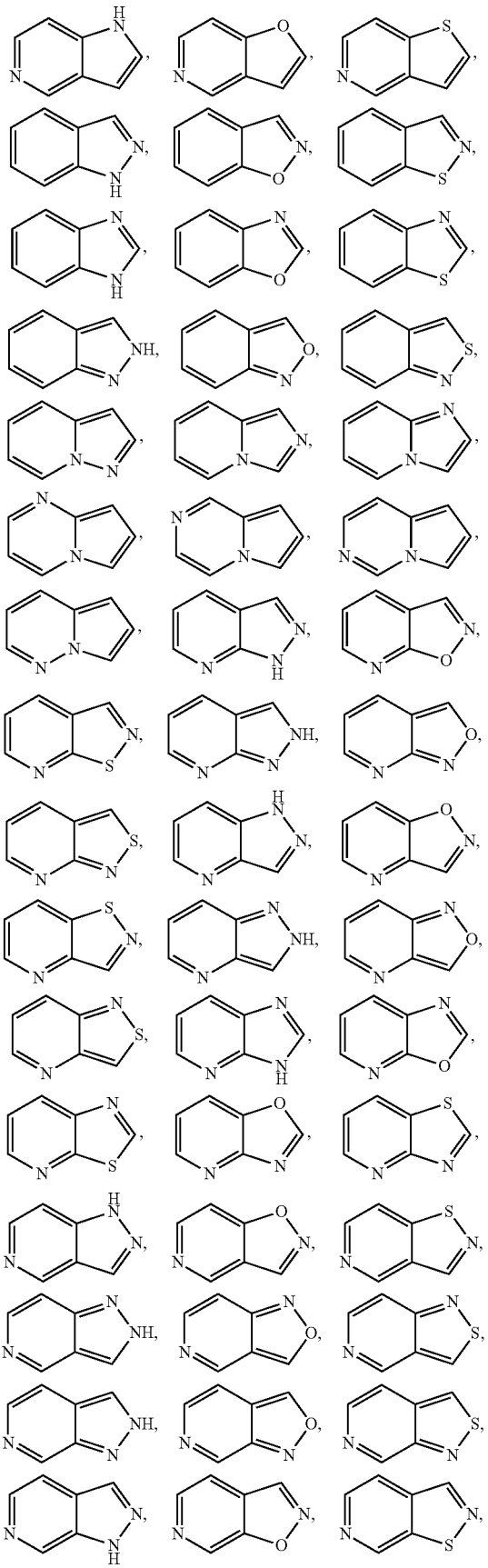

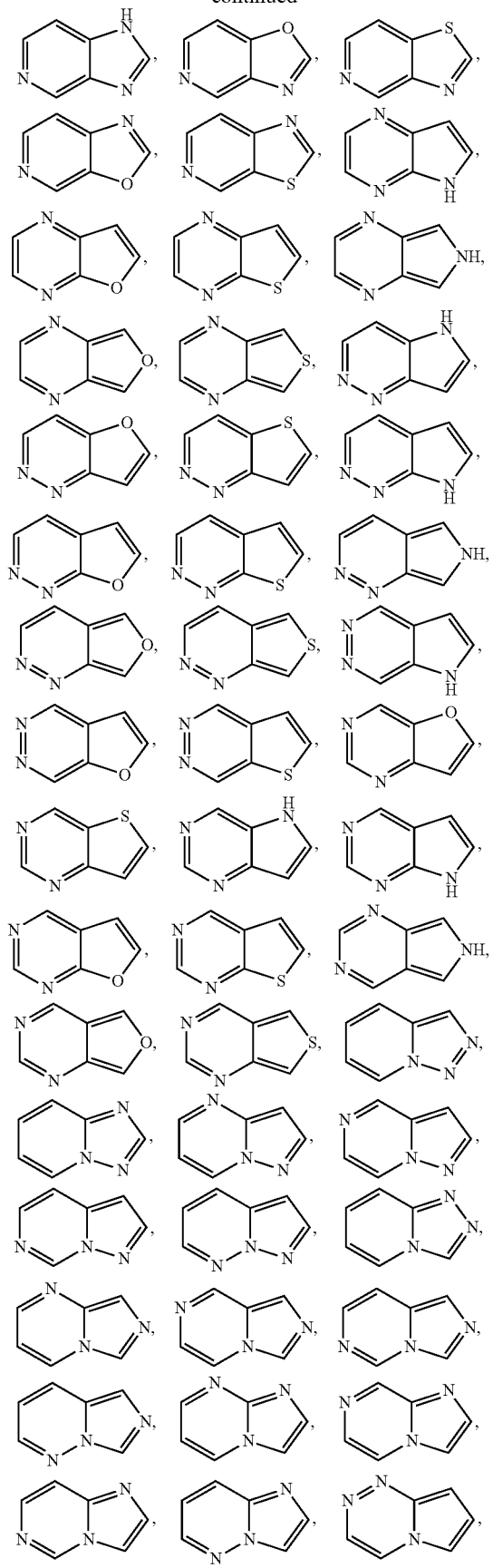
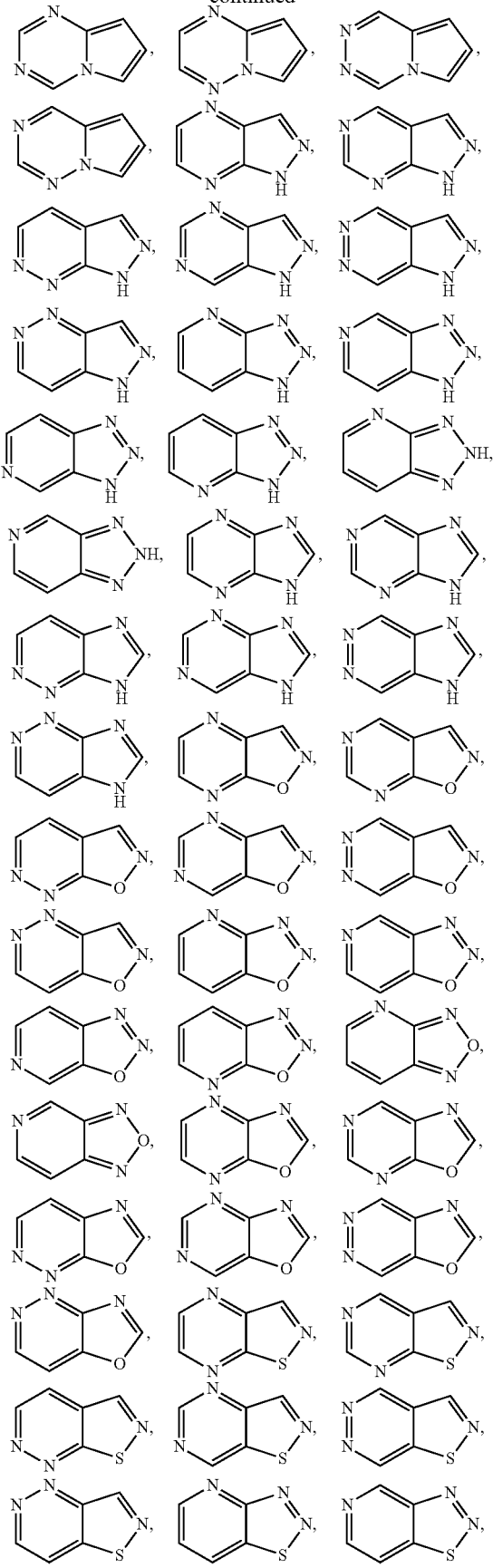

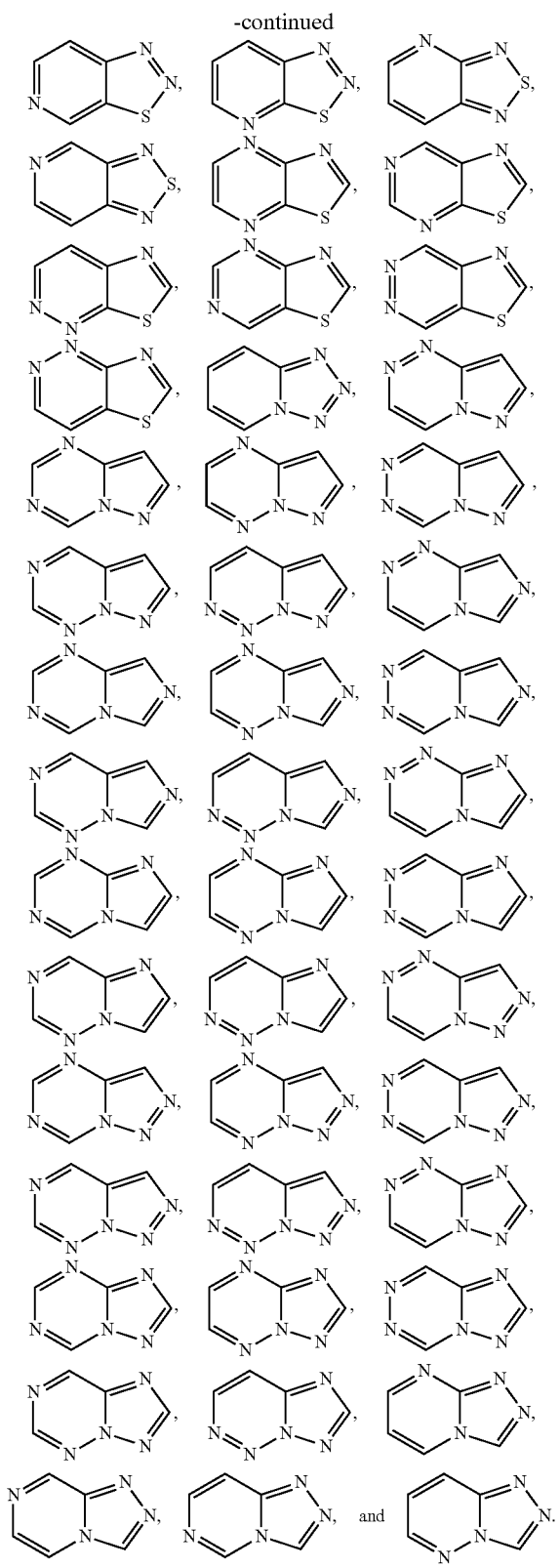

In any of the monocyclic or bicyclic heteroaryl groups, the point of attachment can be any carbon or nitrogen atom, as valency permits.

"Partially unsaturated" refers to a group that includes at least one double or triple bond. The term "partially unsatur- ated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, including any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O) NR$^{bb}$SO$_2$R$^{aa}$, NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O) (R$^{aa}$)$_2$, —OP(=O)(OR$^{cc}$)$_2$, —P(=O)$_2$N(R$^{bb}$)$_2$, —OP (=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B (OR$^{cc}$)$_2$, —BR$^{aa}$(OR$^{cc}$), C$_{1-10}$-alkyl, C$_{1-10}$-perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$-alkyl, C$_{1-10}$-perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two RU groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$-perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$-alkyl, $C_{1-10}$-perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N (R$^{ff}$)$_2$, —NR$^{ff}$C(=NR$^{ff}$)N(R$^{ff}$)$_2$, —NR$^{ff}$SO$_2$R$^{ee}$, —SO$_2$N (R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O) (R$^{ee}$)$_2$, —OP(=O)(R$^{ee}$)$_2$, —OP(=O)(OR$^{ee}$)$_2$, $C_{1-6}$alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$alkyl)$_2$, —N(C$_{1-6}$alkyl)$_2$, —N(C$_{1-6}$alkyl)$_3$$^+$X$^-$, —NH(C$_{1-6}$alkyl)$_2$$^+$X$^-$, —NH$_2$(C$_{1-6}$alkyl)$^+$X$^-$, —NH$_3$$^+$X$^-$, —N(OC$_{1-6}$alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(—O)(C$_{1-6}$ alkyl), —N(C$_{1-6}$ alkyl)C(=O)(C$_{1-6}$ alkyl), —NHCO$_2$(C$_{1-6}$ alkyl), —NHC(—O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC (=NH)(C$_{1-6}$ alkyl), —OC(=NH)OC$_{1-6}$ alkyl, —C(=NH)N (C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC (=NH)NH$_2$, —NHSO$_2$(C$_{1-6}$alkyl), —SO$_2$N(C$_{1-6}$alkyl)$_2$, —SO$_2$NH(C$_{1-6}$alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si (C$_{1-6}$alkyl)$_3$, —OSi(C$_{1-6}$ alkyl)$_3$-C(=S)N(C$_{1-6}$ alkyl)$_2$, C(=S)NH(C$_{1-6}$alkyl), C(=S)NH$_2$, —C(=O)S(C$_{1-6}$alkyl), —C(=S)SC$_{1-6}$ alkyl, —SC(=S)SC$_{1-6}$ alkyl, —P(=O)$_2$ (C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N (R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O) R$^{aa}$, —C(=O)N(R$^{cc}$)$_2$, —CO$_2$R$^{aa}$, —SO$_2$R$^{aa}$, —C(=NR$^{cc}$) R$^{aa}$, —C(=NR$^{cc}$)OR$^{aa}$, —C(=NR$^{cc}$)N(R$^{cc}$)$_2$, —SO$_2$N (R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl) benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{14}alkyl)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (e.g., a male or female of any age group, e.g., a pediatric subject (e.g, infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), rodents (e.g., rats and/or mice), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "methyltransferase" represents transferase class enzymes that are able to transfer a methyl group from a donor molecule to an acceptor molecule, e.g., an amino acid residue of a protein or a nucleic base of a DNA molecule. Methylransferases typically use a reactive methyl group bound to sulfur in S-adenosyl methionine (SAM) as the methyl donor. In some embodiments, a methyltransferase described herein is a protein methyltransferase. In some embodiments, a methyltransferase described herein is a histone methyltransferase. Histone methyltransferases (HMT) are histone-modifying enzymes, (including histone-lysine N-methyltransferase and histone-arginine N-methyltransferase), that catalyze the transfer of one or more methyl groups to lysine and arginine residues of histone proteins. In certain embodiments, a methyltransferase described herein is a histone-arginine N-methyltransferase.

As generally described above, provided herein are compounds useful as arginine methyltransferase (RMT) inhibitors. In some embodiments, the present disclosure provides a compound of Formula (I):

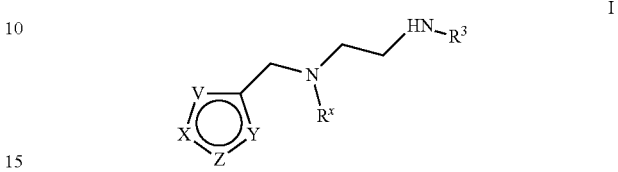

or a pharmaceutically acceptable salt thereof,
wherein
wherein:
each of X, Y, Z, and V is independently O, S, N(R$^N$)$_m$, or CR$^C$ as valence permits;
m is 0 or 1;
each instance of R$^N$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —C(=O)R$^A$, —C(=O)OR$^A$, —C(=O)SR$^A$, —C(=O)N(R$^B$)$_2$, —C(=NR$^B$)R$^A$, —C(=NNR$^B$)R$^A$, —C(=NOR$^A$)R$^A$, —C(=NR$^B$)N(R$^B$)$_2$, —C(=S)R$^A$, —C(=S)N(R$^B$)$_2$, —S(=O)R$^A$, —SO$_2$R$^A$, —SO$_2$N(R$^B$)$_2$, and a nitrogen protecting group;
each instance of R$^C$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$;
each instance of R$^A$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, an oxygen protecting group when attached to an oxygen atom, and a sulfur protecting group when attached to a sulfur atom;
each instance of R$^B$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, and a nitrogen protecting group, or two R$^B$ groups are taken together with their intervening atoms to form an optionally substituted heterocyclic ring;

each instance of Cy is independently optionally substituted $C_{3-7}$ cycloalkyl, optionally substituted 4- to 7-membered heterocyclyl, optionally substituted aryl, optionally substituted heteroaryl;

$R^3$ is independently hydrogen, $C_{1-4}$ alkyl, or $C_{3-4}$ carbocylyl;

$R^x$ is independently optionally substituted $C_{1-4}$ alkyl, or optionally substituted $C_{3-4}$ carbocylyl;

provided that at least one of X, Y, Z, and V is O, S, or $N(R^N)_m$; and provided that when V is $CR^C$, X is N, Z is $NR^N$, and Y is $CR^C$; or
V is $CR^C$, X is $NR^N$, Z is N, Y is $CR^C$; or
V is $CR^C$, X is $CR^C$, Z is $NR^N$, Y is N; or
V is $CR^C$, X is $CR^C$, Z is N, Y is $NR^N$; then each instance of $R^N$ is optionally substituted aryl or optionally substituted heteroaryl; and each instance of $R^C$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —$OR^A$, —$N(R^B)_2$, —$SR^A$, —$C(=O)R^A$, —$C(=O)OR^A$, —$C(=O)SR^A$, —$C(=O)N(R^B)_2$, —$C(=O)N(R^B)N(R^B)_2$, —$OC(=O)R^A$, —$OC(=O)N(R^B)_2$, —$NR^BC(=O)R^A$, —$NR^BC(=O)N(R^B)_2$, —$NR^BC(=O)N(R^B)N(R^B)_2$, —$NR^BC(=O)OR^A$, —$SC(=O)R^A$, —$C(=NR^B)R^A$, —$C(=NNR^B)R^A$, —$C(=NOR^A)R^A$, —$C(=NR^B)N(R^B)_2$, —$NR^BC(=NR^B)R^B$, —$C(=S)R^A$, —$C(=S)N(R^B)_2$, —$NR^BC(=S)R^A$, —$S(=O)R^A$, —$OS(=O)_2R^A$, —$SO_2R^A$, —$NR^BSO_2R^A$, and —$SO_2N(R^B)_2$;

or each instance of $R^C$ is independently selected from the group consisting of halogen, optionally substituted $C_{5-8}$ alkyl, optionally substituted alkenyl, optionally substituted carbocyclyl, optionally substituted alkynyl, optionally substituted $C_{5-8}$ cycloalkyl, optionally substituted acyl, optionally substituted aryl, or optionally substituted heteroaryl, optionally substituted alkyl-Cy, —$OR^A$, —$N(R^B)_2$, —$SR^A$, —$C(=O)R^A$, —$C(=O)OR^A$, —$C(=O)SR^A$, —$C(=O)N(R^B)_2$, —$C(=O)N(R^B)N(R^B)_2$, —$OC(=O)R^A$, —$OC(=O)N(R^B)_2$, —$NR^BC(=O)R^A$, —$NR^BC(=O)N(R^B)_2$, —$NR^BC(=O)N(R^B)N(R^B)_2$, —$NR^BC(=O)OR^A$, —$SC(=O)R^A$, —$C(=NR^B)R^A$, —$C(=NNR^B)R^A$, —$C(=NOR^A)R^A$, —$C(=NR^B)N(R^B)_2$, —$NR^BC(=NR^B)R^B$, —$C(=S)R^A$, —$C(=S)N(R^B)_2$, —$NR^BC(=S)R^A$, —$S(=O)R^A$, —$OS(=O)_2R^A$, —$SO_2R^A$, —$NR^BSO_2R^A$, and —$SO_2N(R^B)_2$; and each instance of $R^N$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —$C(=O)R^A$, —$C(=O)OR^A$, —$C(=O)SR^A$, —$C(=O)N(R^B)_2$, —$C(=NR^B)R^A$, —$C(=NNR^B)R^A$, —$C(=NOR^A)R^A$, —$C(=NR^B)N(R^B)_2$, —$C(=S)R^A$, —$C(=S)N(R^B)_2$, —$S(=O)R^A$, —$SO_2R^A$, —$SO_2N(R^B)_2$, and a nitrogen protecting group.

As generally defined in Formula (I), each of X, Y, Z, and V is independently O, S, $N(R^N)_m$, or CRc as valence permits, provided at least one of X, Y, Z, and V is O, S, or $N(R^N)_m$. As used herein, m is 0 or 1. In some embodiments, m is 0. In some embodiments, m is 1. In some embodiments, only one of X, Y, Z and V is O, S, or $NR^N$ in Formula (I). In some embodiments, a compound of Formula (I) is selected from the group consisting of

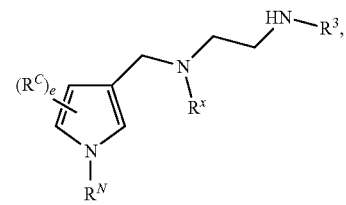

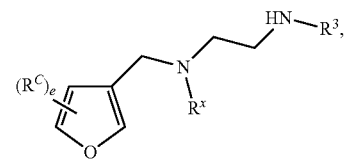

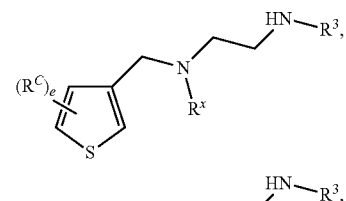

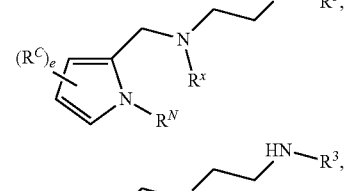

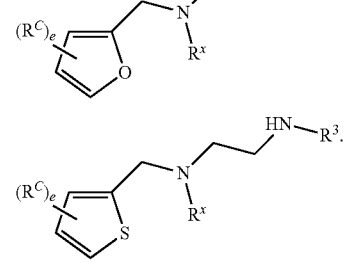

In some embodiments, only two of X, Y, Z and V are each independently O, S, N, or $NR^N$ in Formula (I). In some embodiments, a compound of Formula (I) is selected from the group consisting of

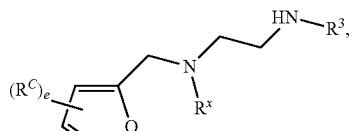

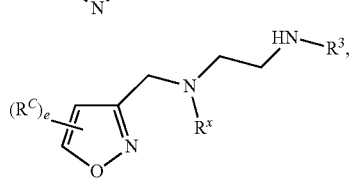

-continued
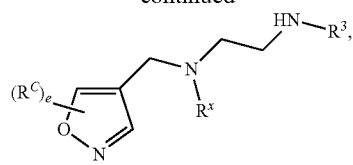
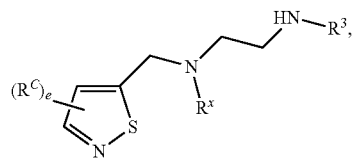
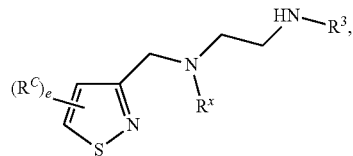
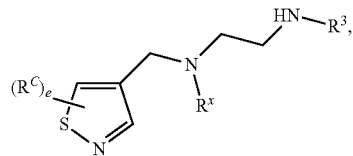
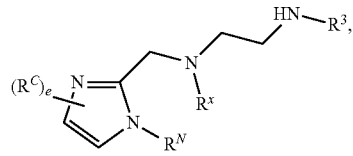
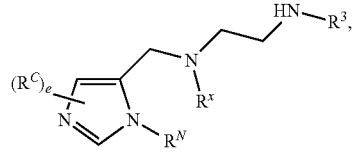
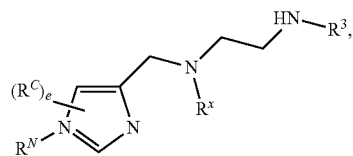
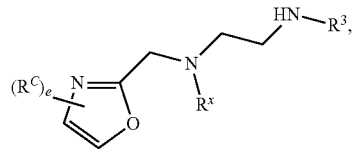
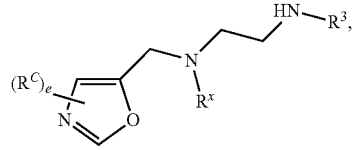
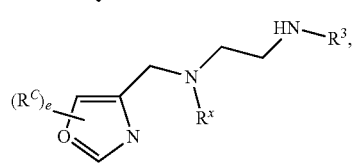
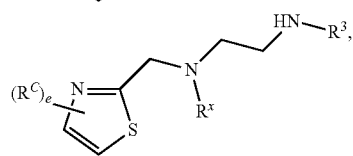
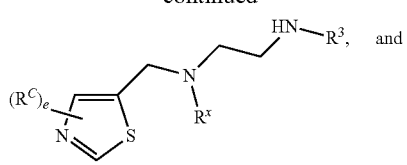
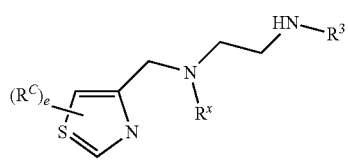
In some embodiments, only three of X, Y, Z and V are each independently O, S, N, or $NR^N$ in Formula (I). In some embodiments, a compound of Formula (I) is selected from the group consisting of
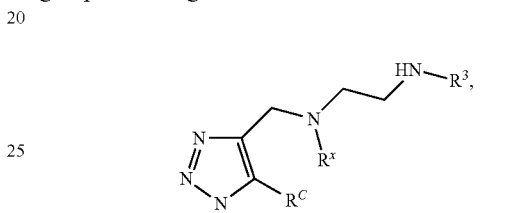
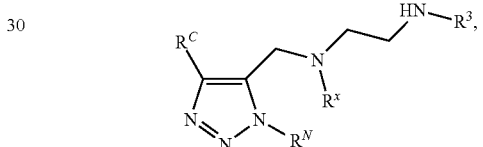
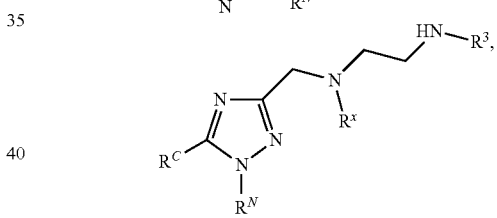
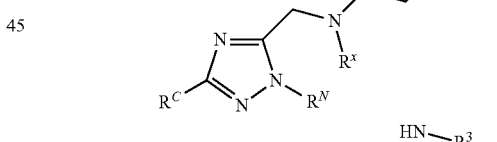
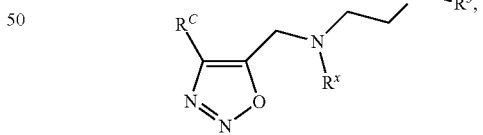
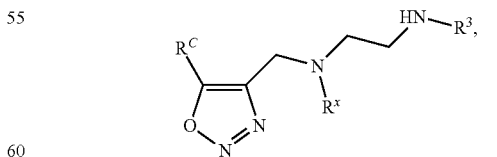
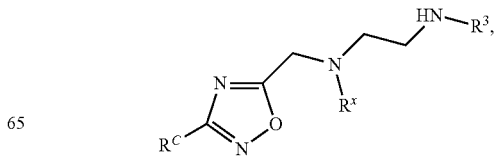

-continued

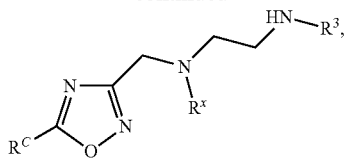
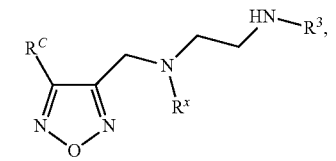
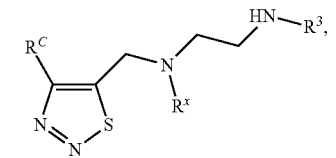
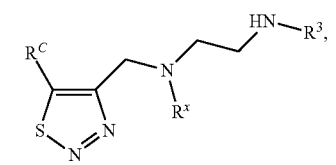
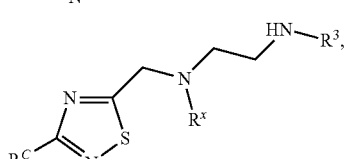
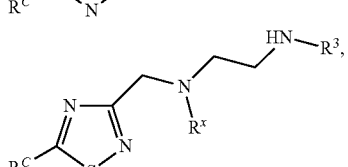
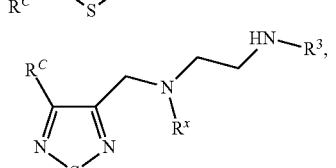
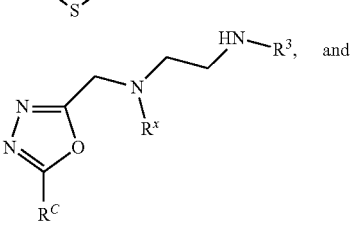
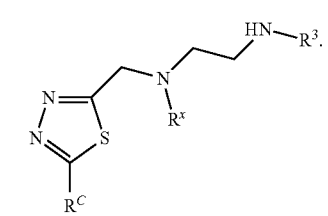

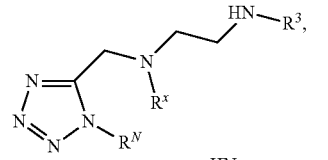
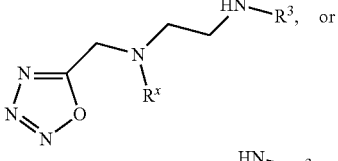
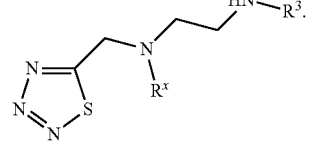

In certain embodiments, a compound of Formula (I) is of Formula (I-i), (I-ii), (I-ii) or (I-iv):

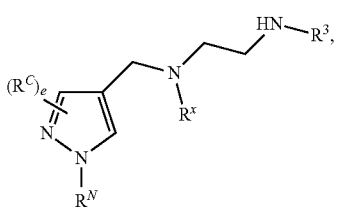

I-i

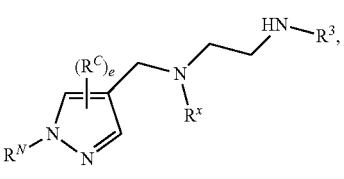

I-ii

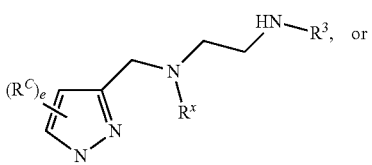

I-iii

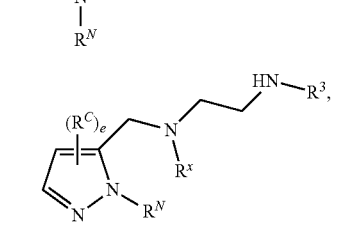

I-iv wherein:
e, $R^3$, and $R^x$ are as defined herein;
$R^N$ is optionally substituted aryl or optionally substituted heteroaryl; and
each instance of $R^C$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R)$_2$, —OC(=O)

In some embodiments, only four of X, Y, Z and V are each independently O, S, N, or NR$^N$ in Formula (I). In some embodiments, a compound of Formula (I)

$R^A$, —OC(=O)N($R^B$)$_2$, —$NR^B$C(=O)$R^A$, —$NR^B$C(=O)N($R^B$)$_2$, —$NR^B$C(=O)N($R^B$)N($R^B$)$_2$, —$NR^B$C(=O)O$R^A$, —SC(=O)$R^A$, —C(=$NR^B$)$R^A$, —C(=NN$R^B$)$R^A$, —C(=NO$R^A$)$R^A$, —C(=$NR^B$)N($R^B$)$_2$, —$NR^B$C(=$NR^B$)$R^B$, —C(=S)$R^A$, —C(=S)N($R^B$)$_2$, —$NR^B$C(=S)$R^A$, —S(=O)$R^A$, —OS(=O)$_2$$R^A$, —SO$_2$$R^A$, —$NR^B$SO$_2$$R^A$, and —SO$_2$N($R^B$)$_2$.

In certain embodiments, a compound of Formula (I) is of Formula (I-i), (I-ii), (I-ii) or (I-iv):

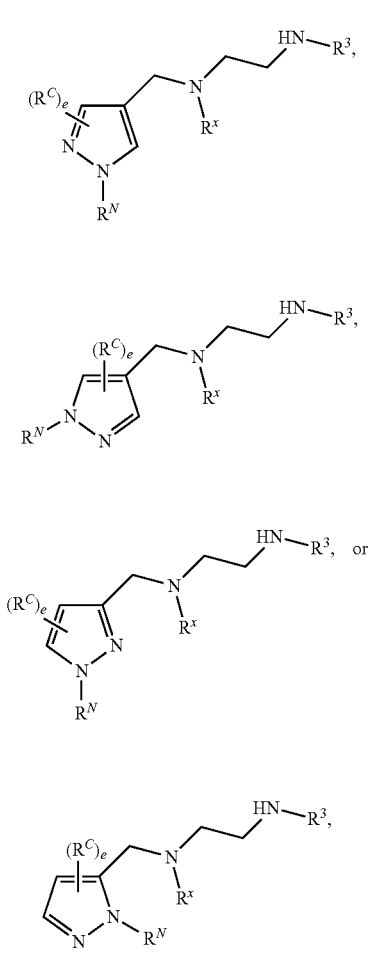

wherein:

e, $R^3$, and $R^x$ are as defined herein;

each instance of $R^C$ is independently selected from the group consisting of optionally substituted $C_{5-8}$ alkyl, optionally substituted alkenyl, optionally substituted alkynyl, optionally substituted $C_{5-8}$ carbocyclyl, optionally substituted acyl, optionally substituted aryl, or optionally substituted heteroaryl, optionally substituted alkyl-Cy, —O$R^A$, —N($R^B$)$_2$, —S$R^A$, —C(=O)$R^A$, —C(=O)O$R^A$, —C(=O)S$R^A$, —C(=O)N($R^B$)$_2$, —C(=O)N($R^B$)N($R^B$)$_2$, —OC(=O)$R^A$, —OC(=O)N($R^B$)$_2$, —NRC(=O)$R^A$, —$NR^B$C(=O)N($R^B$)$_2$, —$NR^B$C(=O)N($R^B$)N($R^B$)$_2$, —$NR^B$C(=O)O$R^A$, —SC(=O)$R^A$, —C(=$NR^B$)$R^A$, —C(=NN$R^B$)$R^A$, —C(=NO$R^A$)$R^A$, —C(=$NR^B$)N($R^B$)$_2$, —$NR^B$C(=$NR^B$)$R^B$, —C(=S)$R^A$, —C(=S)N($R^B$)$_2$, —$NR^B$C(=S)$R^A$, —S(=O)$R^A$, —OS(=O)$_2$$R^A$, —SO$_2$$R^A$, —$NR^B$SO$_2$$R^A$, and —SO$_2$N($R^B$)$_2$; and each instance of $R^N$ is independently selected from the group hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —C(=O)$R^A$, —C(=O)O$R^A$, —C(=O)S$R^A$, —C(=O)N($R^B$)$_2$, —C(=$NR^B$)$R^A$, —C(=NN$R^B$)$R^A$, —C(=NO$R^A$)$R^A$, —C(=$NR^B$)N($R^B$)$_2$, —C(=S)$R^A$, —C(=S)N($R^B$)$_2$, —S(=O)$R^A$, —SO$_2$$R^A$, —SO$_2$N($R^B$)$_2$, and a nitrogen protecting group.

In certain embodiments, a compound of Formula (I) is of Formula (II)

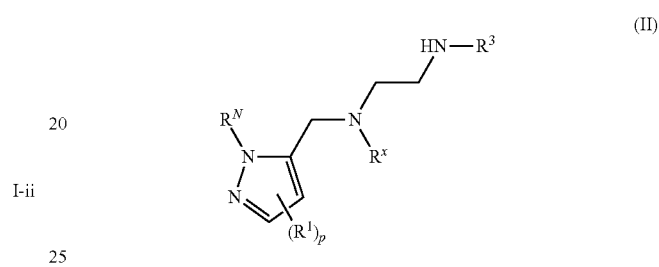

or a pharmaceutically acceptable salt thereof, wherein $R^N$ is optionally substituted aryl or optionally substituted heteroaryl; and each instance of $R^1$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —O$R^A$, —N($R^B$)$_2$, —S$R^A$, —C(=O)$R^A$, —C(=O)O$R^A$, —C(=O)S$R^A$, —C(=O)N($R^B$)$_2$, —C(=O)N($R^B$)N($R^B$)$_2$, —OC(=O)$R^A$, —OC(=O)N($R^B$)$_2$, —$NR^B$C(=O)$R^A$, —$NR^B$C(=O)N($R^B$)$_2$, —$NR^B$C(=O)N($R^B$)N($R^B$)$_2$, —$NR^B$C(=O)O$R^A$, —SC(=O)$R^A$, —C(=$NR^B$)$R^A$, —C(=NN$R^B$)$R^A$, —C(=NO$R^A$)$R^A$, —C(=$NR^B$)N($R^B$)$_2$, —$NR^B$C(=$NR^B$)$R^B$, —C(=S)$R^A$, —C(=S)N($R^B$)$_2$, —$NR^B$C(=S)$R^A$, —S(=O)$R^A$, —OS(=O)$_2$$R^A$, —SO$_2$$R^A$, —$NR^B$SO$_2$$R^A$, and —SO$_2$N($R^B$)$_2$;

or each instance of $R^1$ is independently selected from the group consisting of optionally substituted $C_{5-8}$ alkyl, optionally substituted alkenyl, optionally substituted alkynyl, optionally substituted $C_{5-8}$ cycloalkyl, optionally substituted acyl, optionally substituted aryl, or optionally substituted heteroaryl, optionally substituted alkyl-Cy, —O$R^A$, —N($R^B$)$_2$, —S$R^A$, —C(=O)$R^A$, —C(=O)O$R^A$, —C(=O)S$R^A$, —C(O)N($R^B$)$_2$, —C(=O)N($R^B$)N($R^B$)$_2$, —OC(=O)$R^A$, —OC(=O)N($R^B$)$_2$, —$NR^B$C(=O)$R^A$, —$NR^B$C(=O)N($R^B$)$_2$, —$NR^B$C(=O)N($R^B$)N($R^B$)$_2$, —$NR^B$C(=O)O$R^A$, —SC(=O)$R^A$, —C(=$NR^B$)$R^A$, —C(=NN$R^B$)$R^A$, —C(=NO$R^A$)$R^A$, —C(=$NR^B$)N($R^B$)$_2$, —$NR^B$C(=$NR^B$)$R^B$, —C(=S)$R^A$, —C(=S)N($R^B$)$_2$, —$NR^B$C(=S)$R^A$, —S(=O)$R^A$, —OS(=O)$_2$$R^A$, —SO$_2$$R^A$, —$NR^B$SO$_2$$R^A$, and —SO$_2$N($R^B$)$_2$;

and $R^N$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —C(=O)R$^A$, —C(=O)OR$^A$, —C(=O)SR$^A$, —C(=O)N(R$^B$)$_2$, —C(=NR$^B$)R$^A$, —C(=NNR$^B$)R$^A$, —C(=NOR$^A$)R$^A$, —C(=NR$^B$)N(R$^B$)$_2$, —C(=S)R$^A$, —C(=S)N(R$^B$)$_2$, —S(=O)R$^A$, —SO$_2$R$^A$, —SO$_2$N(R$^B$)$_2$, and a nitrogen protecting group; and p is 0, 1, or 2.

As defined herein, p is 0, 1, or 2. In certain embodiments, p is 0 and the compound of Formula (II) is of Formula (II-a)

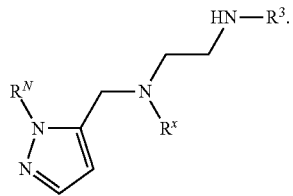
(II-a)

In certain embodiments, p is 1 and the compound of Formula (II) is of Formula (II-b)

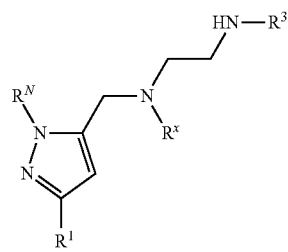
(II-b)

or Formula (II-c)

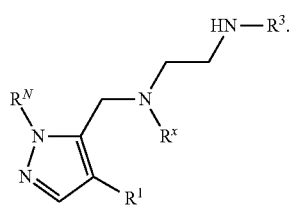
(II-c)

In certain embodiments, p is 2 and the compound of Formula (II) is of Formula (II-d)

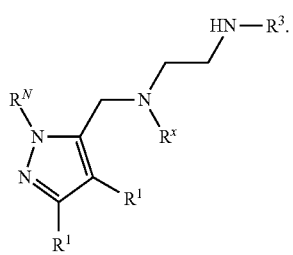
(II-d)

In certain embodiments, a provided compound is of Formula (III):

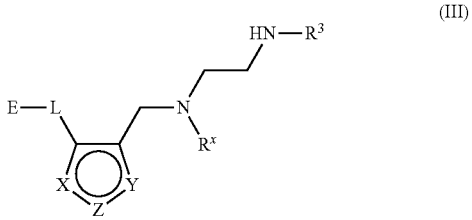
(III)

or a pharmaceutically acceptable salt thereof,
wherein:
each of X, Y, and Z is independently O, S, N(R$^N$)$_m$, or CRc as valence permits;
m is 0 or 1;
each instance of R$^N$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —C(=O)R$^A$, —C(=O)OR$^A$, —C(=O)SR$^A$, —C(=O)N(R$^B$)$_2$, —C(=NR$^B$)R$^A$, —C(=NNR$^B$)R$^A$, —C(=NOR$^A$)R$^A$, —C(=NR$^B$)N(R$^B$)$_2$, —C(=S)R$^A$, —C(=S)N(R$^B$)$_2$, —S(=O)R$^A$, —SO$_2$R$^A$, —SO$_2$N(R$^B$)$_2$, and a nitrogen protecting group;
each instance of R$^C$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$;
each instance of R$^A$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, an oxygen protecting group when attached to an oxygen atom, and a sulfur protecting group when attached to a sulfur atom;
each instance of R$^B$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, and a nitrogen protecting group, or two R$^B$ groups are taken together with their intervening atoms to form an optionally substituted heterocyclic ring;
each instance of Cy is independently optionally substituted C$_{3-7}$cycloalkyl, optionally substituted 4- to 7-membered heterocyclyl, optionally substituted aryl, optionally substituted heteroaryl;
R$^3$ is independently hydrogen, C$_{1-4}$ alkyl, or C$_{3-4}$ cycloalkyl;

$R^x$ is independently optionally substituted $C_{1-4}$ alkyl, or optionally substituted $C_{3-4}$ carbocylyl;

L is a bond, —O—, —S—, —NR$^B$—, —NR$^B$C(=O)—, —C(=O)NR$^B$—, —SC(=O)—, —C(=O)S—, —OC(=O)—, —C(=O)O—, —NR$^B$C(=S), C(=S)NR$^B$—, trans-CR$^C$=CR$^C$—, cis-CR$^C$=CR$^C$—, —C≡C—, —OC(R$^C$)$_2$—, —C(R$^C$)$_2$O—, —NR$^B$C(R$^C$)$_2$, —C(R$^C$)$_2$NR$^B$—, —SC(R$^C$)$_2$—, —C(R)S—, —S(=O)$_2$O—, —OS(=O)$_2$—, —S(=O)$_2$NR$^B$—, —NR$^B$S(=O)$_2$—, or an optionally substituted $C_{1-6}$ hydrocarbon chain, optionally wherein one or more carbon units of the hydrocarbon chain is replaced with —O—, —S—, —NR$^B$—, —NR$^B$C(=O)—, —C(=O)NR$^B$—, —SC(=O)—, —C(=O)S—, —OC(=O)—, —C(=O)O—, —NR$^B$C(=S)—, —C(=S)NR$^B$—, trans-CR$^C$=CR$^C$—, cis-CR$^C$=CR$^C$—, —C≡C—, —OC(R$^C$)$_2$—, —C(R$^C$)$_2$O—, —NR$^B$C(R$^C$)$_2$—, —C(R$^C$)$_2$NR$^B$—, —SC(R$^C$)$_2$—, —C(R$^C$)$_2$S—, —S(=O)$_2$O—, —OS(=O)$_2$—, —S(=O)$_2$NR$^B$—, —NR$^B$S(=O)$_2$—;

E is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

provided that at least one of X, Y, and Z is O, S, or N(R$^N$)$_m$; and provided that when X is N, Z is NR$^N$, and Y is CR$^C$; or X is NR$^N$, Z is N, Y is CR$^C$; or X is CR$^C$, Z is NR$^N$, Y is N; or X is CRc, Z is N, Y is NR$^N$; then each instance of R$^N$ is optionally substituted aryl or optionally substituted heteroaryl; and each instance of R$^C$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$;

or each instance of R$^C$ is independently selected from the group consisting of halogen, optionally substituted $C_{5-8}$alkyl, optionally substituted alkenyl, optionally substituted alkynyl, optionally substituted $C_{5-8}$ cycloalkyl, optionally substituted acyl, optionally substituted aryl, or optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$; and each instance of R$^N$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$, and a nitrogen protecting group.

As used herein, m is 0 or 1. In some embodiments, m is 0. In some embodiments, m is 1. In some embodiments, only one of X, Y, and Z is each independently O, S, or NR$^N$ in Formula (III). In some embodiments, a compound of Formula (III) is selected from the group consisting of

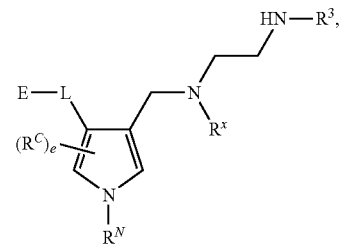

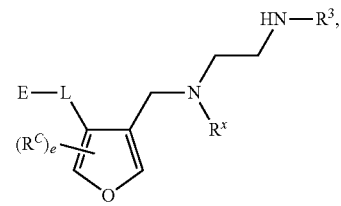

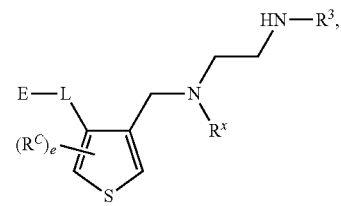

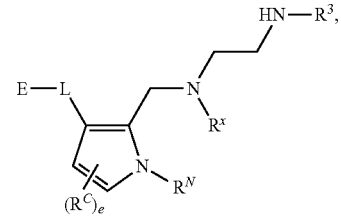

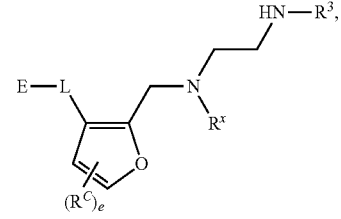

-continued
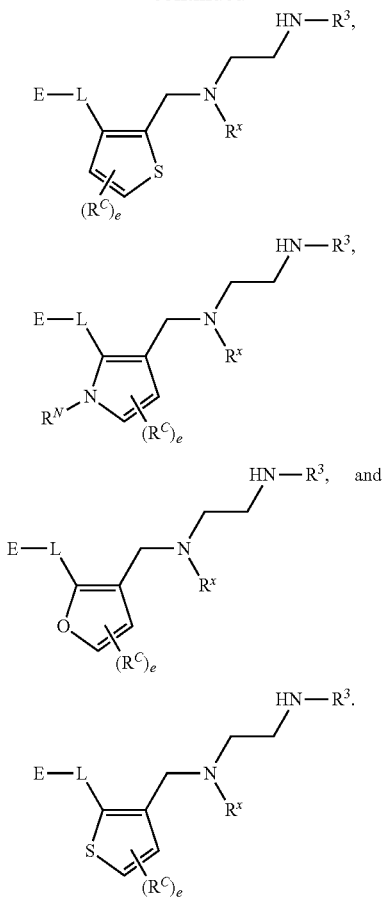
In some embodiments, only two of X, Y, Z are each independently O, S, N, or NR$^N$ in Formula (III). In some embodiments, a compound of Formula (III) is selected from the group consisting of
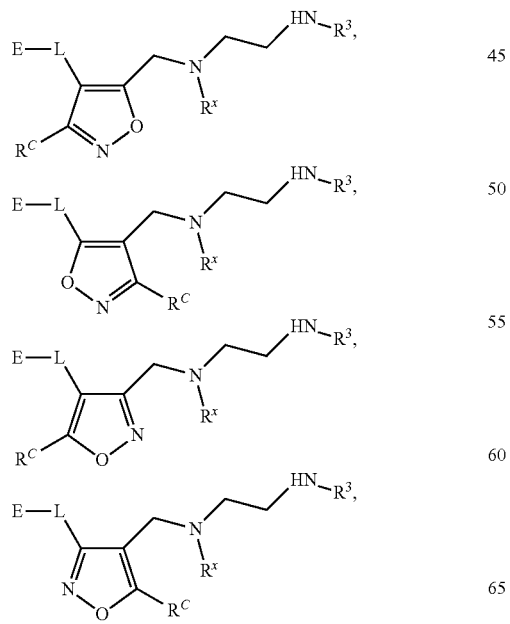
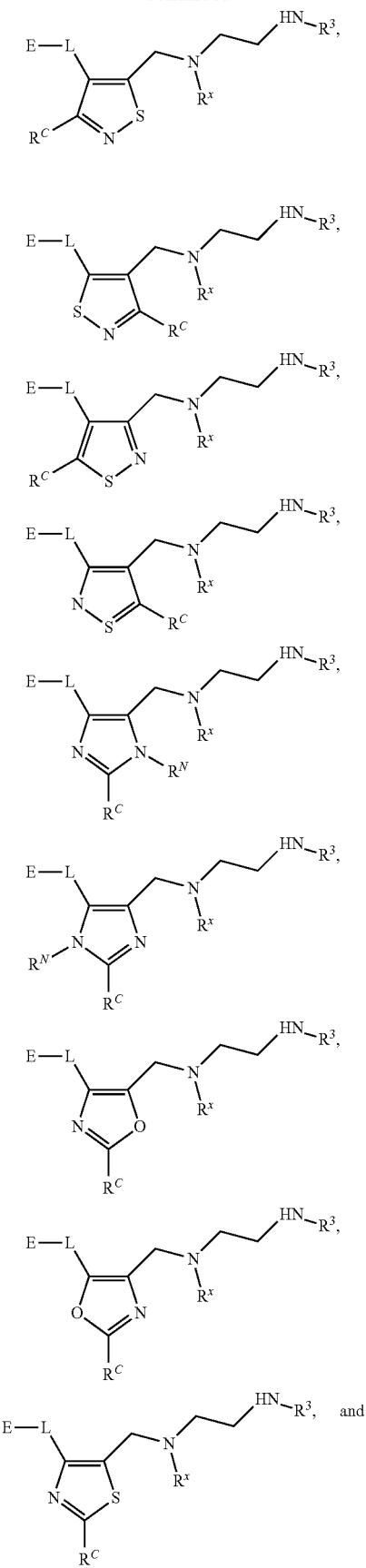

-continued
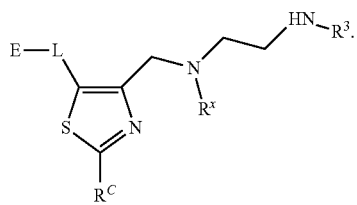
In some embodiments, only three of X, Y, Z are each independently O, S, N, or $NR^N$ in Formula (III). In some embodiments, a compound of Formula (III) is selected from the group consisting of
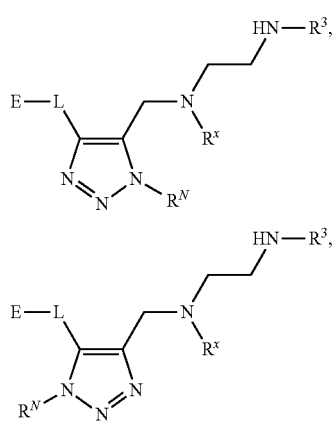
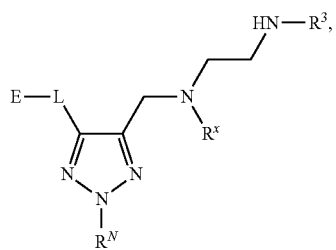
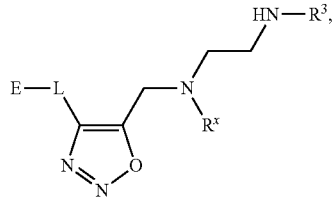
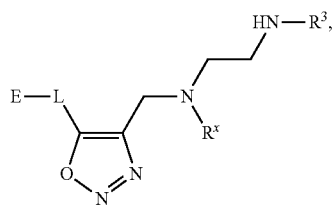
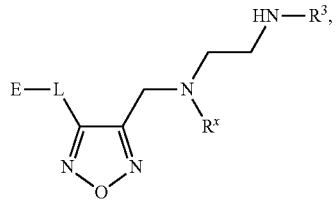
-continued
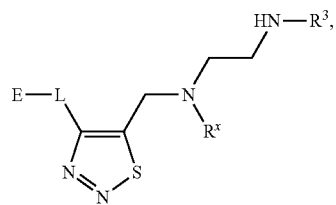
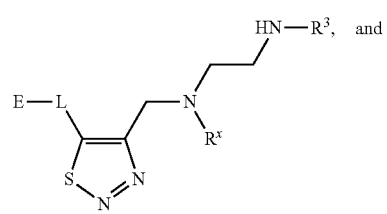
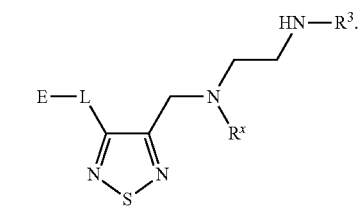
In certain embodiments, a compound of Formula (III) is of Formula (III-a), (III-b), (III-c), or (III-d):
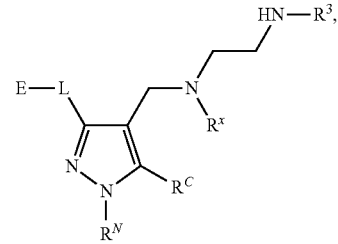
(III-a)
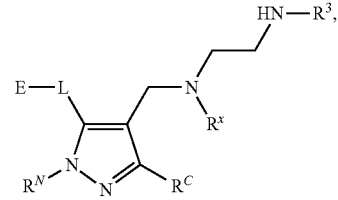
(III-b)
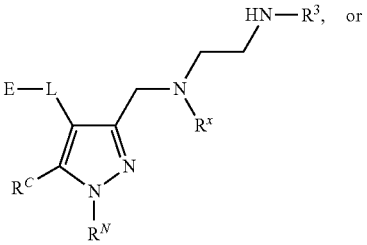
(III-c)

-continued

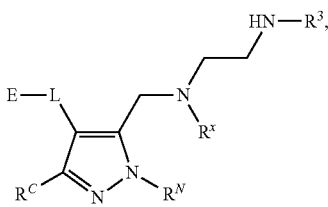
(III-d)

wherein:

each instance of $R^N$ is optionally substituted aryl or optionally substituted heteroaryl; and each instance of $R^C$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —$OR^A$, —$N(R^B)_2$, —$SR^A$, —$C(=O)R^A$, —$C(=O)OR^A$, —$C(=O)SR^A$, —$C(=O)N(R^B)_2$, —$C(=O)N(R^B)N(R^B)_2$, —$OC(=O)R^A$, —$OC(=O)N(R^B)_2$, —$NR^BC(=O)R^A$, —$NR^BC(=O)N(R^B)_2$, —$NR^BC(=O)N(R^B)N(R^B)_2$, —$NR^BC(=O)OR^A$, —$SC(=O)R^A$, —$C(=NR^B)R^A$, —$C(=NNR^B)R^A$, —$C(=NOR^A)R^A$, —$C(=NR^B)N(R^B)_2$, —$NR^BC(=NR^B)R^B$, —$C(=S)R^A$, —$C(=S)N(R^B)_2$, —$NR^BC(=S)R^A$, —$S(=O)R^A$, —$OS(=O)_2R^A$, —$SO_2R^A$, —$NR^BSO_2R^A$, and —$SO_2N(R^B)_2$.

In certain embodiments, a compound of Formula (III) is of Formula (III-a), (III-b), (III-c), or (III-d):

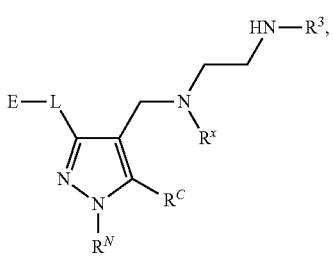
(III-a)

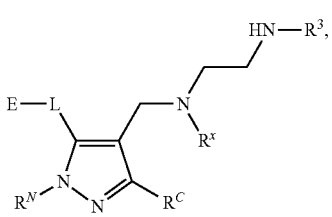
(III-b)

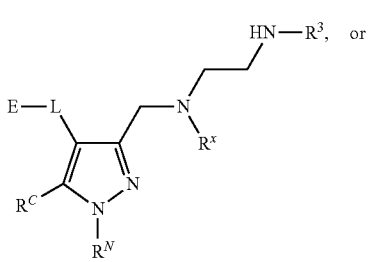
(III-c)

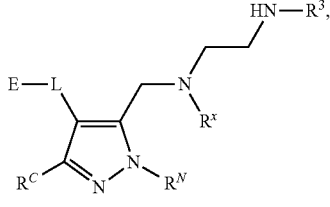
(III-d)

wherein:

each instance of $R^C$ is independently selected from the group consisting of optionally substituted $C_{5-8}$ alkyl, optionally substituted alkenyl, optionally substituted alkynyl, optionally substituted carbocyclyl, optionally substituted $C_{5-8}$ cycloalkyl, optionally substituted acyl, optionally substituted aryl, or optionally substituted heteroaryl, optionally substituted alkyl-Cy, —$OR^A$, —$N(R^B)_2$, —$SR^A$, —$C(=O)R^A$, —$C(=O)OR^A$, —$C(=O)SR^A$, —$C(=O)N(R^B)_2$, —$C(=O)N(R^B)N(R^B)_2$, —$OC(=O)R^A$, —$OC(=O)N(R^B)_2$, —$NR^BC(=O)R^A$, —$NR^BC(=O)N(R^B)_2$, —$NR^BC(=O)N(R^B)N(R^B)_2$, —$NR^BC(=O)OR^A$, —$SC(=O)R^A$, —$C(=NR^B)R^A$, —$C(=NNR^B)R^A$, —$C(=NOR^A)R^A$, —$C(=NR^B)N(R^B)_2$, —$NR^BC(=NR)R^B$, —$C(=S)R^A$, —$C(=S)N(R^B)_2$, —$NR^BC(=S)R^A$, —$S(=O)R^A$, —$OS(=O)_2R^A$, —$SO_2R^A$, —$NR^BSO_2R^A$, and —$SO_2N(R^B)_2$; and each instance of $R^N$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —$C(=O)R^A$, —$C(=O)OR^A$, —$C(=O)SR^A$, —$C(=O)N(R^B)_2$, —$C(=NR^B)R^A$, —$C(=NNR^B)R^A$, —$C(=NOR^A)R^A$, —$C(=NR^B)N(R^B)_2$, —$C(=S)R^A$, —$C(=S)N(R^B)_2$, —$S(=O)R^A$, —$SO_2R^A$, —$SO_2N(R^B)_2$, and a nitrogen protecting group.

As used herein, e is 0, 1, 2, 3, or 4, as valence permits. In some embodiments, e is 0. In some embodiments, e is 1. In some embodiments, e is 2. In some embodiments, e is 3. In some embodiments, e is 4.

In certain embodiments, a provided compound is of Formula (III-e):

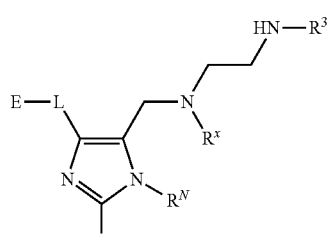
(III-e)

or a pharmaceutically acceptable salt thereof, wherein $R^3$, $R^x$, $R^N$, $R^C$, L, and E are defined herein.

In certain embodiments, a provided compound is of Formula (III-f):

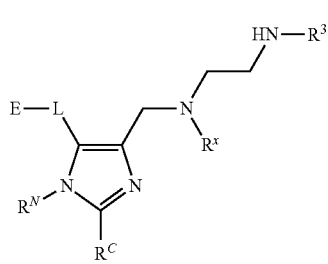

(III-f)

or a pharmaceutically acceptable salt thereof, wherein $R^3$, $R^x$, $R^N$, $R^C$, L, and E are defined herein.

In certain embodiments, a provided compound is of Formula (III-g):

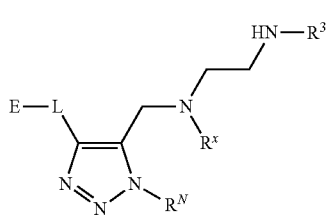

(III-g)

or a pharmaceutically acceptable salt thereof, wherein $R^3$, $R^x$, $R^N$, L, and E are defined herein.

In certain embodiments, a provided compound is of Formula (III-h):

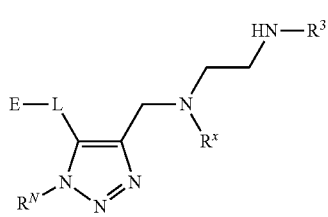

(III-h)

or a pharmaceutically acceptable salt thereof, wherein $R^3$, $R^x$, $R^N$, L, and E are defined herein.

In certain embodiments, a provided compound is of Formula (III-i):

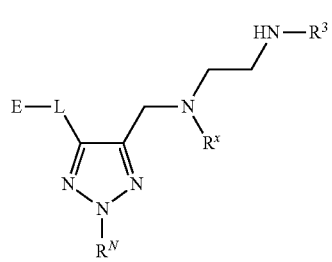

(III-i)

or a pharmaceutically acceptable salt thereof, wherein $R^3$, $R^x$, $R^N$, L, and E are defined herein.

In certain embodiments, a provided compound is of Formula (III-j):

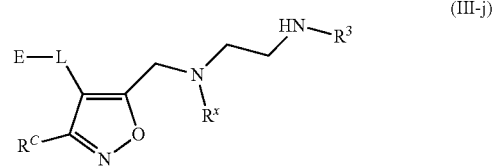

(III-j)

or a pharmaceutically acceptable salt thereof, wherein $R^3$, $R^x$, $R^C$, L, and E are defined herein.

In certain embodiments, a provided compound is of Formula (III-k):

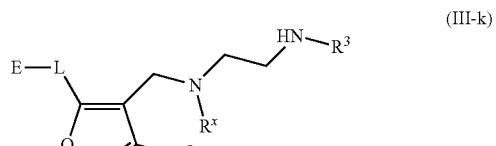

(III-k)

or a pharmaceutically acceptable salt thereof, wherein $R^3$, $R^x$, $R^C$, L, and E are defined herein.

In certain embodiments, a provided compound is of Formula (III-l):

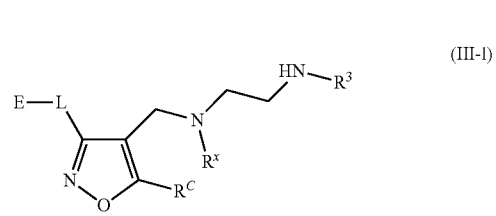

(III-l)

or a pharmaceutically acceptable salt thereof, wherein $R^3$, $R^x$, $R^C$, L, and E are defined herein.

In certain embodiments, a provided compound is of Formula (III-m):

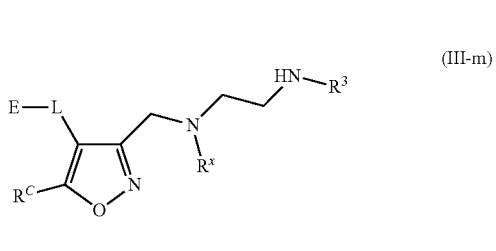

(III-m)

or a pharmaceutically acceptable salt thereof, wherein $R^3$, $R^x$, $R^C$, L, and E are defined herein.

In certain embodiments, a provided compound is of Formula (III-n):

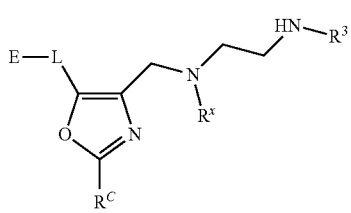 (III-n)

or a pharmaceutically acceptable salt thereof, wherein $R^3$, $R^x$, $R^C$, L, and E are defined herein.

In certain embodiments, a provided compound is of Formula (III-o):

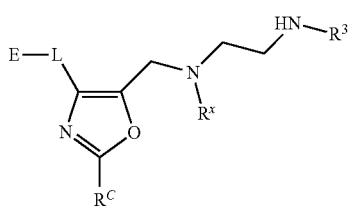 (III-o)

or a pharmaceutically acceptable salt thereof, wherein $R^3$, $R^x$, $R^C$, L, and E are defined herein.

In certain embodiments, a provided compound is of Formula (III-p):

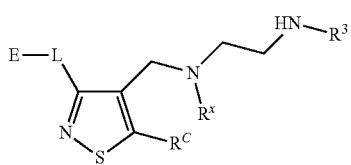 (III-p)

or a pharmaceutically acceptable salt thereof, wherein $R^3$, $R^x$, $R^C$, L, and E are defined herein.

In certain embodiments, a provided compound is of Formula (III-q):

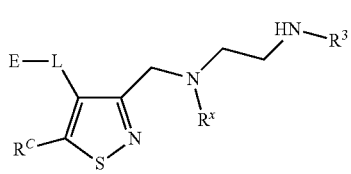 (III-q)

or a pharmaceutically acceptable salt thereof, wherein $R^3$, $R^x$, $R^C$, L, and E are defined herein.

In certain embodiments, a provided compound is of Formula (III-r):

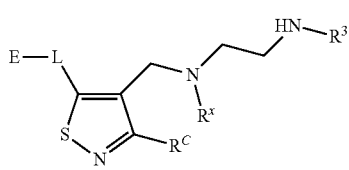 (III-r)

or a pharmaceutically acceptable salt thereof, wherein $R^3$, $R^x$, $R^C$, L, and E are defined herein.

In certain embodiments, a provided compound is of Formula (III-s):

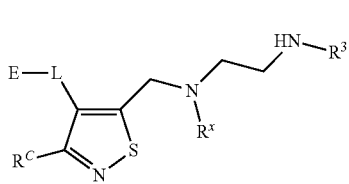 (III-s)

or a pharmaceutically acceptable salt thereof, wherein $R^3$, $R^x$, $R^C$, L, and E are defined herein.

In certain embodiments, a provided compound is of Formula (III-t):

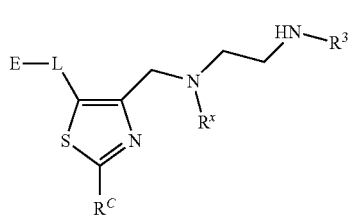 (III-t)

or a pharmaceutically acceptable salt thereof, wherein $R^3$, $R^x$, $R^C$, L, and E are defined herein.

In certain embodiments, a provided compound is of Formula (III-u):

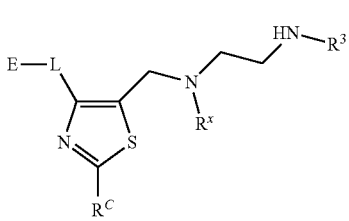 (III-u)

or a pharmaceutically acceptable salt thereof, wherein $R^3$, $R^x$, $R^C$, L, and E are defined herein.

In certain embodiments, a provided compound is of Formula (III-v):

(III-v)

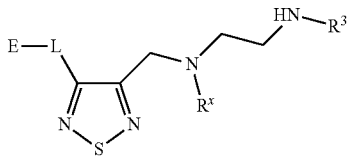

or a pharmaceutically acceptable salt thereof, wherein $R^3$, $R^x$, L, and E are defined herein.

In certain embodiments, a provided compound is of Formula (III-w):

(III-w)

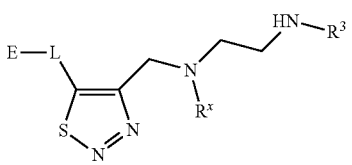

or a pharmaceutically acceptable salt thereof, wherein $R^3$, $R^x$, L, and E are defined herein.

In certain embodiments, a provided compound is of Formula (III-x):

(III-x)

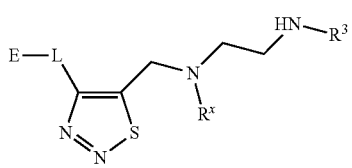

or a pharmaceutically acceptable salt thereof, wherein $R^3$, $R^x$, L, and E are defined herein.

In certain embodiments, a provided compound is of Formula (III-y):

(III-y)

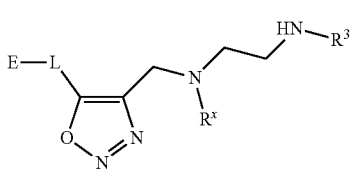

or a pharmaceutically acceptable salt thereof, wherein $R^3$, $R^x$, L, and E are defined herein.

In certain embodiments, a provided compound is of Formula (III-z):

(III-z)

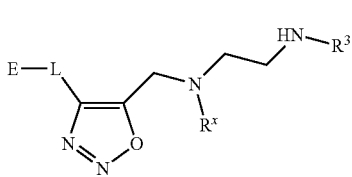

or a pharmaceutically acceptable salt thereof, wherein $R^3$, $R^x$, L, and E are defined herein.

In certain embodiments, a provided compound is of Formula (III-aa):

(III-aa)

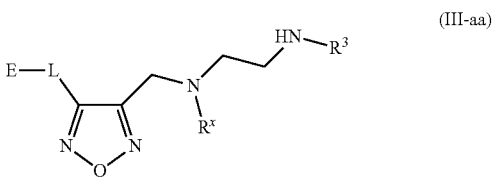

or a pharmaceutically acceptable salt thereof, wherein $R^3$, $R^x$, L, and E are defined herein.

As generally defined herein, L is independently a bond, —O—, —S—, —NR$^B$—, —NR$^B$C(=O)—, —C(=O)NR$^B$—, —SC(=O)—, —C(=O)S—, —OC(=O)—, —C(=O)O—, —NR$^B$C(=O)O—, —OC(=O)NR$^B$—, —NR$^B$C(=S)—, —C(=S)NR$^B$—, trans-CR$^C$=CR$^C$—, cis-CR$^C$=CR$^C$—, —C≡C—, —OC(R$^C$)$_2$—, —C(R$^C$)$_2$O—, —NR$^B$C(R$^C$)$_2$—, —C(R$^C$)$_2$NR$^B$—, —SC(R$^C$)$_2$—, —C(R$^C$)$_2$S—, —S(=O)$_2$O—, —OS(=O)$_2$—, —S(=O)$_2$NR$^B$—, —NR$^B$S(=O)$_2$—, or an optionally substituted $C_{1-6}$ hydrocarbon chain, optionally wherein one or more carbon units of the hydrocarbon chain is replaced with —O—, —S—, —NR$^B$—, —NR$^B$C(=O)—, —C(=O)NR$^B$—, —SC(=O)—, —C(=O)S—, —OC(=O)—, —C(=O)O—, —NR$^B$C(=O)O—, —OC(=O)NR$^B$—, —NR$^B$C(=S)—, —C(=S)NR$^B$—, trans-CR$^C$=CR$^C$—, cis-CR$^C$=CR$^C$—, —C≡C—, —OC(R$^C$)$_2$—, —C(R$^C$)$_2$O—, —NR$^B$C(R$^C$)$_2$—, —C(R$^C$)$_2$NR$^B$—, —SC(R$^C$)$_2$—, —C(R$^C$)$_2$—, —S(=O)$_2$O—, —OS(=O)$_2$—, —S(=O)$_2$NR$^B$—, —NR$^B$S(=O)$_2$—. In some embodiments, L is a bond. L may contain 0-4 carbon or hetero atoms in the backbone of L. L may be saturated or unsaturated. L may be substituted or unsubstituted. L may be branched or unbranched. In certain embodiments, L is a bond. In certain embodiments, L is —O—. In certain embodiments, L is —S—. In certain embodiments, L is —NR$^B$—. In certain embodiments, L is —NH—. In certain embodiments, L is —NR$^B$C(=O)—. In certain embodiments, L is —NHC(=O)—. In certain embodiments, L is —C(=O)NR$^B$—. In certain embodiments, L is —C(=O)NH—. In certain embodiments, L is —SC(=O)—. In certain embodiments, L is —NR$^B$C(=O)O—. In certain embodiments, L is —OC(=O)NR$^B$—. In certain embodiments, L is —C(=O)S—. In certain embodiments, L is —OC(=O)—. In certain embodiments, L is —C(=O)O—. In certain embodiments, L is —NR$^B$C(=S)—. In certain embodiments, L is —NHC(=S)—. In certain embodiments, L is —C(=S)NR$^B$—. In certain embodiments, L is —C(=S)NH—. In certain embodiments, L is trans-CR$^C$=CR$^C$—. In certain embodiments, L is trans-CH=CH—. In certain embodiments, L is cis-CR$^C$=CR$^C$—. In certain embodiments, L is cis-CH=CH—. In certain embodiments, L is —C≡S—. In certain embodiments, L is —OC(R$^C$)$_2$—. In certain embodiments, L is —O—(CH$_2$)$_s$—. As used herein, s is 1, 2, 3, 4, 5, or 6. In certain embodiments, L is —OCH$_2$—. In certain embodiments, L is —O(CH$_2$)$_2$—. In certain embodiments, L is —O(CH$_2$)$_3$—. In certain embodiments, L is —O(CH$_2$)$_4$—. In certain embodiments, L is —O(CH$_2$)$_5$—. In certain embodiments, L is —O(CH$_2$)$_6$—. In certain embodiments, L is —C(R$^C$)$_2$O—. In certain embodiments, L is —(CH$_2$)$_s$O—. In certain embodiments, L is —CH$_2$O—. In certain embodiments, L is —(CH$_2$)$_2$O—. In certain embodiments, L is —(CH$_2$)$_3$O—. In certain embodiments, L is —(CH$_2$)$_4$O—. In certain embodiments, L is —(CH$_2$)$_5$O—. In certain embodiments, L is —(CH$_2$)$_6$O—. In certain embodiments, L is —NR$^B$C(R$^C$)$_2$—. In certain embodiments, L is —NR$^B$(CH$_2$)$_s$—. In certain embodiments, L is —NR$^B$CH$_2$—. In certain embodiments, L is —NR$^B$(CH$_2$)$_2$—. In certain embodiments, L is —NR$^B$(CH$_2$)$_3$—. In certain embodiments, L is —NR$^B$(CH$_2$)$_4$—. In certain embodiments, L is —NR$^B$(CH$_2$)$_5$—. In certain embodiments, L is —NR$^B$(CH$_2$)$_6$—. In certain embodiments, L is —NHCH$_2$—. In certain embodiments, L is —NH(CH$_2$)$_2$—. In certain embodiments, L is —NH(CH$_2$)$_3$—. In certain embodiments, L is —NH(CH$_2$)$_4$—. In certain embodiments, L is —NH(CH$_2$)$_5$—. In certain embodiments, L is —NH(CH$_2$)$_6$—. In certain embodiments, L is —(CH$_2$)$_s$NR$^B$—. In certain embodiments, L is —CH$_2$NR$^B$—. In certain embodiments, L is —(CH$_2$)$_2$NR$^B$—. In certain embodiments, L is —(CH$_2$)$_3$NR$^B$—. In certain embodiments, L is —(CH$_2$)$_4$NR$^B$—. In certain embodiments, L is —(CH$_2$)$_5$NR$^B$—. In certain embodiments, L is —(CH$_2$)$_6$NR$^B$—. In certain embodiments, L is —C(R$^C$)$_2$NH—. In certain embodiments, L is —CH$_2$NH—. In certain embodiments, L is —(CH$_2$)$_2$NH—. In certain embodiments, L is —(CH$_2$)$_3$NH—. In certain embodiments, L is —(CH$_2$)$_4$NH—. In certain embodiments, L is —(CH$_2$)$_5$NH—. In certain embodiments, L is —(CH$_2$)$_6$NH—. In certain embodiments, L is —SC(R$^C$)$_2$—. In certain embodiments, L is —SCH$_2$—. In certain embodiments, L is —C(R$^C$)$_2$S—. In certain embodiments, L is —CH$_2$S—. In certain embodiments, L is —S(=O)$_2$O—. In certain embodiments, L is —OS(=O)$_2$—. In certain embodiments, L is —S(=O)$_2$NR$^B$—. In certain embodiments, L is —S(=O)$_2$NH—. In certain embodiments, L is —NR$^B$S(=O)$_2$—. In certain embodiments, L is —NHS(=O)$_2$—. In certain embodiments, L is a substituted C$_{1-4}$ hydrocarbon chain. In certain embodiments, L is an unsubstituted C$_{1-4}$ hydrocarbon chain. In certain embodiments, L is a substituted C$_2$ hydrocarbon chain. In certain embodiments, L is an unsubstituted C$_2$ hydrocarbon chain. In certain embodiments, L is a substituted C$_3$ hydrocarbon chain. In certain embodiments, L is an unsubstituted C$_3$ hydrocarbon chain. In certain embodiments, L is a substituted C$_4$ hydrocarbon chain. In certain embodiments, L is an unsubstituted C$_4$ hydrocarbon chain. In certain embodiments, L is an unsubstituted C$_5$ hydrocarbon chain. In certain embodiments, L is an unsubstituted C$_6$ hydrocarbon chain. In certain embodiments, L is —(CH$_2$)$_s$—. In certain embodiments, L is —CH$_2$—. In certain embodiments, L is —(CH$_2$)$_2$—. In certain embodiments, L is —(CH$_2$)$_3$—. In certain embodiments, L is —(CH$_2$)$_4$—. In certain embodiments, L is —(CH$_2$)$_5$—. In certain embodiments, L is —(CH$_2$)$_6$—. In certain embodiments, L is an optionally substituted C$_{1-6}$ hydrocarbon chain, wherein one or more carbon units of the hydrocarbon chain is replaced with —O—, —S—, —NR$^B$—, —NR$^B$C(=O)—, —C(=O)NR$^B$—, —NR$^B$C(=O)O—, —OC(=O)NR$^B$—, —SC(=O)—, —C(=O)S—, —OC(=O)—, —C(=O)O—, —NR$^B$C(=S)—, —C(=S)NR$^B$—, trans-CR$^C$=CR$^C$—, cis-CR$^C$=CR$^C$—, —C≡C—, —S(=O)$_2$O—, —OS(=O)$_2$—, —S(=O)$_2$NR$^B$—, or —NR$^B$S(=O)$_2$—. In certain embodiments, L is —(CH$_2$)$_s$—NR$^B$C(=O)—(CH$_2$)$_{s1}$—. In certain embodiments, L is —(CH$_2$)$_s$—C(=O)NR$^B$—(CH$_2$)$_{s1}$—. In certain embodiments, L is —(CH$_2$)$_s$—NR$^B$C(=O)O—(CH$_2$)$_{s1}$—. In certain embodiments, L is —(CH$_2$)$_s$—OC(=O)NR$^B$—(CH$_2$)$_{s1}$—. In certain embodiments, L is —(CH$_2$)$_s$—OC(=O)—(CH$_2$)$_{s1}$—. In certain embodiments, L is —(CH$_2$)$_s$—OC(=O)—(CH$_2$)$_{s1}$—. In certain embodiments, L is —(CH$_2$)—SC(=O)—(CH$_2$)$_{s1}$—. In certain embodiments, L is —(CH$_2$)—C(=O)S—(CH$_2$)$_{s1}$—. In certain embodiments, L is —(CH$_2$)$_s$-trans-CR$^C$=CR$^C$—(CH$_2$)$_{s1}$—. In certain embodiments, L is —(CH$_2$)-cis-CR$^C$=CR$^C$—(CH$_2$)$_{s1}$—. In certain embodiments, L is —(CH$_2$)—C≡C—(CH$_2$)$_{s1}$—. In certain embodiments, L is —(CH$_2$)$_s$—S(=O)$_2$O—(CH$_2$)$_{s1}$—. In certain embodiments, L is —(CH$_2$)$_s$—OS(=O)$_2$—(CH$_2$)$_{s1}$—. In certain embodiments, L is —(CH$_2$)$_s$—S(=O)$_2$NR$^B$—(CH$_2$)$_{s1}$—. In certain embodiments, L is —(CH$_2$)$_s$—NR$^B$S(=O)$_2$—(CH$_2$)$_{s1}$—. In certain embodiments, L is —(CH$_2$)$_s$—S(=O)$_2$NR$^B$—(CH$_2$)$_{s1}$—. In certain embodiments, L is —(CH$_2$)$_s$—O—(CH$_2$)$_{s1}$—. In certain embodiments, L is —(CH$_2$)$_s$—S—(CH$_2$)$_{s1}$—. In certain embodiments, L is —(CH$_2$)$_s$—NR$^B$—(CH$_2$)$_{s1}$—. In certain embodiments, L is —(CH$_2$)$_s$—O—(CH$_2$)$_{s1}$O—. In certain embodiments, L is —O(CH$_2$)$_s$—O—(CH$_2$)$_{s1}$—. As used herein, each of s and s1 is independently 0, 1, 2, 3, 4, 5, or 6. In certain embodiments, s is 0. In certain embodiments, s is 1. In certain embodiments, s is 2. In certain embodiments, s is 3. In certain embodiments, s is 4. In certain embodiments, s is 5. In certain embodiments, s is 6. In certain embodiments, s1 is 0. In certain embodiments, s1 is 1. In certain embodiments, s1 is 2. In certain embodiments, s1 is 3. In certain embodiments, s1 is 4. In certain embodiments, s1 is 5. In certain embodiments, s1 is 6.

As generally defined herein, E is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, E is hydrogen. In certain embodiments, E is optionally substituted alkyl. In certain embodiments, E is C$_{1-6}$ alkyl. In certain embodiments, E is methyl. In certain embodiments, E is ethyl. In certain embodiments, E is propyl. In certain embodiments, E is pentyl. In certain embodiments, E is isopropyl, isobutyl, or isopentyl. In certain embodiments, E is substituted alkenyl. In certain embodiments, E is unsubstituted alkenyl. In certain embodiments, E is vinyl. In certain embodiments, E is substituted alkynyl. In certain embodiments, E is unsubstituted alkynyl. In certain embodiments, E is ethynyl. In certain embodiments, E is substituted carbocyclyl. In certain embodiments, E is unsubstituted carbocyclyl. In certain embodiments, E is substituted cyclopropyl. In certain embodiments, E is unsubstituted cyclopropyl. In certain embodiments, E is substituted cyclobutyl. In certain embodiments, E is unsubstituted cyclobutyl. In certain embodiments, E is substituted heterocyclyl. In certain embodiments, E is unsubstituted heterocyclyl. In certain embodiments, E is optionally substituted monocyclic heterocyclyl. In certain embodiments, E is optionally substituted five-membered heterocyclyl. In certain embodiments, E is optionally substituted six-membered heterocyclyl. In certain embodiments, E is optionally substituted bicyclic heterocyclyl. In certain embodiments, E is optionally substituted six-membered heterocyclyl. In certain embodiments, E is substituted aryl. In certain embodiments, E is of Formula (i),

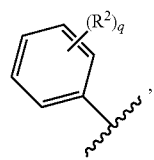

wherein R$^2$ and q are defined herein. In certain embodiments, E is phenyl. In certain embodiments, E is substituted heteroaryl. In certain embodiments, E is unsubstituted heteroaryl. In certain embodiments, E is optionally substituted bicyclic heteroaryl. In certain embodiments, E is an optionally substituted monocyclic heteroaryl ring fused with an optionally substituted monocyclic aryl ring. In certain embodiments, E is an optionally substituted monocyclic heteroaryl ring fused with another optionally substituted monocyclic heteroaryl ring. E may be an optionally substituted 6,5-membered heteroaryl ring or an optionally substituted 5,6-membered heteroaryl ring. In certain embodiments, E is an optionally substituted monocyclic 5-membered heteroaryl ring fused with an optionally substituted monocyclic 6-membered aryl ring. In certain embodiments, E is an optionally substituted monocyclic 5-membered heteroaryl ring fused with an optionally substituted monocyclic 6-membered heteroaryl ring. The point of attachment may be at any atom of E, as valency permits. In certain embodiments, E is of Formula (e-1):

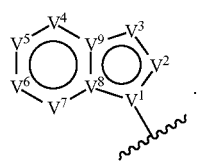

(e-1)

In certain embodiments, E is of Formula (e-2):

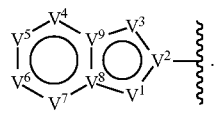

(e-2)

In certain embodiments, E is of Formula (e-3):

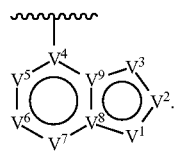

(e-3)

In certain embodiments, E is of Formula (e-4):

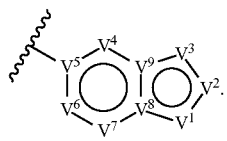

(e-4)

As used herein, each instance of $V^1, V^2, V^3, V^4, V^5, V^6, V^7, V^8$, and $V^9$ may independently be O, S, N, $NR^N$, C, or $CR^C$, as valency permits. In certain embodiments, $V^1$ is O, S, N or $NR^N$. In certain embodiments, $V^1$ is N or $NR^N$. In certain embodiments, $V^1$ is O. In certain embodiments, $V^1$ is S. In certain embodiments, only one of $V^1, V^2, V^3, V^4, V^5, V^6, V^7, V^8$, and $V^9$ is selected from the group consisting of O, S, N, and $NR^N$. In certain embodiments, only one of $V^1, V^2, V^3, V^4, V^5, V^6, V^7, V^8$, and $V^9$ is selected from the group consisting of N and $NR^N$. In certain embodiments, only one of $V^1, V^2, V^3, V^4, V^5, V^6, V^7, V^8$, and $V^9$ is O. In certain embodiments, only one of $V^1, V^2, V^3, V^4, V^5, V^6, V^7, V^8$, and $V^9$ is S. In certain embodiments, only two of $V^1, V^2, V^3, V^4, V^5, V^6, V^7, V^8$, and $V^9$ are each independently selected from the group consisting of O, S, N, and $NR^N$. In certain embodiments, only two of $V^1, V^2, V^3, V^4, V^5, V^6, V^7, V^8$, and $V^9$ are each independently selected from the group consisting of N and $NR^N$. In certain embodiments, only two of $V^1, V^2, V^3, V^4, V^5, V^6, V^7, V^8$, and $V^9$ are each independently selected from the group consisting of O, N and $NR^N$. In certain embodiments, only two of $V^1, V^2, V^3, V^4, V^5, V^6, V^7, V^8$, and $V^9$ are each independently selected from the group consisting of S, N and $NR^N$. In certain embodiments, only three of $V^1, V^2, V^3, V^4, V^5, V^6, V^7, V^8$, and $V^9$ are each independently selected from the group consisting of O, S, N, and $NR^N$. In certain embodiments, only three of $V^1, V^2, V^3, V^4, V^5, V^6, V^7, V^8$, and $V^9$ are each independently selected from the group consisting of N and $NR^N$. In certain embodiments, only three of $V^1, V^2, V^3, V^4, V^5, V^6, V^7, V^8$, and $V^9$ are each independently selected from the group consisting of O, N and $NR^N$. In certain embodiments, only three of $V^1, V^2, V^3, V^4, V^5, V^6, V^7, V^8$, and $V^9$ are each independently selected from the group consisting of S, N and $NR^N$. In certain embodiments, only four of $V^1, V^2, V^3, V^4, V^5, V^6, V^7, V^8$, and $V^9$ are each independently selected from the group consisting of O, S, N, and $NR^N$. In certain embodiments, only four of $V^1, V^2, V^3, V^4, V^5, V^6, V^7, V^8$, and $V^9$ are each independently selected from the group consisting of N and $NR^N$. In certain embodiments, only four of $V^1, V^2, V^3, V^4, V^5, V^6, V^7, V^8$, and $V^9$ are each independently selected from the group consisting of O, N and $NR^N$. In certain embodiments, only four of $V^1, V^2, V^3, V^4, V^5, V^6, V^7, V^8$, and $V^9$ are each independently selected from the group consisting of S, N and $NR^N$. In certain embodiments, only five of $V^1, V^2, V^3, V^4, V^5, V^6, V^7, V^8$, and $V^9$ are each independently selected from the group consisting of O, S, N, and $NR^N$. In certain embodiments, only five of $V^1, V^2, V^3, V^4, V^5, V^6, V^7, V^8$, and $V^9$ are each independently selected from the group consisting of N and $NR^N$.

In certain embodiments, E may also be an optionally substituted 5-membered heteroaryl ring. In certain embodiments, E is of Formula (e-5):

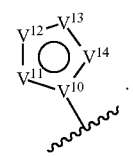

(e-5)

In compounds of Formula (e-5), $V^{10}, V^{11}, V^{12}, V^{13}$, and $V^{14}$ are each independently selected from the group consisting of O, S, N, $NR^N$, or $CR^C$, as valence permits. In certain embodiments, only one of $V^{10}, V^{11}, V^{12}, V^{13}$, and $V^{14}$ is selected from the group consisting of O, S, N, and $NR^N$. In certain embodiments, only two of $V^{10}, V^{11}, V^{12}, V^{13}$, and $V^{14}$ are selected from the group consisting of O, S, N, and $NR^N$. In certain embodiments, only three of $V^{10}, V^{11}, V^{12}, V^{13}$, and $V^{14}$ are selected from the group consisting of O, S, N, and $NR^N$. In certain embodiments, only four of $V^{10}, V^{11}, V^{12}, V^{13}$, and $V^{14}$ are selected from the group consisting of O, S, N, and $NR^N$.

In certain embodiments, E may also be an optionally substituted 6-membered heteroaryl ring. In certain embodiments, E is of Formula (e-6):

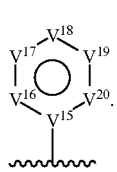

(e-6)

In compounds of Formula (e-6), $V^{15}$, $V^{16}$, $V^{17}$, $V^{18}$, $V^{19}$, and $V^{20}$ are each independently selected from the group consisting of O, S, N, $NR^N$, or $CR^C$, as valence permits. In certain embodiments, only one of $V^{15}$, $V^{16}$, $V^{17}$, $V^{18}V^{19}$, and $V^{20}$ is selected from the group consisting of O, S, N, and $NR^N$. In certain embodiments, only two of $V^{15}$, $V^{16}$, $V^{17}$, $V^{18}$, $V^{19}$, and $V^{20}$ are selected from the group consisting of O, S, N, and $NR^N$. In certain embodiments, only three of $V^{15}$, $V^{16}$, $V^{17}$, $V^{18}$, $V^{19}$, and $V^{20}$ are selected from the group consisting of O, S, N, and $NR^N$. In certain embodiments, only four of $V^{15}$, $V^{16}$, $V^{17}$, $V^{18}$, $V^{19}$, and $V^{20}$ are selected from the group consisting of O, S, N, and $NR^N$.

As defined generally above, $R^3$ is hydrogen, $C_{1-4}$ alkyl, or $C_{3-4}$ cycloalkyl. In certain embodiments, $R^3$ is hydrogen. In certain embodiments, $R^3$ is $C_{1-4}$ alkyl. In certain embodiments, $R^3$ is methyl, ethyl, propyl, butyl, or pentyl. In certain embodiments, $R^3$ is isopropyl, isobutyl, or isopentyl. In certain embodiments, $R^3$ is isobutyl. In certain embodiments, $R^3$ is $C_{3-4}$ cycloalkyl. In certain embodiments, $R^3$ is cyclopropyl. In certain embodiments, $R^3$ is cyclobutyl.

As defined generally above, $R^x$ is optionally substituted $C_{1-4}$ alkyl or optionally substituted $C_{3-4}$ cycloalkyl. In certain embodiments, $R^x$ is unsubstituted $C_{1-4}$ alkyl. In certain embodiments, $R^x$ is methyl. In certain embodiments, $R^x$ is ethyl. In certain embodiments, $R^x$ is isopropyl. In certain embodiments, $R^x$ is propyl. In certain embodiments, $R^x$ is butyl. In certain embodiments, $R^x$ is substituted $C_{1-4}$ alkyl. In certain embodiments, $R^x$ is $C_{1-4}$ alkyl substituted with hydroxyl or alkoxy. In certain embodiments, $R^x$ is hydroxyethyl or methoxyethyl. In certain embodiments, $R^x$ is optionally substituted $C_{3-4}$ cycloalkyl. In certain embodiments, $R^x$ is unsubstituted $C_{3-4}$ cycloalkyl. In certain embodiments, $R^x$ is substituted cyclopropyl. In certain embodiments, $R^x$ is unsubstituted cyclopropyl. In certain embodiments, $R^x$ is substituted cyclobutyl. In certain embodiments, $R^x$ is unsubstituted cyclobutyl.

As defined generally above, each instance of Cy is independently optionally substituted $C_{3-7}$ cycloalkyl, optionally substituted 4- to 7-membered heterocyclyl, optionally substituted aryl, optionally substituted heteroaryl. In some embodiments, Cy is optionally substituted $C_{3-7}$ cycloalkyl. In some embodiments, Cy is optionally substituted 4- to 7-membered heterocyclyl having 1-2 heteroatoms independently selected from nitrogen, oxygen, and sulfur. In some embodiments, Cy is oxetane, tetrahydrofuran, or tetrahydropyran. In some embodiments, Cy is optionally substituted aryl. In some embodiments, Cy is optionally substituted phenyl. In some embodiments, Cy is unsubstituted phenyl. In some embodiments, Cy is optionally substituted heteroaryl having 1-3 heteroatoms independently selected from nitrogen, oxygen, and sulfur. In some embodiments, Cy is optionally substituted 5- to 6-membered heteroaryl having 1-3 heteroatoms independently selected from nitrogen, oxygen, and sulfur. In some embodiments, Cy is pyridyl. In some embodiments, $R_2$ is

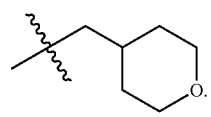

In some embodiments, $R_2$ is

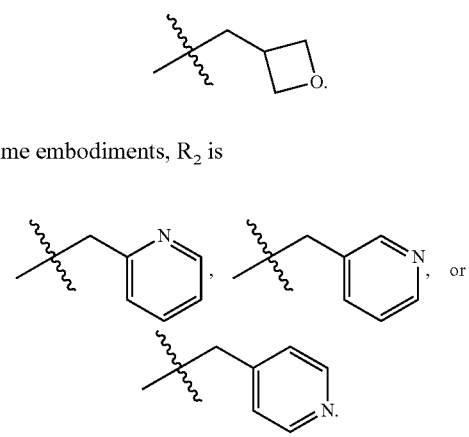

In some embodiments, $R_2$ is

As defined generally above, each instance of $R^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted aryl, optionally substituted heterocyclyl, optionally substituted heteroaryl, optionally substituted alkyl-Cy, an oxygen protecting group when attached to an oxygen atom, and a sulfur protecting group when attached to a sulfur atom. In certain embodiments, $R^C$ is hydrogen. In certain embodiments, $R^C$ is halogen. In certain embodiments, $R^C$ is substituted acyl. In certain embodiments, $R^C$ is unsubstituted acyl. In certain embodiments, $R^C$ is acetyl. In certain embodiments, $R^C$ is substituted acetyl. In certain embodiments, $R^C$ is substituted alkyl. In certain embodiments, $R^C$ is unsubstituted alkyl. In certain embodiments, $R^C$ is $C_{1-6}$ alkyl. In certain embodiments, $R^C$ is methyl. In certain embodiments, $R^C$ is ethyl. In certain embodiments, $R^C$ is propyl. In certain embodiments, $R^C$ is pentyl. In certain embodiments, $R^C$ is isopropyl, isobutyl, or isopentyl. In certain embodiments, $R^C$ is substituted alkenyl. In certain embodiments, $R^C$ is unsubstituted alkenyl. In certain embodiments, $R^C$ is vinyl. In certain embodiments, $R^C$ is substituted alkynyl. In certain embodiments, $R^C$ is unsubstituted alkynyl. In certain embodiments, $R^C$ is ethynyl. In certain embodiments, $R^C$ is substituted carbocyclyl. In certain embodiments, $R^C$ is unsubstituted carbocyclyl. In certain embodiments, $R^C$ is substituted heterocyclyl. In certain embodiments, $R^C$ is unsubstituted heterocyclyl. In certain embodiments, $R^C$ is substituted aryl. In certain embodiments, $R^C$ is of the formula (i):

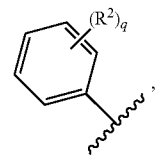

wherein R² and q are as defined herein. In certain embodiments, $R^C$ is unsubstituted aryl. In certain embodiments, $R^C$ is substituted phenyl. In certain embodiments, $R^C$ is unsubstituted phenyl. In certain embodiments, $R^C$ is substituted heteroaryl. In certain embodiments, $R^C$ is unsubstituted heteroaryl. In certain embodiments, $R^N$ is optionally substituted alkyl-Cy.

As defined generally above, each instance of $R^N$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, —SO$_2$N(R$^B$)$_2$, and a nitrogen protecting group. In certain embodiments, $R^N$ is substituted acyl. In certain embodiments, $R^N$ is unsubstituted acyl. In certain embodiments, $R^N$ is acetyl. In certain embodiments, $R^N$ is substituted acetyl. In certain embodiments, $R^N$ is substituted alkyl. In certain embodiments, $R^N$ is unsubstituted alkyl. In certain embodiments, $R^N$ is $C_{1-6}$ alkyl. In certain embodiments, $R^N$ is methyl. In certain embodiments, $R^N$ is ethyl. In certain embodiments, $R^N$ is propyl. In certain embodiments, $R^N$ is pentyl. In certain embodiments, $R^N$ is isopropyl, isobutyl, or isopentyl. In certain embodiments, $R^N$ is substituted alkenyl. In certain embodiments, $R^N$ is unsubstituted alkenyl. In certain embodiments, $R^N$ is vinyl. In certain embodiments, $R^N$ is substituted alkynyl. In certain embodiments, $R^N$ is unsubstituted alkynyl. In certain embodiments, $R^N$ is ethynyl. In certain embodiments, $R^N$ is substituted carbocyclyl. In certain embodiments, $R^N$ is unsubstituted carbocyclyl. In certain embodiments, $R^N$ is substituted heterocyclyl. In certain embodiments, $R^N$ is unsubstituted heterocyclyl. In certain embodiments, $R^N$ is substituted aryl. In certain embodiments, $R^N$ is of the formula (i):

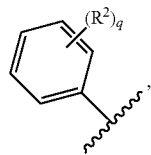

wherein R² and q are as defined herein. In certain embodiments, $R^N$ is unsubstituted aryl. In certain embodiments, $R^N$ is substituted phenyl. In certain embodiments, $R^N$ is unsubstituted phenyl. In certain embodiments, $R^N$ is substituted heteroaryl. In certain embodiments, $R^N$ is unsubstituted heteroaryl. In certain embodiments, $R^N$ is optionally substituted alkyl-Cy. In certain embodiments, $R^N$ is a nitrogen protecting group. In certain embodiments, $R^N$ is Bn, BOC, Cbz, Fmoc, trifluoroacetyl, triphenylmethyl, or Ts when attached to a nitrogen atom.

In certain embodiments, when the compound is of Formula (I), V is $CR^C$, X is N, Z is $NR^N$, and Y is $CR^C$; or V is $CR^C$, X is $NR^N$, Z is N, Y is $CR^C$; or V is $CR^C$, X is $CR^C$, Z is $NR^N$, Y is N; or V is $CR^C$, X is $CR^C$, Z is N, Y is $NR^N$; then each instance of $R^N$ is optionally substituted aryl or heteroaryl; and each instance of $R^C$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$.

In certain embodiments, when the compound is of Formula (I), V is $CR^C$, X is N, Z is $NR^N$, and Y is $CR^C$; or V is $CR^C$, X is $NR^N$, Z is N, Y is $CR^C$; or V is $CR^C$, X is $CR^C$, Z is $NR^N$, Y is N; or V is $CR^C$, X is $CR^C$, Z is N, Y is $NR^N$; then each instance of $R^C$ is independently selected from the group consisting of halogen, optionally substituted $C_{5-8}$ alkyl, optionally substituted alkenyl, optionally substituted alkynyl, optionally substituted $C_{5-8}$ cycloalkyl, optionally substituted acyl, optionally substituted aryl, or optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$; and each instance of $R^N$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —C(=O)R$^A$, —C(=O)OR$^A$, —C(=O)SR$^A$, —C(=O)N(R$^B$)$_2$, —C(=NR$^B$)R$^A$, —C(=NNR$^B$)R$^A$, —C(=NOR$^A$)R$^A$, —C(=NR$^B$)N(R$^B$)$_2$, —C(=S)R$^A$, —C(=S)N(R$^B$)$_2$, —S(=O)R$^A$, —SO$_2$R$^A$, —SO$_2$N(R$^B$)$_2$, and a nitrogen protecting group.

In certain embodiments, when the compound is of Formula (III), X is N, Z is $NR^N$, and Y is $CR^C$; or X is $NR^N$, Z is N, Y is $CR^C$; or X is $CR^C$, Z is $NR^N$, Y is N; or X is $CR^C$, Z is N, Y is $NR^N$; then each instance of $R^N$ is optionally substituted aryl or heteroaryl; and each instance of $R^C$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$.

In certain embodiments, when the compound is of Formula (III), X is N, Z is $NR^N$, and Y is $CR^C$; or X is $NR^N$, Z is N, Y is CR$^C$; or X is CR$^C$, Z is NR$^N$, Y is N; or X is CR$^C$, Z is N, Y is NR$^N$; then each instance of R$^C$ is independently selected from the group consisting of halogen, optionally substituted C$_{5-8}$ alkyl, optionally substituted alkenyl, optionally substituted alkynyl, optionally substituted C$_{5-8}$ cycloalkyl, optionally substituted acyl, optionally substituted aryl, or optionally substituted heteroaryl, optionally substituted alkyl-Cy, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$; and each instance of R$^N$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —C(=O)R$^A$, —C(=O)OR$^A$, —C(=O)SR$^A$, —C(=O)N(R$^B$)$_2$, —C(=NR$^B$)R$^A$, —C(=NNR$^B$)R$^A$, —C(=NOR$^A$)R$^A$, —C(=NR$^B$)N(R$^B$)$_2$, —C(=S)R$^A$, —C(=S)N(R$^B$)$_2$, —S(=O)R$^A$, —SO$_2$R$^A$, —SO$_2$N(R$^B$)$_2$, and a nitrogen protecting group.

As defined generally above, each instance of R$^A$ is independently selected from the group consisting of hydrogen, optionally substituted acyl, optionally substituted alkyl, optionally substituted alkenyl, optionally substituted alkynyl, optionally substituted carbocyclyl, optionally substituted carbocyclyl, optionally substituted aryl, optionally substituted heterocyclyl, optionally substituted heteroaryl, optionally substituted alkyl-Cy, an oxygen protecting group when attached to an oxygen atom, and a sulfur protecting group when attached to a sulfur atom. In certain embodiments, R$^A$ is hydrogen. In certain embodiments, R$^A$ is optionally substituted acyl. In certain embodiments, R$^A$ is optionally substituted alkyl. In certain embodiments, R$^A$ is optionally substituted C$_{1-6}$ alkyl. In certain embodiments, R$^A$ is substituted C$_{1-6}$ alkyl. In certain embodiments, R$^A$ is unsubstituted C$_{1-6}$ alkyl. In certain embodiments, R$^A$ is methyl, ethyl, propyl, butyl, pentyl, isopropyl, isobutyl, or isopentyl. In certain embodiments, R$^A$ is optionally substituted alkenyl. In certain embodiments, R$^A$ is optionally substituted alkynyl. In certain embodiments, R$^A$ is optionally substituted carbocyclyl. In certain embodiments, R$^A$ is optionally substituted aryl. In certain embodiments, R$^A$ is of the formula (i):

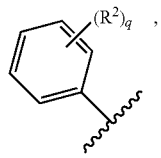

wherein R$^2$ and q are as defined herein. In certain embodiments, R$^A$ is optionally substituted heterocyclyl. In certain embodiments, R$^A$ is optionally substituted heteroaryl. In certain embodiments, R$^A$ is optionally substituted alkyl-Cy. In certain embodiments, R$^A$ is an oxygen protecting group. In certain embodiments, R$^A$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, As defined generally above, each instance of R$^B$ is independently selected from the group consisting of hydrogen, optionally substituted acyl, optionally substituted alkyl, optionally substituted alkenyl, optionally substituted alkynyl, optionally substituted carbocyclyl, optionally substituted aryl, optionally substituted heterocyclyl, optionally substituted heteroaryl, optionally substituted alkyl-Cy, and a nitrogen protecting group, or two R$^B$ groups are taken together with their intervening atoms to form an optionally substituted heterocyclic ring. In certain embodiments, R$^B$ is hydrogen. In certain embodiments, R$^B$ is optionally substituted acyl. In certain embodiments, R$^B$ is optionally substituted alkyl. In certain embodiments, R$^B$ is optionally substituted C$_{1-6}$ alkyl. In certain embodiments, R$^B$ is substituted C$_{1-6}$ alkyl. In certain embodiments, R$^B$ is unsubstituted C$_{1-6}$ alkyl. In certain embodiments, R$^B$ is methyl, ethyl, propyl, butyl, pentyl, isopropyl, isobutyl, or isopentyl. In certain embodiments, R$^B$ is optionally substituted alkenyl. In certain embodiments, R$^B$ is optionally substituted alkynyl. In certain embodiments, R$^B$ is optionally substituted carbocyclyl. In certain embodiments, R$^B$ is optionally substituted aryl. In certain embodiments, R$^B$ is of the formula (i):

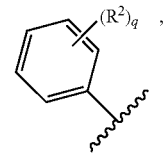

wherein R$^2$ and q are as defined herein. In certain embodiments, R$^B$ is optionally substituted heterocyclyl. In certain embodiments, R$^B$ is optionally substituted heteroaryl. In certain embodiments, R$^B$ is optionally substituted alkyl-Cy. In certain embodiments, R$^B$ is a nitrogen protecting group. In certain embodiments, two R$^B$ groups are taken together with their intervening atoms to form an optionally substituted heterocyclic ring.

As generally defined herein, q is 0, 1, 2, 3, 4, or 5. In certain embodiments, q is 0. In certain embodiments, q is 1 and Formula (i) is of the formula

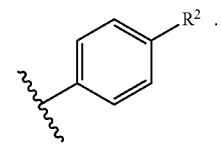

In certain embodiments, q is 1 and Formula (i) is of the formula

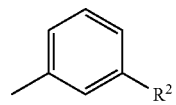

In certain embodiments, q is 1 and Formula (i) is of the formula

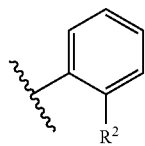

In certain embodiments, q is 2 and Formula (i) is of the formula

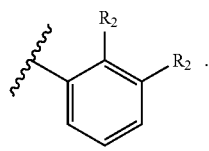

In certain embodiments, q is 2 and Formula (i) is of the formula

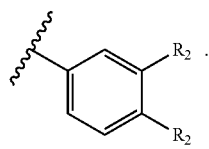

In certain embodiments, q is 2 and Formula (i) is of the formula

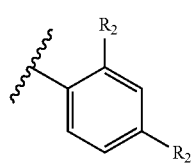

In certain embodiments, q is 2 and Formula (i) is of the formula

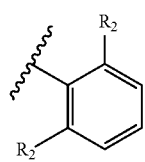

In certain embodiments, q is 2 and Formula (i) is of the formula

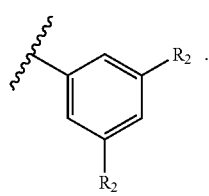

In certain embodiments, q is 2 and Formula (i) is of the formula

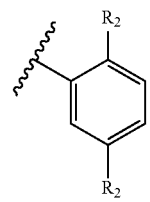

In certain embodiments, q is 3 and Formula (i) is of the formula

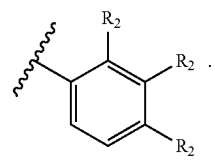

In certain embodiments, q is 3 and Formula (i) is of the formula

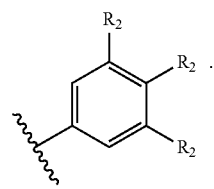

In certain embodiments, q is 3 and Formula (i) is of the formula

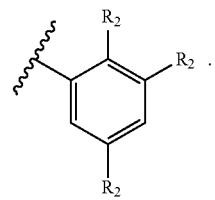

In certain embodiments, q is 3 and Formula (i) is of the formula

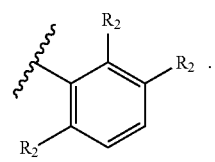

In certain embodiments, q is 3 and Formula (i) is of the formula

In certain embodiments, q is 3 and Formula (i) is of the formula

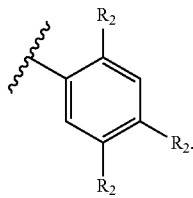

In certain embodiments, q is 4 and Formula (i) is of the formula

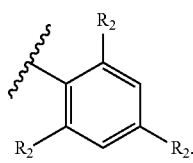

In certain embodiments, q is 4 and Formula (i) is of the formula

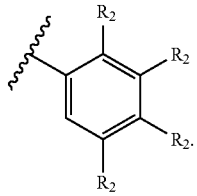

In certain embodiments, q is 4 and Formula (i) is of the formula

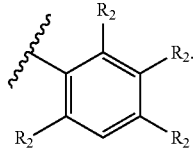

In certain embodiments, q is 5 and Formula (i) is of the formula

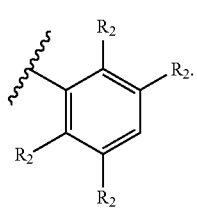

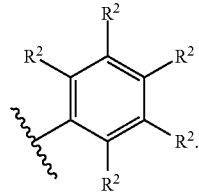

As described herein, each instance of $R^2$ is independently hydrogen, halogen, —$N_3$, —CN, —$NO_2$, optionally substituted alkyl, optionally substituted alkenyl, optionally substituted alkynyl, optionally substituted carbocyclyl, optionally substituted phenyl, optionally substituted heterocyclyl, optionally substituted heteroaryl, —$OR^A$, —$N(R^B)_2$, —$SR^A$, —C(=O)$R^A$, —C(=O)$OR^A$, —C(=O)$SR^A$, —C(=O)N($R^B)_2$, —C(=O)N($R^B$)N($R^B)_2$, —OC(=O)$R^A$, —OC(=O)N($R^B)_2$, —$NR^B$C(=O)$R^A$, —$NR^B$C(=O)N($R^B)_2$, —$NR^B$C(=O)N($R^B$)N($R^B)_2$, —$NR^B$C(=O)$OR^A$, —SC(=O)$R^A$, —C(=$NR^B$)$R^A$, —C(=$NNR^B$)$R^A$, —C(=$NOR^A$)$R^A$, —C(=$NR^B$)N($R^B)_2$, —$NR^B$C(=$NR^B$)$R^B$, —C(=S)$R^A$, —C(=S)N($R^B)_2$, —$NR^B$C(=S)$R^A$, —S(=O)$R^A$, —OS(O)$_2R^A$, —$SO_2R^A$, —$NR^B$$SO_2R^A$, or —$SO_2$N($R^B)_2$. In certain embodiments, $R^2$ is hydrogen. In some embodiments, $R^2$ is not hydrogen. In some embodiments, $R^2$ is halogen. In certain embodiments, $R^2$ is fluoro. In certain embodiments, $R^2$ is chloro. In some embodiments, $R^2$ is optionally substituted alkyl, optionally substituted alkenyl, optionally substituted alkynyl, or optionally substituted carbocyclyl. In certain embodiments, $R^2$ is optionally substituted $C_{1-6}$ alkyl, optionally substituted $C_{2-6}$ alkenyl, optionally substituted $C_{2-6}$ alkynyl, or optionally substituted $C_{3-6}$ carbocyclyl. In certain embodiments, $R^2$ is optionally substituted $C_{1-6}$ alkyl. In certain embodiments, $R^2$ is substituted $C_{1-6}$ alkyl. In certain embodiments, $R^2$ is —$CF_3$, $CHF_2$, or $CH_2F$. In certain embodiments, $R^2$ is —$C_{1-6}$ alkyl-carbocyclyl. In certain embodiments, $R^2$ is —$CH_2$-cyclopropyl or —$CH_2$-cyclobutyl. In certain embodiments, $R^2$ is unsubstituted $C_{1-6}$ alkyl. In certain embodiments, $R^2$ is methyl, ethyl, propyl, butyl, or pentyl. In certain embodiments, $R^2$ is isopropyl, isobutyl, or isopentyl. In certain embodiments, $R^2$ is isobutyl. In some embodiments, $R^1$ is —CN. In some embodiments, $R^2$ is optionally substituted carbocyclyl, optionally substituted phenyl, optionally substituted heterocyclyl, or optionally substituted heteroaryl. In some embodiments, $R^2$ is —$OR^A$, —$N(R^B)_2$, —$SR^A$, —C(=O)$R^A$, —C(O)$OR^A$, —C(O)$SR^A$, —C(O)N($R^B)_2$, —C(O)N($R^B$)N($R^B)_2$, —OC(O)$R^A$, —OC(O)N($R^B)_2$, —$NR^B$C(O)N($R^B)_2$, —$NR^B$C(O)N($R^B$)N($R^B)_2$, —$NR^B$C(O)$OR^A$, —SC(O)$R^A$, —C(=$NR^B$)$R^A$, —C(=$NNR^B$)$R^A$, —C(=$NOR^A$)$R^A$, —C(=$NR^B$)N($R^B)_2$, —$NR^B$C(=$NR^B$)$R^B$, —C(=S)$R^A$, C(=S)N($R^B)_2$, —$NR^B$C(=S)$R^A$, —S(O)$R^A$, —OS(O)$_2R^A$, —$SO_2R^A$, or —$SO_2$N($R^B)_2$. In certain embodiments, $R^2$ is —N($R^B)_2$. In certain embodiments, $R^2$ is —$NHR^B$. In certain embodiments, $R^2$ is —$NH_2$. In certain embodiments, $R^2$ is —$OR^A$. In certain embodiments, $R^2$ is —OH. In certain embodiments, $R^2$ is —$OR^A$, wherein $R^A$ is optionally substituted alkyl, optionally substituted alkenyl, optionally substituted alkynyl, or optionally substituted carbocyclyl. In certain embodiments, $R^2$ is —O-isobutylenyl. In certain embodiments, $R^2$ is —$OR^A$, wherein $R^A$ is optionally substituted $C_{1-6}$ alkyl. In certain embodiments, $R^2$ is $-OR^A$, wherein $R^A$ is unsubstituted $C_{1-6}$ alkyl. In certain embodiments, $R^2$ is —O-propyl, —O-isopropyl, —O-isobutyl, or —O-isopentyl. In certain embodiments, $R^2$ is $-OCH(CH_2CH_3)_2$. In certain embodiments, $R^2$ is $-OCH(OH)CH(CH_3)_2$. In certain embodiments, $R^2$ is $-OR^A$, wherein $R^A$ is substituted $C_{1-6}$ alkyl. In certain embodiments, $R^2$ is $-O-C_{1-6}$alkyl-O-$C_{1-6}$alkyl. In certain embodiments, $R^2$ is $-OCH_2CH_2OCH_3$, $-OCH_2CH_2CH_2OCH_3$, $-OCH_2CH_2OH$, or $-OCH_2CH_2OCH_2CH_2CH_3$. In certain embodiments, $R^2$ is $-OCH_2CF_3$ or $-OCH_2CH_2CH_2CF_3$. In certain embodiments, $R^2$ is $-OCH(CH_3)_2$, $-OCH_2CH(CH_3)_2$, $-OCH_2CH_2CH_3$, $-OCH_2CH_2CH(CH_3)_2$, $-OCH_2CH_2CH_2OCH_3$, or $-OCH_2CH_2OCH_3$. In certain embodiments, $R^2$ is $-O-C_{1-6}$alkyl-carbocyclyl. In certain embodiments, $R^2$ is $-O-CH_2$-cyclobutyl or $-O-CH_2$-cyclopropyl. In certain embodiments, $R^2$ is $-O-CH_2$-cyclopentyl or $-O-CH_2CH_2$-cyclohexyl. In certain embodiments, $R^2$ is $-O-C_{1-6}$alkyl-heterocyclyl. In certain embodiments, $R^2$ is $-O-CH_2$-tetrahydropyranyl or $-O-CH_2$-oxetanyl. In certain embodiments, $R^2$ is $-O-C_{1-6}$alkyl-aryl. In certain embodiments, $R^2$ is —O-benzyl or $-OCH_2CH_2Ph$. In certain embodiments, $R^2$ is $-O-C_{1-6}$alkyl-heteroaryl. In certain embodiments, $R^2$ is $-OR^A$, wherein $R^A$ is optionally substituted heterocyclyl. In certain embodiments, $R^2$ is —O-tetrahydropyranyl or —O-oxetanyl. In certain embodiments, $R^2$ is $-OR^A$, wherein $R^A$ is optionally substituted aryl. In certain embodiments, $R^2$ is —O-phenyl. In certain embodiments, $R^2$ is $-OR^A$, wherein $R^A$ is optionally substituted heteroaryl. In certain embodiments, $R^2$ is —O-pyridyl. In certain embodiments, $R^2$ is —O-2-pyridyl. In certain embodiments, $R^2$ is —O-3-pyridyl. In certain embodiments, $R^2$ is —O-4-pyridyl. In certain embodiments, $R^2$ is —O-pyrimidinyl.

In some embodiments, Formula (i) is selected from the group consisting of

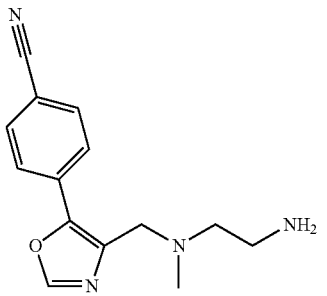 [SMILES: CN(CCN)Cc1ncoc1-c1ccc(C#N)cc1]

In certain embodiments, a provided compound is a compound listed in Table 1, or a pharmaceutically acceptable salt thereof.

TABLE 1

Exemplary Compounds

| Cmpd No | Structure |
|---|---|
| 1. | 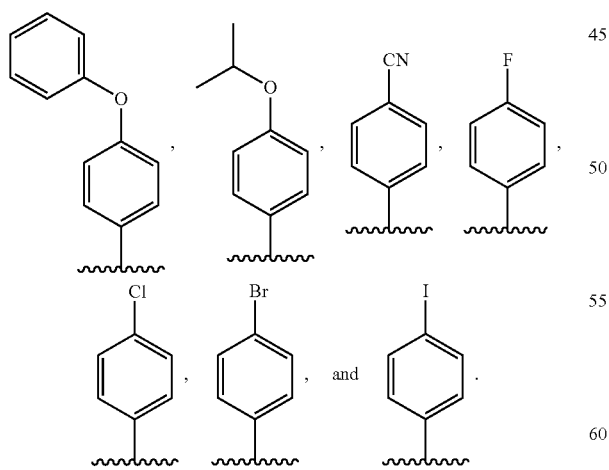 |
| 2. | 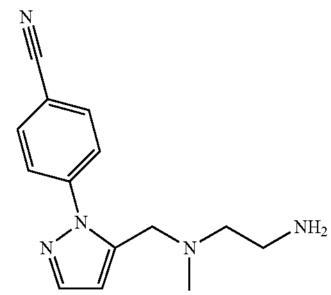 [SMILES: CN(CCN)Cc1ccnn1-c1ccc(C#N)cc1] |
| 3. | 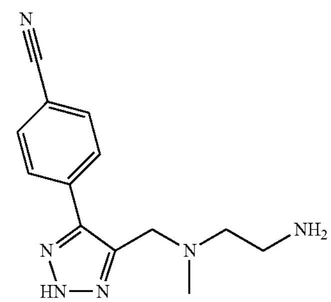 [SMILES: CN(CCN)Cc1n[nH]nc1-c1ccc(C#N)cc1] |
| 4. | 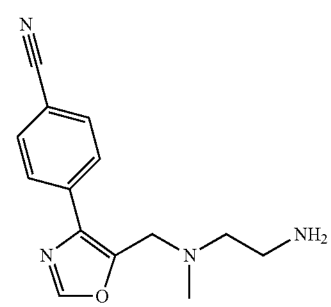 [SMILES: CN(CCN)Cc1ocnc1-c1ccc(C#N)cc1] |
| 5. | 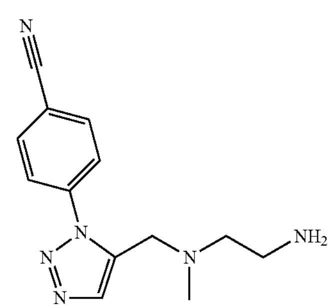 [SMILES: CN(CCN)Cc1cnnn1-c1ccc(C#N)cc1] |

TABLE 1-continued
Exemplary Compounds
| Cmpd No | Structure |
|---|---|
| 6. | 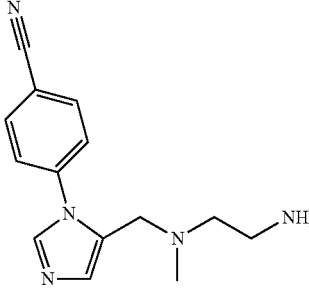 |
| 7. | 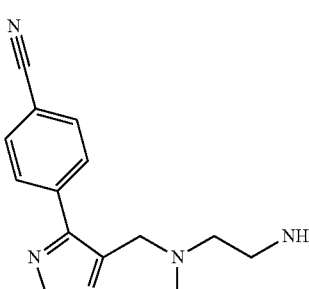 |
| 8. | 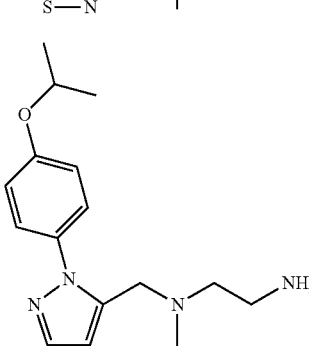 |
| 9. | 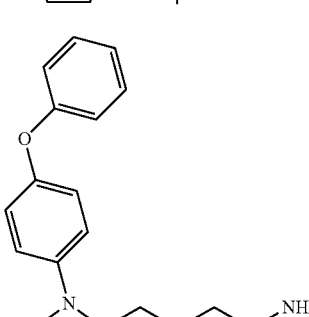 |
| 10. | 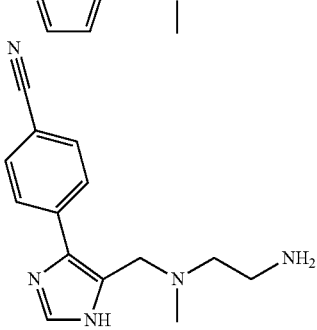 |
| 11. | 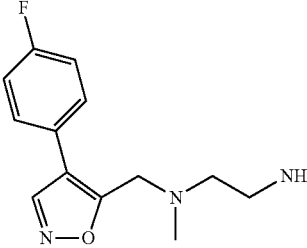 |
| 12. | 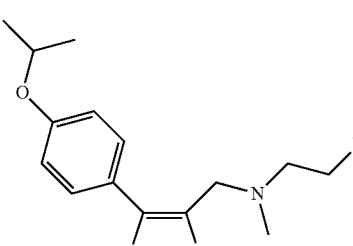 |
| 13. | 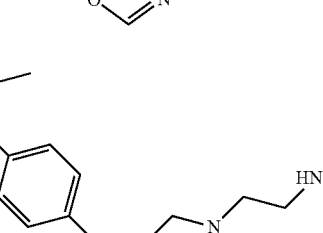 |
| 14. | 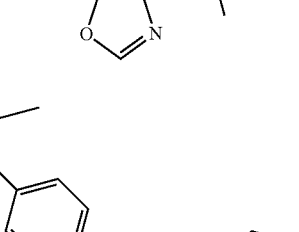 |
| 15. | 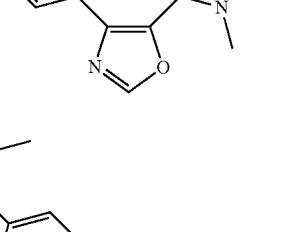 |
In certain embodiments, a provided compound inhibits an RMT (e.g., PRMT1, PRMT3, CARM1, PRMT6, and/or PRMT8). In certain embodiments, a provided compound inhibits wild-type PRMT1, PRMT3, CARM1, PRMT6, and/or PRMT8. In certain embodiments, a provided compound inhibits a mutant RMT. In certain embodiments, a provided compound inhibits PRMT1, PRMT3, CARM1, PRMT6, and/or PRMT8, e.g., as measured in an assay described herein. In certain embodiments, the RMT is from a human. In certain embodiments, a provided compound inhibits an RMT (e.g., PRMT1, PRMT3, CARM1, PRMT6, and/or PRMT8) at an $IC_{50}$ less than or equal to 10 µM. In certain embodiments, a provided compound inhibits an RMT (e.g., PRMT1, PRMT3, CARM1, PRMT6, and/or PRMT8) at an $IC_{50}$ less than or equal to 1 µM. In certain embodiments, a provided compound inhibits an RMT (e.g., PRMT1, PRMT3, CARM1, PRMT6, and/or PRMT8) at an $IC_{50}$ less than or equal to 0.1 µM. In certain embodiments, a provided compound inhibits an RMT (e.g., PRMT1, PRMT3, CARM1, PRMT6, and/or PRMT8) at an IC50 less than or equal to 0.01 µM. In certain embodiments, a provided compound inhibits an RMT (e.g., PRMT1, PRMT3, CARM1, PRMT6, and/or PRMT8) in a cell at an $EC_{30}$ less than or equal to 10 µM. In certain embodiments, a provided compound inhibits an RMT (e.g., PRMT1, PRMT3, CARM1, PRMT6, and/or PRMT8) in a cell at an $EC_{30}$ less than or equal to 12 µM. In certain embodiments, a provided compound inhibits an RMT (e.g., PRMT1, PRMT3, CARM1, PRMT6, and/or PRMT8) in a cell at an $EC_{30}$ less than or equal to 3 µM. In certain embodiments, a provided compound inhibits PRMT1 in a cell at an $EC_{30}$ less than or equal to 12 µM. In certain embodiments, a provided compound inhibits PRMT1 in a cell at an $EC_{30}$ less than or equal to 3 µM. In certain embodiments, a provided compound inhibits an RMT (e.g., PRMT1, PRMT3, CARM1, PRMT6, and/or PRMT8) in a cell at an $EC_{30}$ less than or equal to 1 µM. In certain embodiments, a provided compound inhibits an RMT (e.g., PRMT1, PRMT3, CARM1, PRMT6, and/or PRMT8) in a cell at an $EC_{30}$ less than or equal to 0.1 µM. In certain embodiments, a provided compound inhibits cell proliferation at an $EC_{50}$ less than or equal to 10 µM. In certain embodiments, a provided compound inhibits cell proliferation at an $EC_{50}$ less than or equal to 1 µM. In certain embodiments, a provided compound inhibits cell proliferation at an $EC_{50}$ less than or equal to 0.1 µM.

It will be understood by one of ordinary skill in the art that the RMT can be wild-type, or any mutant or variant.

The present disclosure provides pharmaceutical compositions comprising a compound described herein, e.g., a compound of Formula (I) or a pharmaceutically acceptable salt thereof, as described herein, and optionally a pharmaceutically acceptable excipient. It will be understood by one of ordinary skill in the art that the compounds described herein, or salts thereof, may be present in various forms, such as amorphous, hydrates, solvates, or polymorphs. In certain embodiments, a provided composition comprises two or more compounds described herein. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting an RMT (e.g., PRMT1, PRMT3, CARM1, PRMT6, and/or PRMT8). In certain embodiments, the effective amount is an amount effective for treating an RMT-mediated disorder (e.g., a PRMT1-, PRMT3-, CARM1-, PRMT6-, and/or PRMT8-mediated disorder). In certain embodiments, the effective amount is a prophylactically effective amount. In certain embodiments, the effective amount is an amount effective to prevent an RMT-mediated disorder.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

In some embodiments, a pharmaceutical composition described herein is sterilized.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol. Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. In certain embodiments, a compound or composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In certain embodiments, the additional therapeutically active agent is a compound of Formula (I). In certain embodiments, the additional therapeutically active agent is not a compound of Formula (I). In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, an additional therapeutically active agent is prednisolone, dexamethasone, doxorubicin, vincristine, mafosfamide, cisplatin, carboplatin, Ara-C, rituximab, azacitadine, panobinostat, vorinostat, everolimus, rapamycin, ATRA (all-trans retinoic acid), daunorubicin, decitabine, Vidaza, mitoxantrone, or IBET-151.

Also encompassed by the present discosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Compounds and compositions described herein are generally useful for the inhibition of RMT (e.g., PRMT1, PRMT3, CARM1, PRMT6, and/or PRMT8). In some embodiments, methods of treating an RMT-mediated disorder in a subject are provided which comprise administering an effective amount of a compound described herein (e.g., a compound of Formula (I)), or a pharmaceutically acceptable salt thereof), to a subject in need of treatment. In certain embodiments, the effective amount is a therapeutically effective amount. In certain embodiments, the effective amount is a prophylactically effective amount. In certain embodiments, the subject is suffering from a RMT-mediated disorder. In certain embodiments, the subject is susceptible to a RMT-mediated disorder.

As used herein, the term "RMT-mediated disorder" means any disease, disorder, or other pathological condition in which an RMT (e.g., PRMT1, PRMT3, CARM1, PRMT6, and/or PRMT8) is known to play a role. Accordingly, in some embodiments, the present disclosure relates to treating or lessening the severity of one or more diseases in which an RMT is known to play a role.

In some embodiments, the present disclosure provides a method of inhibiting an RMT comprising contacting the RMT with an effective amount of a compound described herein (e.g., a compound of Formula (I)), or a pharmaceutically acceptable salt thereof. The RMT may be purified or crude, and may be present in a cell, tissue, or subject. Thus, such methods encompass both inhibition of in vitro and in vivo RMT activity. In certain embodiments, the method is an in vitro method, e.g., such as an assay method. It will be understood by one of ordinary skill in the art that inhibition of an RMT does not necessarily require that all of the RMT be occupied by an inhibitor at once. Exemplary levels of inhibition of an RMT (e.g., PRMT1, PRMT3, CARM1, PRMT6, and/or PRMT8) include at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, and greater than 90% inhibition.

In some embodiments, provided is a method of inhibiting RMT activity in a subject in need thereof (e.g., a subject diagnosed as having an RMT-mediated disorder) comprising administering to the subject an effective amount of a compound described herein (e.g., a compound of Formula (I)), or a pharmaceutically acceptable salt thereof, or a pharmaceutical composition thereof.

In certain embodiments, provided is a method of modulating gene expression in a cell which comprises contacting a cell with an effective amount of a compound of Formula (I), or a pharmaceutically acceptable salt thereof. In certain embodiments, the cell is in culture in vitro. In certain embodiments, the cell is in an animal, e.g., a human. In certain embodiments, the cell is in a subject in need of treatment.

In certain embodiments, provided is a method of modulating transcription in a cell which comprises contacting a cell with an effective amount of a compound of Formula (I), or a pharmaceutically acceptable salt thereof. In certain embodiments, the cell is in culture in vitro. In certain embodiments, the cell is in an animal, e.g., a human. In certain embodiments, the cell is in a subject in need of treatment.

In certain embodiments, a method is provided of selecting a therapy for a subject having a disease associated with an RMT-mediated disorder or mutation comprising the steps of determining the presence of an RMT-mediated disorder or gene mutation in an RMT gene (e.g., a PRMT1, PRMT3, CARM1, PRMT6, and/or PRMT8 gene) or and selecting, based on the presence of an RMT-mediated disorder a gene mutation in the RMT gene a therapy that includes the administration of a provided compound. In certain embodiments, the disease is cancer.

In certain embodiments, a method of treatment is provided for a subject in need thereof comprising the steps of determining the presence of an RMT-mediated disorder or a gene mutation in the RMT gene and treating the subject in need thereof, based on the presence of a RMT-mediated disorder or gene mutation in the RMT gene with a therapy that includes the administration of a provided compound. In certain embodiments, the subject is a cancer patient.

In some embodiments, a compound provided herein is useful in treating a proliferative disorder, such as cancer. For example, while not being bound to any particular mechanism, protein arginine methylation by PRMTs is a modification that has been implicated in signal transduction, gene transcription, DNA repair and mRNA splicing, among others; and overexpression of PRMTs within these pathways is often associated with various cancers. Thus, compounds which inhibit the action of PRMTs, as provided herein, are effective in the treatment of cancer.

In some embodiments, compounds provided herein are effective in treating cancer through the inhibition of PRMT1. For example, PRMT1 overexpression has been observed in various human cancers, including, but not limited to, breast cancer, prostate cancer, lung cancer, colon cancer, bladder cancer, and leukemia. In one example, PRMT1 specifically deposits an asymmetric dimethylarginine (aDMA) mark on histone H4 at arginine 3 (H4R3me2a), and this mark is associated with transcription activation. In prostate cancer, the methylation status of H4R3 positively correlates with increasing tumor grade and can be used to predict the risk of prostate cancer recurrence (Seligson et al., Nature 2005 435, 1262-1266). Thus, in some embodiments, inhibitors of PRMT1, as described herein, are useful in treating cancers associated with the methylation status of H4R3, e.g., prostate cancer. Additionally, the methylarginine effector molecule TDRD3 interacts with the H4R3me2a mark, and overexpression of TDRD3 is linked to poor prognosis for the survival of patients with breast cancer (Nagahata et al., Cancer Sci. 2004 95, 218-225). Thus, in some embodiments, inhibitors of PRMT1, as described herein, are useful in treating cancers associated with overexpression of TDRD3, e.g., breast cancer, as inhibition of PRMT1 leads to a decrease in methylation of H4R3, thereby preventing the association of overexpressed TDRD3 with H4R3me2a. In other examples, PRMT1 is known to have non-histone substrates. For example, PRMT1, when localized to the cytoplasm, methylates proteins that are involved in signal transduction pathways, e.g., the estrogen receptor (ER). The expression status of ER in breast cancer is critical for prognosis of the disease, and both genomic and non-genomic ER pathways have been implicated in the pathogenesis of breast cancer. For example, it has been shown that PRMT1 methylates ERa, and that ERa methylation is required for the assembly of ERa with SRC (a proto-oncogene tyrosine-protein kinase) and focal adhesion kinase (FAK). Further, the silencing of endogenous PRMT1 resulted in the inability of estrogen to activate AKT. These results suggested that PRMT1-mediated ERa methylation is required for the activation of the SRC-PI3K-FAK cascade and AKT, coordinating cell proliferation and survival. Thus, hypermethylation of ERa in breast cancer is thought to cause hyperactivation of this signaling pathway, providing a selective survival advantage to tumor cells (Le Romancer et al., Mol. Cell 2008 31, 212-221; Le Romancer et al., Steroids 2010 75, 560-564). Accordingly, in some embodiments, inhibitors of PRMT1, as described herein, are useful in treating cancers associated with ERa methylation, e.g., breast cancer. In yet another example, PRMT1 has been shown to be involved in the regulation of leukemia development. For example, SRC-associated in mitosis 68 kDa protein (SAM68; also known as KHDRBS1) is a well-characterized PRMT1 substrate, and when either SAM68 or PRMT1 is fused directly to the myeloid/lymphoid leukemia (MLL) gene, these fusion proteins can activate MLL oncogenic properties, implying that the methylation of SAM68 by PRMT1 is a critical signal for the development of leukemia (Cheung et al., Nature Cell Biol. 2007 9, 1208-1215). Accordingly, in some embodiments, inhibitors of PRMT1, as described herein, are useful in treating cancers associated with SAM68 methylation, e.g., leukemia. In still another example, PRMT1 is implicated in leukemia development through its interaction with AE9a, a splice isoform of AML1-ETO (Shia et al., Blood 2012 119:4953-62). Knockdown of PRMT1 affects expression of certain AE9a-activated genes and suppresses AE9a's self-renewal capability. It has also been shown that AE9a recruits PRMT1 to AE9a activated gene promoters, which leads to increased H4 Arg3 methylation, H3 Lys9/14 acetylation, and transcription activated. Accordingly, in some embodiments, inhibitors of PRMT1, as described herein, are useful in treating cancers associated with AML1-ETO, e.g., leukemia. Thus, without being bound by any particular mechanism, the inhibition of PRMT1, e.g., by compounds described herein, is beneficial in the treatment of cancer.

In some embodiments, compounds provided herein are effective in treating cancer through the inhibition of PRMT3. In one example, the DAL1 tumor suppressor protein has been shown to interact with PRMT3 and inhibits its methyltransferase activity (Singh et al., Oncogene 2004 23, 7761-7771). Epigenetic downregulation of DAL1 has been reported in several cancers (e.g., meningiomas and breast cancer), thus PRMT3 is expected to display increased activity, and cancers that display DAL1 silencing may, in some aspects, be good targets for PRMT3 inhibitors, e.g., those described herein. Thus, without being bound by any particular mechanism, the inhibition of PRMT3, e.g., by compounds described herein, is beneficial in the treatment of cancer.

In some embodiments, compounds provided herein are effective in treating cancer through the inhibition of PRMT4, also known as CARM1. For example, PRMT4 levels have been shown to be elevated in castration-resistant prostate cancer (CRPC), as well as in aggressive breast tumors (Hong et al., *Cancer* 2004 101, 83-89; Majumder et al., *Prostate* 2006 66, 1292-1301). Thus, in some embodiments, inhibitors of PRMT4, as described herein, are useful in treating cancers associated with PRMT4 overexpression. PRMT4 has also been shown to affect ERa-dependent breast cancer cell differentiation and proliferation (Al-Dhaheri et al., *Cancer Res.* 2011 71, 2118-2128), thus in some aspects PRMT4 inhibitors, as described herein, are useful in treating ERa-dependent breast cancer by inhibiting cell differentiation and proliferation. In another example, PRMT4 has been shown to be recruited to the promoter of E2F1 (which encodes a cell cycle regulator) as a transcriptional co-activator (Frietze et al., *Cancer Res.* 2008 68, 301-306). Thus, PRMT4-mediated upregulation of E2F1 expression may contribute to cancer progression and chemoresistance as increased abundance of E2F1 triggers invasion and metastasis by activating growth receptor signaling pathways, which in turn promote an antiapoptotic tumor environment (Engelmann and Piitzer, *Cancer Res* 2012 72; 571). Accordingly, in some embodiments, the inhibition of PRMT4, e.g., by compounds provided herein, is useful in treating cancers associated with E2F1 upregulation. Thus, without being bound by any particular mechanism, the inhibition of PRMT4, e.g., by compounds described herein, is beneficial in the treatment of cancer.

In some embodiments, compounds provided herein are effective in treating cancer through the inhibition of PRMT6. For example, PRMT6 has been reported to be overexpressed in a number of cancers, e.g., bladder and lung cancer (Yoshimatsu et al., *Int. J. Cancer* 2011 128, 562-573). Thus, in some embodiments, the inhibition of PRMT6, by compounds provided herein, is useful in treating cancers associated with PRMT6 overexpression. In some aspects, PRMT6 is primarily thought to function as a transcriptional repressor, although it has also been reported that PRMT6 functions as a co-activator of nuclear receptors. For example, as a transcriptional repressor, PRMT6 suppresses the expression of thrombospondin 1 (TSP1; also known as THBS1; a potent natural inhibitor of angiogenesis and endothelial cell migration) and p21 (a natural inhibitor of cyclin dependent kinase), thereby contributing to cancer development and progression (Michaud-Levesque and Richard, *J. Biol. Chem.* 2009 284, 21338-21346; Kleinschmidt et al., *PLoS ONE* 2012 7, e41446). Accordingly, in some embodiments, the inhibition of PRMT6, by compounds provided herein, is useful in treating cancer by preventing the repression of THBs1 and/or p21. Thus, without being bound by any particular mechanism, the inhibition of PRMT6, e.g., by compounds described herein, is beneficial in the treatment of cancer.

In some embodiments, compounds provided herein are effective in treating cancer through the inhibition of PRMT8. For example, deep-sequencing efforts of cancer genomes (e.g., COSMIC) have revealed that of all the PRMTs, PRMT8 is reported to be the most mutated. Of 106 sequenced genomes, 15 carry mutations in the PRMT8 coding region, and nine of these result in an amino acid change (Forbes et al., *Nucleic Acids Res.* 2011 39, D945-D950). Because of its high rate of mutation in cancer, PRMT8 is thought to contribute to the initiation or progression of cancer. Thus, without being bound by any particular mechanism, the inhibition of PRMT8, e.g., by compounds described herein, is beneficial in the treatment of cancer.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLIJSLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (e.g., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, a compound provided herein is useful in treating diseases associated with increased levels of circulating asymmetric dimethylarginine (aDMA), e.g., cardiovascular disease, diabetes, kidney failure, renal disease, pulmonary disease, etc. Circulating aDMA is produced by the proteolysis of asymmetrically dimethylated proteins. PRMTs which mediate aDMA methylation include, e.g., PRMT1, PRMT3, PRMT4, PRMT6, and PRMT8. aDMA levels are directly involved in various diseases as aDMA is an endogenous competitive inhibitor of nitric oxide synthase (NOS), thereby reducing the production of nitric oxide (NO) (Vallance et al., *J. Cardiovasc. Pharmacol.* 1992 20(Suppl. 12): S60-2). NO functions as a potent vasodilator in endothelial vessels, and as such inhibiting its production has major consequences on the cardiovascular system. For example, since PRMT1 is a major enzyme that generates aDMA, the dysregulation of its activity is likely to regulate cardiovascular diseases (Boger et al., *Ann. Med.* 2006 38:126-36), and other pathophysiological conditions such as diabetes mellitus (Sydow et al., *Vasc. Med.* 2005 10(Suppl. 1):S35-43), kidney failure (Vallance et al., *Lancet* 1992 339:572-5), and chronic pulmonary diseases (Zakrzewicz et al., *BMC Pulm. Med.* 2009 9:5). Additionally, it has been demonstrated that the expression of PRMT1 and PRMT3 are increased in coronary heart disease (Chen et al., *Basic Res. Cardiol.* 2006 101:346-53). In another example, aDMA elevation is seen in patients with renal failure, due to impaired clearance of this metabolite from the circulation (Jacobi et al., *Am. J. Nephrol.* 2008 28:224-37). Thus, circulating aDMA levels is observed in many pathophysiological situations. Accordingly, without being bound by any particular mechanism, the inhibition of PRMTs, e.g., by compounds described herein, results in the decrease of circulating aDMA, which is beneficial in the treatment of diseases associated with increased levels of circulating aDMA, e.g., cardiovascular disease, diabetes, kidney failure, renal disease, pulmonary disease, etc. In certain embodiments, a compound described herein is useful for treating or preventing vascular diseases.

In some embodiments, a compound provided herein is useful in treating metabolic disorders. For example, PRMT1 has been shown to enhance mRNA levels of FoxO1 target genes in gluconeogenesis, which results in increased hepatic glucose production, and knockdown of PRMT1 promotes inhibition of FoxO1 activity and thus inhibition of hepatic gluconeogenesis (Choi et al., *Hepatology* 2012 56:1546-56). Additionally, genetic haploinsufficiency of Prmt1 has been shown to reduce blood glucose levels in mouse models. Thus, without being bound by any particular mechanism, the inhibition of PRMT1, e.g., by compounds described herein, is beneficial in the treating of metabolic disorders, such as diabetes. In some embodiments, a provided compound is useful in treating type I diabetes. In some embodiments, a provided compound is useful in treating type II diabetes.

In some embodiments, a compound provided herein is useful in treating muscular dystrophies. For example, PRMT1, as well as PRMT3 and PRMT6, methylate the nuclear poly(A)-binding protein (PABPN1) in a region located near its C-terminus (Perreault et al., *J. Biol. Chem.* 2007 282:7552-62). This domain is involved in the aggregation of the PABPN1 protein, and abnormal aggregation of this protein is involved in the disease oculopharyngeal muscular dystrophy (Davies et al., *Int. J. Biochem. Cell. Biol.* 2006 38:1457-62). Thus, without being bound by any particular mechanism, the inhibition of PRMTs, e.g., by compounds described herein, is beneficial in the treatment of muscular dystrophies, e.g., oculopharyngeal muscular dystrophy, by decreasing the amount of methylation of PABPN1, thereby decreasing the amount of PABPN1 aggregation.

CARM1 is also the most abundant PRMT expressed in skeletal muscle cells, and has been found to selectively control the pathways modulating glycogen metabolism, and associated AMPK (AMP-activated protein kinase) and p38 MAPK (mitogen-activated protein kinase) expression. See, e.g., Wang et al., Biochem (2012) 444:323-331. Thus, in some embodiments, inhibitors of CARM1, as described herein, are useful in treating metabolic disorders, e.g., for example skeletal muscle metabolic disorders, e.g., glycogen and glucose metabolic disorders. Exemplary skeletal muscle metabolic disorders include, but are not limited to, Acid Maltase Deficiency (Glycogenosis type 2; Pompe disease), Debrancher deficiency (Glycogenosis type 3), Phosphorylase deficiency (McArdle's; GSD 5), X-linked syndrome (GSD9D), Autosomal recessive syndrome (GSD9B), Tarui's disease (Glycogen storage disease VII; GSD 7), Phosphoglycerate Mutase deficiency (Glycogen storage disease X; GSDX; GSD 10), Lactate dehydrogenase A deficiency (GSD 11), Branching enzyme deficiency (GSD 4), Aldolase A (muscle) deficiency, β-Enolase deficiency, Triosephosphate isomerase (TIM) deficiency, Lafora's disease (Progressive myoclonic epilepsy 2), Glycogen storage disease (Muscle, Type 0, Phosphoglucomutase 1 Deficiency (GSD 14)), and Glycogenin Deficiency (GSD 15).

In some embodiments, a compound provided herein is useful in treating autoimmune disease. For example, several lines of evidence strongly suggest that PRMT inhibitors may be valuable for the treatment of autoimmune diseases, e.g., rheumatoid arthritis. PRMTs are known to modify and regulate several critical immunomodulatory proteins. For example, post-translational modifications (e.g., arginine methylation), within T cell receptor signaling cascades allow T lymphocytes to initiate a rapid and appropriate immune response to pathogens. Co-engagement of the CD28 costimulatory receptor with the T cell receptor elevates PRMT activity and cellular protein arginine methylation, including methylation of the guanine nucleotide exchange factor Vav1 (Blanchet et al., *J. Exp. Med.* 2005 202:371-377). PRMT inhibitors are thus expected to diminish methylation of the guanine exchange factor Vav1, resulting in diminished IL-2 production. In agreement, siRNA directed against PRMT5 was shown to both inhibit NFAT-driven promoter activity and IL-2 secretion (Richard et al., *Biochem J.* 2005 388:379-386). In another example, PRMT1 is known to cooperate with PRMT4 to enhance NFkB p65-driven transcription and facilitate the transcription of p65 target genes like TNFα (Covic et al., *Embo. J.* 2005 24:85-96). Thus, in some embodiments, PRMT1 and/or PRMT4 inhibitors, e.g., those described herein, are useful in treating autoimmune disease by decreasing the transcription of p65 target genes like TNFα. These examples demonstrate an important role for arginine methylation in inflammation. Thus, without being bound by any particular mechanism, the inhibition of PRMTs, e.g., by compounds described herein, is beneficial in the treatment of autoimmune diseases.

In some embodiments, a compound provided herein is useful in treating neurological disorders, such as amyotrophic lateral sclerosis (ALS). For example, a gene involved in ALS, TLS/FUS, often contains mutated arginines in certain familial forms of this disease (Kwiatkowski et al., *Science* 2009 323:1205-8). These mutants are retained in the cytoplasm, which is similar to reports documenting the role arginine methylation plays in nuclear-cytoplasmic shuffling (Shen et al., *Genes Dev.* 1998 12:679-91). This implicates PRMT, e.g., PRMT1, function in this disease, as it was demonstrated that TLS/FUS is methylated on at least 20 arginine residues (Rappsilber et al., *Anal. Chem.* 2003 75:3107-14). Thus, in some embodiments, the inhibition of PRMTs, e.g., by compounds provided herein, are useful in treating ALS by decreasing the amount of TLS/FUS arginine methylation.

In some embodiments, compounds of Formula (I) can be prepared using methods shown in Scheme 1. Scheme 1 shows that heteroaryl carboxaldehydes of general formula XXI first react with mono-Boc protected ethylenediamines XXII under reductive amination conditions (e.g. sodium cyanoborohydride and catalytic acid such as acetic acid) in an appropriate solvent (e.g. methanol) to give intermediates of general formula XXIII. Subsequent functional group modifications and deprotection of Boc give compounds of Formula (I).

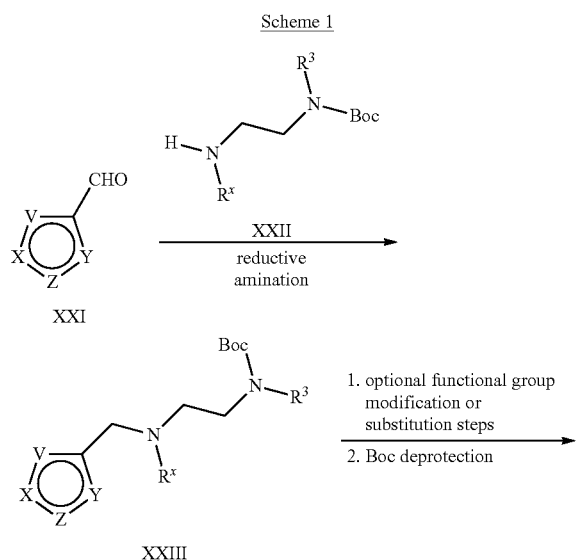

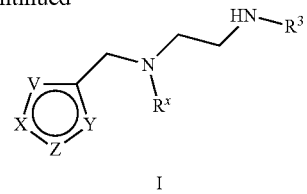

I

Carboxaldehydes of general formula XXI may be prepared from suitable known heteroaryl compound intermediates by established synthetic chemistry methods. Standard methods include, but are not limited to, direct introduction of the carboxaldehye through formylation (e.g. Vilsmeier reaction) and functional conversion of a suitable group such as a carboxylate as depicted in Scheme 2. As depicted in Scheme 2, methyl carboxylates intermediates of formula XXV are reduced (e.g. with Dibal or LiBH4) to corresponding hydroxymethyl intermediates of formula XXVI which are then subject to oxidation (e.g. with $MnO_2$ or IBX) to carboaldehyes of formula XXI.

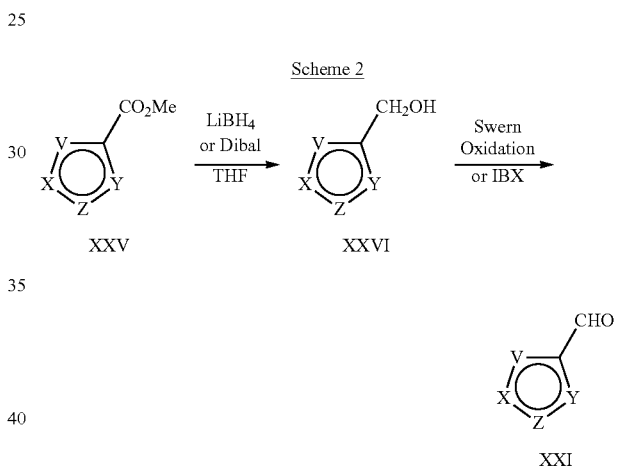

There are established methods for preparing the requisite heteroaryl carboxylates used in Scheme 2. In some embodiments, heteroaryl carboxylates can be synthesized by standard palladium catalyzed methoxy carbonylation of heteroaryl bromides as depicted in Scheme 3 with carbon monoxide and methanol in a pressurized autoclave at elevated temperature.

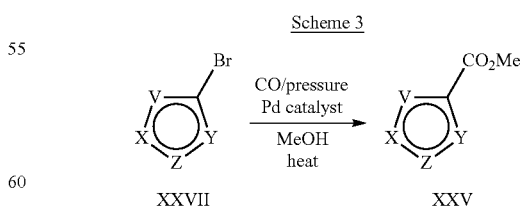

In some embodiments, the heteroaryl carboxylates can be synthesized from acyclic compounds containing a carboxylate group by known cycloaddition reactions. In certain embodiments, triazole carboxylates can be synthesise by [3+2]cycloaddition reaction of azides with alk-2-ynoates or 3-arylpropiolates. In certain embodiments, heteroaryl carboxylates can be prepared by standard stepwise heteroaryl ring synthesis methods. Heteroaryl carboxylates of formula XXVa, wherein V is $CR^C$ and $R^C$ is optionally substituted aryl or optionally substituted heteroaryl, can be prepared as depicted in Scheme 4. As shown in Scheme 4, heteroaryl bromide intermediates of general formula XXX, wherein X, Y and Z are independently O, S, N or $N(R^N)$ as valence permits, can be coupled with optionally substituted aryl or heteroaryl boronates or boronic acids under standard Suzuki reaction conditions to give heteroaryl carboxylates of formula XXVa.

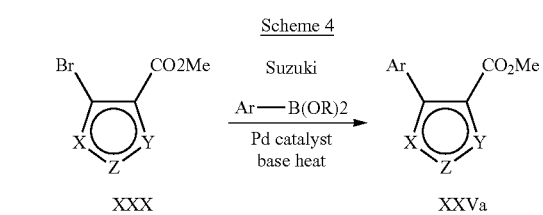

The mono-Boc protected ethylenediamines XXII can be synthesized by standard methods for derivatizing or preparing ethylenediamines. For example, intermediates of formula XXII may be prepared by treatment of the corresponding unprotected diamine precursors with $Boc_2O$ and purifying the mixture of mono and dibocylated products.

Oxazole compounds of general formula Xa, wherein L is a bond and E is an optionally substituted aryl group in compounds of general Formula (III-o), can be prepared as depicted in Scheme 5 from oxazole carboxylates of general formula XXVb using the methods described in Schemes 1 and 2.

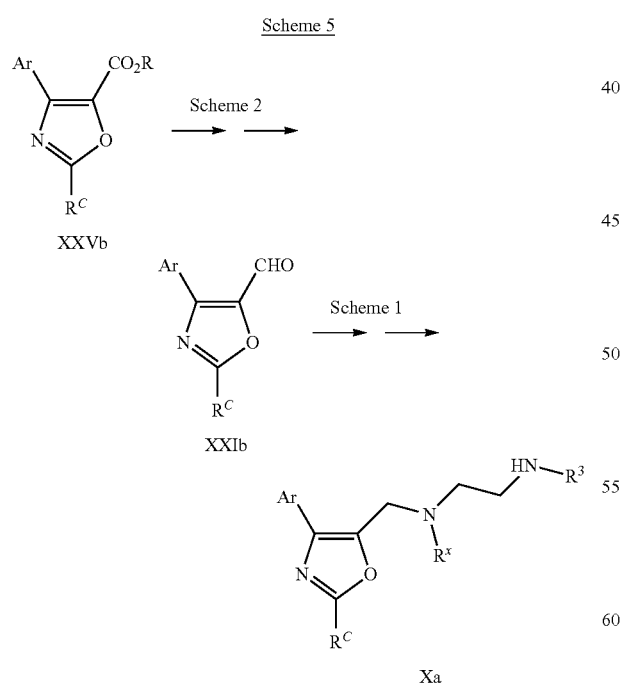

Oxazole carboxylates of general formula XXVb are known or can be prepared using the methods described in Schemes 3 and 4. Oxazole carboxylates of general formula XXVb wherein $R^C$ is hydrogen can be prepared by the oxazole ring synthesis method depicted in Scheme 6 from known or readily synthesized aromatic aldehydes (ArCHO).

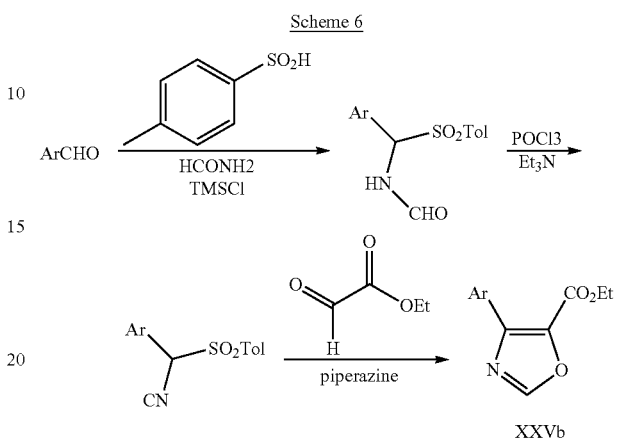

Oxazole compounds of general formula XIa wherein L is a bond and E is an optionally substituted aryl group in compounds of general formula Formula (III-n) can be prepared as depicted in Scheme 7 from oxazole carboxylates of general formula XLb using the methods described in Schemes 1 and 2.

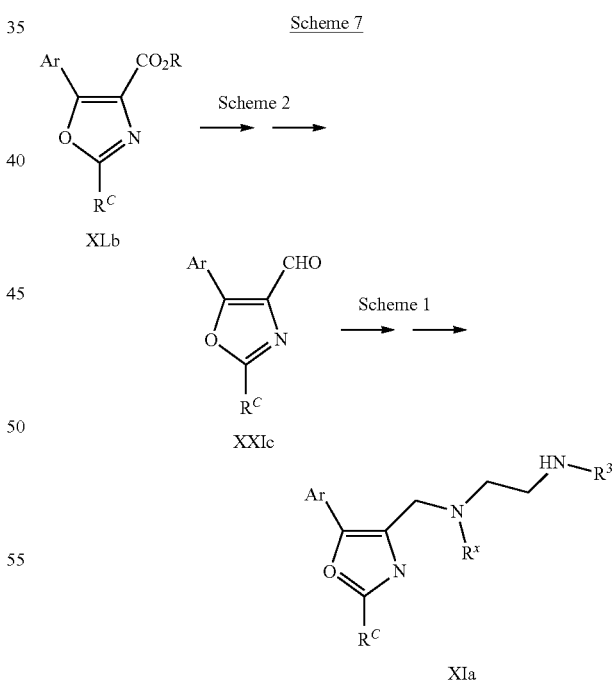

Oxazole carboxylates of general formula XLb are known or can be prepared using the methods described in Schemes 3 and 4. Oxazole carboxylates of general formula XLb wherein $R^C$ is hydrogen can be prepared by the oxazole ring synthesis method depicted in Scheme 8 by cyclocondensation of ethyl isocyanoacetate with known or readily synthesized aromatic acid chlorides (ArCOCl).

Scheme 8

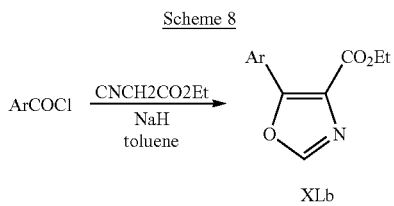

Pyrazole compounds of general Formula (II-a) can be prepared as depicted in Scheme 9 from pyrazole carboxaldehyde intermediates of general formula XXId wherein $R^N$, $R^1$, $R^3$ and $R^x$ are as described above.

Scheme 9

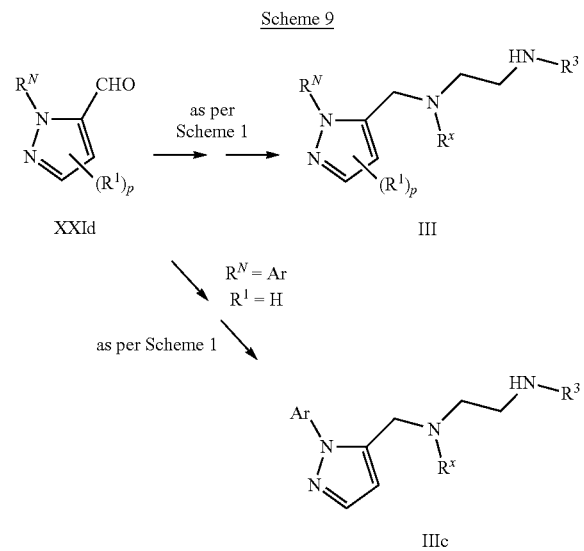

Using pyrazole carboxaldehydes of general formula XXIe where $R_1$ is H and $R^N$ is an optionally substituted aryl or heteroaryl group leads to corresponding compounds of formula IIIc. Pyrazole carboxaldehydes of formula XXIe can be synthesized as depicted in Scheme 10. Thus, reaction of optionally substituted aryl or heteroaryl hydrazines or the respective hydrochloride salts with 4,4-dimethoxy-3-oxobut-1-en-1-yl)dimethylamine in ethanol at reflux gives intermediates XXIe.

Scheme 10

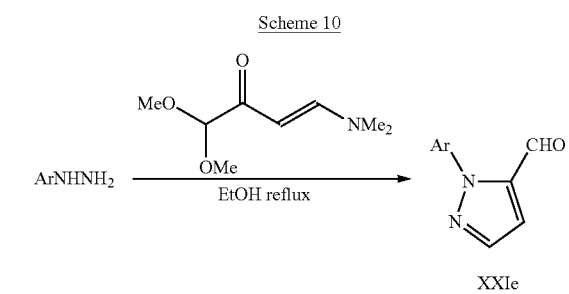

EXAMPLES

In order that the invention described herein may be more fully understood, the following examples are set forth. It should be understood that these examples are for illustrative purposes only and are not to be construed as limiting this invention in any manner.

Synthetic Methods

General methods and experimental procedures for preparing and characterizing compounds of the present invention are set forth below. Wherever needed, reactions were heated using conventional hotplate apparatus or heating mantle or microwave irradiation equipment. Reactions were conducted with or without stirring, under atmospheric or elevated pressure in either open or closed vessels. Reaction progress was monitored using conventional techniques such as TLC, HPLC, UPLC, or LCMS using instrumentation and methods described below. Reactions were quenched and crude compounds isolated using conventional methods as described in the specific examples provided. Solvent removal was carried out with or without heating, under atmospheric or reduced pressure, using either a rotary or centrifugal evaporator. Compound purification was carried out as needed using a variety of traditional methods including, but not limited to, preparative chromatography under acidic, neutral, or basic conditions using either normal phase or reverse phase HPLC or flash columns or Prep-TLC plates. Compound purity and mass confirmations were conducted using standard HPLC and/or UPLC and/or MS spectrometers and/or LCMS and/or GC equipment (e.g., including, but not limited to the following instrumentation: Waters Alliance 2695 with 2996 PDA detector connected with ZQ detector and ESI source; Shimadzu LDMS-2020; Waters Acquity H Class with PDA detector connected with SQ detector and ESI source; Agilent 1100 Series with PDA detector; Waters Alliance 2695 with 2998 PDA detector; AB SCIEX API 2000 with ESI source; Agilent 7890 GC). Exemplified compounds were dissolved in either MeOH or MeCN to a concentration of approximately 1 mg/mL and analyzed by injection of 0.5-10 μL into an appropriate LCMS system using the methods provided in the following table:

| Method | Column | Mobile Phase A | Mobile Phase B | Flow Rate (mL/min) | Gradient Profile | MS Heat Block Temp (°C.) | MS Detector Voltage (kV) |
|---|---|---|---|---|---|---|---|
| A | Shim-pack XR-ODS 2.2 μm 3.0 × 50 mm | Water/0.05% TFA | ACN/0.05% TFA | 1 | 5% to 100% B in 2.0 minutes, 100% B for 1.1 minutes, 100% to 5% B in 0.2 minutes, then stop | 250 | 1.5 |

-continued

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| B | Gemini-NX 3 μm C18 110A | Water/0.04% Ammonia | ACN | 1 | 5% to 100% B in 2.0 minutes, 100% B for 1.1 minutes, 100% to 5% B in 0.1 minutes, then stop | 200 | 0.75 |
| C | Shim-pack XR-ODS 1.6 μm 2.0 × 50 mm | Water/0.05% FA | ACN/0.05% FA | 1 | 5% to 100% B in 2.0 minutes, 100% B for 1.1 minutes, 100% to 5% B in 0.1 minutes, then stop | 250 | 0.85 |
| D | Shim-pack XR-ODS 2.2 μm 3.0 × 50 mm | Water/0.05% TFA | ACN/0.05% TFA | 1 | 5% to 100% B in 2.0 minutes, 100% B for 1.1 minutes, 100% to 5% B in 0.1 minutes, then stop | 250 | 0.95 |
| E | Waters Xselect C18 3.5 μm 3.0 × 50 mm | Water/0.05% FA | ACN/0.05% FA | 0.9 | 5% to 100% B in 2.0 minutes, 100% B for 1.2 minutes, 100% to 5% B in 0.1 minutes, then stop | 250 | 1.5 |
| F | Shim-pack XR-ODS 2.2 μm 3.0 × 50 mm | Water/0.05% TFA | ACN/0.05% TFA | 1 | 5% to 80% B in 3.25 minutes, 80% B for 1.35 minutes, 80% to 5% B in 0.3 minutes, then stop | 200 | 0.95 |
| G | Shim-pack XR-ODS 2.2 μm 3.0 × 50 mm | Water/0.05% TFA | ACN/0.05% TFA | 1 | 5% to 70% B in 2.50 minutes, 70% B for 0.70 minutes, 70% to 5% B in 0.1 minutes, then stop | 200 | 0.95 |
| H | Shim-pack XR-ODS 2.2 μm 3.0 × 50 mm | Water/0.05% TFA | ACN/0.05% TFA | 1 | 5% to 100% B in 2.20 minutes, 100% B for 1.00 minutes, 100% to 5% B in 0.1 minutes, then stop | 250 | 0.95 |
| I | Shim-pack XR-ODS 2.2 μm 3.0 × 50 mm | Water/0.05% TFA | ACN/0.05% TFA | 1 | 5% to 100% B in 1.20 minutes, 100% B for 1.00 minutes, 100% to 5% B in 0.1 minutes, then stop | 250 | 0.95 |
| J | Shim-pack XR-ODS 2.2 μm 3.0 × 50 mm | Water/0.05% TFA | ACN/0.05% TFA | 1 | 5% to 70% B in 3.20 minutes, 70% B for 0.75 minutes, 70% to 5% B in 0.35 minutes, then stop | 250 | 0.95 |
| K | Shim-pack XR-ODS 2.2 μm 3.0 × 50 mm | Water/0.05% TFA | ACN/0.05% TFA | 1 | 5% to 80% B in 3.00 minutes, 80% B for 0.8 minutes, 80% to 5% B in 0.1 minutes, then stop | 250 | 1.5 |

-continued

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| L | Shim-pack XR-ODS 2.2 µm 3.0 × 50 mm | Water/0.05% TFA | ACN/0.05% TFA | 1 | 5% to 100% B in 3.00 minutes, 100% B for 0.8 minutes, 100% to 5% B in 0.1 minutes, then stop | 250 | 1.5 |
| M | Shim-pack XR-ODS 2.2 µm 3.0 × 50 mm | Water/0.05% TFA | ACN/0.05% TFA | 1 | 5% to 100% B in 2.20 minutes, 100% B for 1.00 minutes, 100% to 5% B in 0.1 minutes, then stop | 250 | 1.5 |
| N | Shim-pack XR-ODS 2.2 µm 3.0 × 50 mm | Water/0.05% TFA | ACN/0.05% TFA | 1 | 5% to 80% B in 2.20 minutes, 80% B for 1.0 minutes, 80% to 5% B in 0.1 minutes, then stop | 250 | 1.5 |
| O | Zorbax Eclipse Plus C18 4.6 × 100 mm | Water/0.05% TFA | ACN/0.05% TFA | 1 | 5% to 70% B in 8.00 minutes, 70% B for 2.0 minutes, then stop | 250 | 1.5 |
| P | Shim-pack XR-ODS 2.2 µm 3.0 × 50 mm | Water/0.05% TFA | ACN/0.05% TFA | 1 | 5% to 65% B in 3.00 minutes, 65% B for 0.80 minutes, 100% to 5% B in 0.1 minutes, then stop | 250 | 1.5 |
| Q | Shim-pack XR-ODS 2.2 µm 3.0 × 50 mm | Water/0.05% TFA | ACN/0.05% TFA | 1 | 5% to 60% B in 2.50 minutes, 60% B for 0.7 minutes, 60% to 5% B in 0.1 minutes, then stop | 250 | 0.95 |
| R | Shim-pack XR-ODS 2.2 µm 3.0 × 50 mm | Water/0.05% TFA | ACN/0.05% TFA | 1 | 5% to 50% B in 2.50 minutes, 50% B for 0.7 minutes, 50% to 5% B in 0.1 minutes, then stop | 250 | 0.95 |
| S | XBridge C18 3.5 µm 3.0 × 50 mm | Water/0.05% TFA | ACN/0.05% TFA | 1 | 5% to 95% B in 2.20 minutes, 95% B for 1.00 minutes, 95% to 5% B in 0.1 minutes, then stop | 250 | 0.9 |
| T | Shim-pack XR-ODS 1.6 µm 2.0 × 50 mm | Water/0.05% FA | ACN/0.05% FA | 0.7 | 5% to 100% B in 2.0 minutes, 100% B for 1.1 minutes, 100% to 5% B in 0.1 minutes, then stop | 250 | 0.85 |
| U | Shim-pack XR-ODS 2.2 µm 3.0 × 50 mm | Water/0.05% TFA | ACN/0.05% TFA | 1 | 5% to 40% B in 2.50 minutes, 40% B for 0.7 minutes, 40% to 5% B in 0.1 minutes, then stop | 250 | 0.95 |

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| V | Shim-pack XR-ODS 2.2 μm 3.0 × 50 mm | Water/0.05% TFA | ACN/0.05% TFA | 1 | 5% to 60% B in 4.20 minutes, 60% B for 1.0 minutes, 60% to 5% B in 0.1 minutes, then stop | 200 | 1.05 |
| W | Shim-pack XR-ODS 2.2 μm 3.0 × 50 mm | Water/0.05% TFA | ACN/0.05% TFA | 1 | 5% to 100% B in 2.20 minutes, 100% B for 1.00 minutes, 100% to 5% B in 0.1 minutes, then stop | 200 | 0.95 |
| X | Shim-pack XR-ODS 1.6 μm 2.0 × 50 mm | Water/0.05% FA | ACN/0.05% FA | 0.7 | 5% to 100% B in 2.0 minutes, 100% B for 1.1 minutes, 100% to 5% B in 0.1 minutes, then stop | 200 | 0.85 |
| Y | Ecliplis Plus C18 3.5 μm 4.6 × 50 mm | Water/0.05% TFA | ACN | 1 | 5% to 100% B in 2.0 minutes, 100% B for 1.0 minutes, 100% to 5% B in 0.1 minutes, then stop | 250 | 1 |
| Z | Ecliplis Plus C18 3.5 μm 4.6 × 50 mm | Water/10 mM ammonium carbonate | ACN/5% water | 1 | 5% to 100% B in 2.0 minutes, 100% B for 1.0 minutes, 100% to 5% B in 0.1 minutes, then stop | 250 | 1.1 |
| A1 | Shim-pack XR-ODS 2.2 μm 3.0 × 50 mm | Water/0.05% TFA | ACN | 1 | 5% to 100% B in 2.0 minutes, 100% B for 1.0 minutes, 100% to 5% B in 0.1 minutes, then stop | 250 | 1 |
| A2 | Ecliplis Plus C18 3.5 μm 4.6 × 50 mm | Water/10 mM ammonium acetate | ACN | 1 | 5% to 100% B in 2.0 minutes, 100% B for 1.4 minutes, 100% to 5% B in 0.1 minutes, then stop | 250 | 0.95 |

Compound structure confirmations were carried out using standard 300 or 400 MHz NMR spectrometers with NOe's conducted whenever necessary.

The following abbreviations are used herein:
Abbreviation Meaning
ACN acetonitrile
atm. atmosphere
DCM dichloromethane
DHP dihydropyran
DIBAL diisobutyl aluminum hydride
DIEA diisopropyl ethylamine
DMF dimethyl formamide
DMF-DMA dimethyl formamide dimethyl acetal
DMSO dimethyl sulfoxide
dppf 1,1'-bis(diphenylphosphino)ferrocene
EA ethyl acetate
ESI electrospray ionization
EtOH ethanol
FA formic acid
GC gas chromatography
h hour
Hex hexanes
HMDS hexamethyl disilazide
HPLC high performance liquid chromatography
IPA isopropanol
LCMS liquid chromatography/mass spectrometry
MeOH methanol
min minutes
NBS N-bromo succinimide
NCS N-chloro succinimide
NIS N-iodo succinimide
NMR nuclear magnetic resonance
NOe nuclear Overhauser effect
Prep. preparative
PTSA para-toluene sulfonic acid
Rf retardation factor rt room temperature
RT retention time
sat. saturated
SGC silica gel chromatography
TBAF tetrabutyl ammonium fluoride
TEA triethylamine
TFA trifluoroacetic acid
THF tetrahydrofuran
TLC thin layer chromatography
UPLC ultra performance liquid chromatography Compound 1

4-(4-(((2-aminoethyl)(methyl)amino)methyl)oxazol-5-yl)benzonitrile

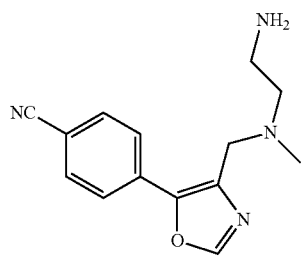 [SMILES: CN(CCN)Cc1ncoc1-c1ccc(C#N)cc1]

Step 1

4-cyanobenzoyl chloride

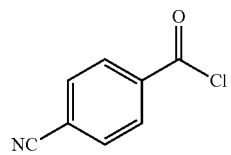 [SMILES: N#Cc1ccc(C(=O)Cl)cc1]

To a solution of 4-cyanobenzoic acid (5 g, 33.98 mmol, 1.00 equiv) in dichloromethane (50 mL) was added thionyl chloride (25 mL) dropwise with stirring. The resulting solution was refluxed for 4 h. The reaction mixture was cooled to room temperature and concentrated under vacuum to give 3 g of crude 4-cyanobenzoyl chloride as a brown solid. The crude was used in the next step without further purification.

Step 2 ethyl 5-(4-cyanophenyl)oxazole-4-carboxylate

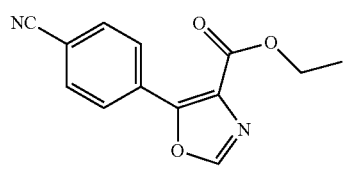 [SMILES: CCOC(=O)c1ncoc1-c1ccc(C#N)cc1]

A solution of ethyl 2-(methylideneamino)acetate (1.7 g, 14.77 mmol, 1.00 equiv) was added dropwise to a stirred mixture of sodium hydride (60%, 722 mg, 18.05 mmol, 1.22 equiv) in toluene (30 mL) at 5° C. The mixture was stirred at room temperature for 30 min. 4-cyanobenzoyl chloride (3 g, 18.12 mmol, 1.22 equiv) was then added dropwise at 5° C. The reaction was stirred at room temperature for 12 h then quenched with 30 mL of ice-water mixture. The resulting mixture was extracted with 2×15 mL of ethyl acetate. The combined organic layers was washed with 1×30 mL of brine, dried over anhydrous sodium sulfate and concentrated under vacuum. The residue was purified on a silica gel column eluted with 0-30% of ethyl acetate in petroleum ether to give 1.3 g (36%) of ethyl 5-(4-cyanophenyl)oxazole-4-carboxylate as a red solid. $^1$H-NMR (300 MHz, CDCl$_3$): δ 8.29-8.26 (m, 2H), 8.00 (s, 1H), 7.91-7.77 (m, 2H), 4.48-4.41 (m, 2H), 1.46-1.41 (t, J=7.2 Hz, 3H) ppm.

Step 3

4-(4-formyloxazol-5-yl)benzonitrile

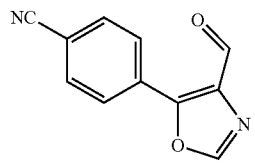 [SMILES: N#Cc1ccc(-c2ocnc2C=O)cc1]

To a solution of ethyl 5-(4-cyanophenyl)oxazole-4-carboxylate (500 mg, 2.06 mmol, 1.00 equiv) in anhydrous THF (10 mL) maintained under nitrogen at −78° C. was added dropwise a 25% solution of DIBAL (2.5 mL) in toluene with stirring. The resulting solution was stirred at −40° C. for 3 h and then quenched by the addition of 10 mL of water. The mixture was extracted with 2×10 mL of ethyl acetate. The combined organic layers was washed with 1×20 mL of brine, dried over anhydrous sodium sulfate and concentrated under vacuum. The residue was purified on a silica gel column eluted with 0-20% of ethyl acetate in petroleum ether to yield 350 mg (86%) of 4-(4-formyloxazol-5-yl)benzonitrile as a yellow solid. $^1$H-NMR (300 MHz, CDCl$_3$): δ 10.16 (s, 1H), 8.42 (d, J=8.4 Hz, 2H), 8.04 (s, 1H), 7.83 (d, J=8.4 Hz, 2H) ppm.

Step 4 tert-butyl 2-(((5-(4-cyanophenyl)oxazol-4-yl)methyl)(methyl)amino)ethyl)carbamate

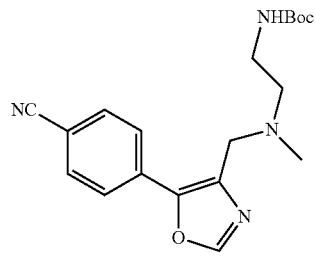 [SMILES: CN(CCNC(=O)OC(C)(C)C)Cc1ncoc1-c1ccc(C#N)cc1]

To a solution of 4-(4-formyloxazol-5-yl)benzonitrile (150 mg, 0.76 mmol, 1.00 equiv) and tert-butyl N-[2-(methylamino)ethyl]carbamate (131 mg, 0.75 mmol, 0.99 equiv) in 1,2-dichloroethane (5 mL) was added NaBH(OAc)$_3$ (321 mg, 1.51 mmol, 2.00 equiv). The resulting solution was stirred at room temperature overnight and then quenched with 10 mL of water. The mixture was extracted with 2×10 mL of ethyl acetate. The combined organic layers was dried over anhydrous sodium sulfate and concentrated under vacuum. The residue was purified on a silica gel column eluted with 0-30% of ethyl acetate in petroleum ether to afford 100 mg (37%) of tert-butyl 2-(((5-(4-cyanophenyl)oxazol-4-yl)methyl)(methyl)amino)ethyl)carbamate as a colorless oil. LCMS (method C, ESI): RT=0.75 min, m/z=357.0 [M+H]$^+$.

Step 5

Compound 1 4-(4-(((2-aminoethyl)(methyl)amino)methyl)oxazol-5-yl)benzonitrile

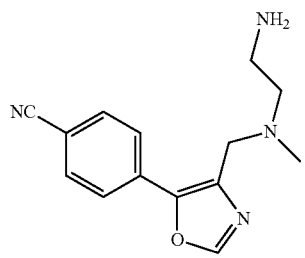 [SMILES: CN(CCN)Cc1ncoc1-c1ccc(C#N)cc1]

Hydrogen chloride gas was bubbled into a solution of tert-butyl 2-(((5-(4-cyanophenyl)oxazol-4-yl)methyl)(methyl)amino)ethyl)carbamate (100 mg, 0.28 mmol, 1.00 equiv) in dichloromethane (10 mL) maintained at −5 to 0° C. for 15 min. The resulting solution was stirred at 0° C. for 2 h and then concentrated under vacuum. The crude product was purified by Prep-HPLC with the following conditions (Prep-HPLC-016): Column, SunFire Prep C18 OBD Column, 5 µm, 19×150 mm, mobile phase: water with 10 mmol NH$_4$HCO$_3$ and MeCN (3.0% MeCN up to 20.0% in 10 min, up to 40.0% in 6 min, up to 95.0% in 1 min, hold 95.0% in 1 min, down to 3.0% in 2 min); Detector, UV 254/220 nm to give 27.2 mg (38%) of 4-(4-(((2-aminoethyl)(methyl)amino)methyl)oxazol-5-yl)benzonitrile as a light yellow oil. $^1$H-NMR (300 MHz, CDCl$_3$): δ 7.94-7.90 (m, 3H), 7.74 (d, J=8.4 Hz, 2H), 3.70 (s, 2H), 2.85 (t, J~5.8 Hz, 2H), 2.60 (t, J~5.8 Hz, 2H), 2.30 (s, 3H) ppm. LCMS (method H, ESI): RT=1.01 min, m/z=257.1 [M+H]$^+$.

Compound 2

4-(5-(((2-aminoethyl)(methyl)amino)methyl)-1H-pyrazol-1-yl)benzonitrile

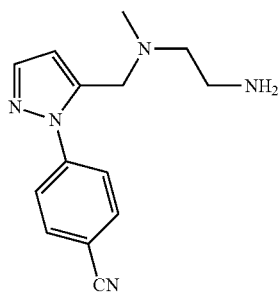 [SMILES: CN(CCN)Cc1ccnn1-c1ccc(C#N)cc1]

Step 1

(E)-4-(dimethylamino)-1,1-dimethoxybut-3-en-2-one

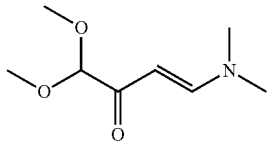

A solution of 1,1-dimethoxypropan-2-one (12 g, 101.58 mmol, 1.00 equiv) and (dimethoxymethyl)dimethylamine (12 g, 100.70 mmol, 0.99 equiv) was stirred at 100° C. for 5 h. The reaction mixture was cooled to room temperature and used in the next step directly. LCMS (method D, ESI): RT=0.94 min, m/z=174.0 [M+H]$^+$.

Step 2

4-(5-formyl-1H-pyrazol-1-yl)benzonitrile

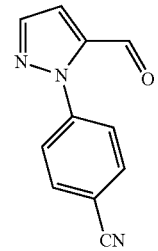 [SMILES: N#Cc1ccc(-n2nccc2C=O)cc1]

A solution of 4-hydrazinylbenzonitrile hydrochloride (10.14 g, 59.78 mmol, 1.00 equiv), (E)-4-(dimethylamino)-1,1-dimethoxybut-3-en-2-one (17.6 g, 101.61 mmol, 1.70 equiv), propan-2-one (30 mL) and 6N hydrochloric acid (30 mL) in ethanol (300 mL) was stirred at 78° C. for 3.5 h. The resulting mixture was cooled to room temperature and concentrated under vacuum. Water (300 mL) and ethyl acetate (200 mL) were added to dissolve the residue. The resulting mixture was extracted with ethyl acetate (2×200 mL). The combined organic layers was washed with water (1×100 mL) and brine (1×100 mL), dried over anhydrous sodium sulfate and concentrated under vacuum. The residue was purified on a silica gel column eluted with 0-20% of ethyl acetate in petroleum ether to give 4 g (34%) of 4-(5-formyl-1H-pyrazol-1-yl)benzonitrile as a yellow solid. $^1$H-NMR (300 MHz, CDCl$_3$): δ 9.87 (s, 1H), 8.09-7.98 (m, 3H), 7.85-7.83 (m, 2H), 7.36 (d, J=1.5 Hz, 1H) ppm. LCMS (method A, ESI): RT=1.28 min, m/z=198.0 [M+H]⁺.

Step 3 tert-butyl 2-(((1-(4-cyanophenyl)-1H-pyrazol-5-yl)methyl)(methyl)amino)ethyl)carbamate

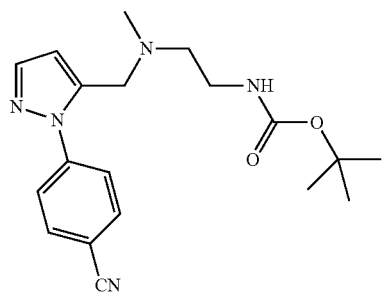 [SMILES: CN(CCNC(=O)OC(C)(C)C)Cc1ccnn1-c1ccc(C#N)cc1]

To a solution of 4-(5-formyl-1H-pyrazol-1-yl)benzonitrile (330 mg, 1.67 mmol, 1.00 equiv) and tert-butyl N-[2-(methylamino)ethyl]carbamate (321 mg, 1.84 mmol, 1.10 equiv) in methanol (50 mL) was added acetic acid (51 mg, 0.85 mmol, 0.51 equiv) to adjust the pH of the solution to 7. NaBH₃CN (214 mg, 3.41 mmol, 2.03 equiv) was added to the reaction mixture in a single portion. The resulting solution was stirred at 65° C. for 4 h. The reaction was cooled to room temperature and concentrated under vacuum. Water (20 mL) and ethyl acetate (20 mL) were added to dissolve the residue. The resulting mixture was extracted with ethyl acetate (3×20 mL). The organic layers were combined, dried over sodium sulfate and concentrated. The residue was purified on a silica gel column eluted with 0-25% of ethyl acetate in petroleum ether to yield 400 mg (67%) of tert-butyl 2-(((1-(4-cyanophenyl)-1H-pyrazol-5-yl)methyl)(methyl)amino)ethyl)carbamate as a yellow solid. ¹H-NMR (300 MHz, D₂O): δ 7.98-7.96 (m, 2H), 7.79 (d, J=8.7 Hz, 2H), 7.68 (s, 1H), 6.41 (s, 1H), 3.56 (s, 2H), 3.28-3.15 (m, 2H), 3.53-3.43 (m, 2H), 2.23 (s, 3H), 1.47 (s, 9H) ppm. LCMS (method D, ESI): RT=1.08 min, m/z=356.0 [M-2TFA+H]⁺.

Step 4

Compound 24-(5-(((2-aminoethyl)(methyl)amino)methyl)-1H-pyrazol-1-yl)benzonitrile

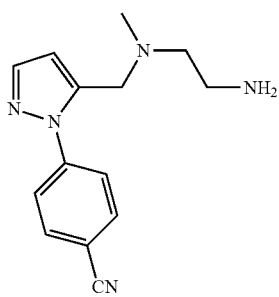 [SMILES: CN(CCN)Cc1ccnn1-c1ccc(C#N)cc1]

A solution of tert-butyl N-[2-([[1-(4-cyanophenyl)-1H-pyrazol-5-yl]methyl](methyl)amino)ethyl]carbamate (100 mg, 0.28 mmol, 1.00 equiv) in dichloromethane (5 mL) and trifluoroacetic acid (3 mL) was stirred at 25° C. for 30 min. The resulting mixture was concentrated under vacuum to give 196.2 mg (85%) of 4-(5-(((2-aminoethyl)(methyl)amino)methyl)-1H-pyrazol-1-yl)benzonitrile trifluoroacetate as a colorless oil. ¹H-NMR (300 MHz, D₂O): δ 7.94-7.91 (m, 2H), 7.80 (d, J=2.7 Hz, 1H), 7.61-7.58 (m, 2H), 6.78 (d, J=1.8 Hz, 1H), 4.52 (s, 2H), 3.30-3.18 (m, 4H), 2.57 (s, 3H) ppm. LCMS (method R, ESI): RT=1.18 min, m/z=256.1 [M+H]⁺.

Compound 3

4-(5-(((2-aminoethyl)(methyl)amino)methyl)-2H-1,2,3-triazol-4-yl)benzonitrile

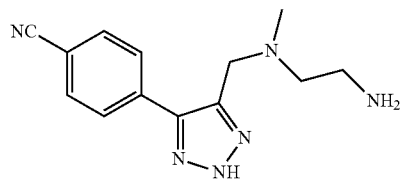 [SMILES: CN(CCN)Cc1n[nH]nc1-c1ccc(C#N)cc1]

Step 1 ethyl 3-(4-cyanophenyl)propiolate

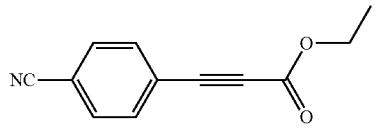

To a stirred solution of ethyl prop-2-ynoate (5.98 g, 60.96 mmol, 1.00 equiv) in anhydrous tetrahydrofuran (60 mL) maintained under nitrogen at −65° C. was added dropwise a 2.5M solution of n-BuLi (28 mL, 1.50 equiv) in hexanes. The reaction mixture was stirred at −65-40° C. for 1 h then a 0.7M solution of ZnCl₂ (170 mL, 2.00 equiv) in THF was added. The resulting solution was stirred at room temperature for 30 min. 4-iodobenzonitrile (6.87 g, 30.00 mmol, 0.50 equiv) was then added in portions followed by the addition of Pd(PPh₃)Cl₂ (1.05 g, 1.00 equiv). The resulting mixture was stirred at 50° C. for 5 h and then quenched by the addition of 150 mL of saturated NH₄Cl solution. The mixture was extracted with 3×100 mL of ether. The combined organic layers was dried over anhydrous sodium sulfate and concentrated under vacuum. The residue was purified on a silica gel column eluted with 0-10% of methanol in dichloromethane to give 3.25 g (27%) of ethyl 3-(4-cyanophenyl)propiolate as a white solid.

Step 2

4-(3-oxoprop-1-ynyl)benzonitrile

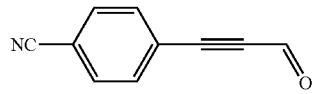

To a solution of ethyl 3-(4-cyanophenyl)propiolate (2.2 g, 11.04 mmol, 1.00 equiv) in dichloromethane (10 mL) maintained under nitrogen at −65° C. was added a 25% DIBAL (22 mL, 2.00 equiv) solution in toluene dropwise with stirring. The resulting solution was stirred at −65° C. for 2 h and then quenched by the addition of 5 mL of saturated sodium potassium tartrate solution. The solid material was removed by filtration. The filtrate was extracted with 3×30 mL of dichloromethane. The combined organic layers was dried over anhydrous sodium sulfate and concentrated under vacuum. The residue was purified on a silica gel column eluted with 0-10% of methanol in dichloromethane to give 627 mg (37%) of 4-(3-oxoprop-1-ynyl)benzonitrile as a white solid.

Step 3

4-(5-formyl-2H-1,2,3-triazol-4-yl)benzonitrile

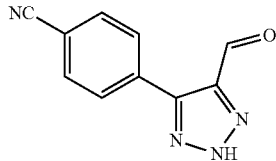 [SMILES: N#Cc1ccc(-c2n[nH]nc2C=O)cc1]

To a solution of 4-(3-oxoprop-1-ynyl)benzonitrile (500 mg, 3.22 mmol, 1.00 equiv) in DMSO (15 mL) was added NaN$_3$ (314 mg, 4.83 mmol, 1.50 equiv) in portions. The resulting solution was stirred at room temperature for 1 h and then quenched by the addition of 1 mL of water. The resulting mixture was concentrated under vacuum and the residue was purified on a C18 flash column eluted with 0-15% of acetonitrile in water to give 130 mg (20%) of 4-(5-formyl-2H-1,2,3-triazol-4-yl)benzonitrile as a light yellow solid. LCMS (method C, ESI), RT=0.93 min, m/z=199.0 [M+1]$^+$ Step 4 tert-butyl 2-(((5-(4-cyanophenyl)-2H-1,2,3-triazol-4-yl)methyl)(methyl)amino)ethyl)carbamate

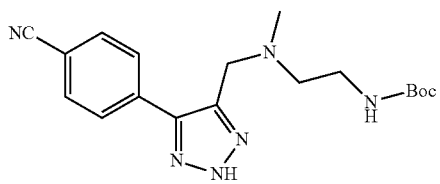 [SMILES: CN(CCNC(=O)OC(C)(C)C)Cc1n[nH]nc1-c1ccc(C#N)cc1]

A solution of 4-(5-formyl-2H-1,2,3-triazol-4-yl)benzonitrile (130 mg, 0.66 mmol, 1.00 equiv), DIEA (85 mg, 0.66 mmol, 1.00 equiv), tert-butyl N-[2-(methylamino)ethyl]carbamate (137 mg, 0.79 mmol, 1.20 equiv) and tetraisopropyl titanate (187 mg, 0.66 mmol, 1.00 equiv) in methanol (10 mL) was stirred at room temperature for 4 h. NaBH$_3$CN (42 mg, 0.67 mmol, 1.00 equiv) was then added and the reaction mixture was stirred at room temperature overnight. The resulting mixture was concentrated under vacuum to give 30 mg (13%) of crude tert-butyl 2-(((5-(4-cyanophenyl)-2H-1,2,3-triazol-4-yl)methyl)(methyl)amino)ethyl)carbamate as a white solid. LCMS (method A, ESI), RT=1.18 min, m/z=357.0 [M+1]$^+$ Step 5

Compound 34-(5-(((2-aminoethyl)(methyl)amino)methyl)-2H-1,2,3-triazol-4-yl)benzonitrile

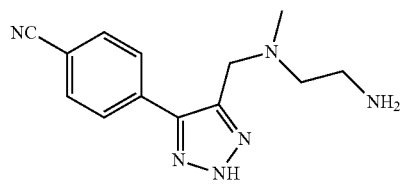 [SMILES: CN(CCN)Cc1n[nH]nc1-c1ccc(C#N)cc1]

Hydrogen chloride gas was bubbled into a solution of tert-butyl 2-(((5-(4-cyanophenyl)-2H-1,2,3-triazol-4-yl)methyl)(methyl)amino)ethyl)carbamate (30 mg, 0.08 mmol, 1.00 equiv) in 1,4-dioxane (4 mL) at 0° C. for 15 min. The reaction mixture was stirred at room temperature for 2 h and then concentrated under vacuum. The residue was partially purified on a silica gel column eluted with 0-10% of methanol in dichloromethane. The product was repurified by Pre-HPLC with the following conditions (1#-Pre-HPLC-005 (Waters)): Column, XBridge Shield RP18 OBD Column, 5 µm, 19×150 mm; mobile phase, water with 10 mmol NH$_4$HCO$_3$ and CH$_3$CN (18% CH$_3$CN up to 58% in 10 min, up to 95% in 1 min, down to 18% in 2 min); Detector, UV 254/220 nm to give 6.5 mg (30%) of 4-(5-(((2-aminoethyl)(methyl)amino)methyl)-2H-1,2,3-triazol-4-yl)benzonitrile as an off-white solid. $^1$H-NMR (300 MHz, DMSO-d6): δ 8.39 (s, 1H), 8.01 (d, J=8.4 Hz, 2H), 7.92 (d, J=8.4 Hz, 2H), 3.78 (s, 1H), 2.91-2.81 (m, 2H), 2.63-2.53 (m, 2H), 2.17 (s, 3H) ppm. LCMS (method P, ESI): RT=1.18 min, m/z=257.1 [M+1]$^+$.

Compound 4

4-(5-(((2-aminoethyl)(methyl)amino)methyl)oxazol-4-yl)benzonitrile

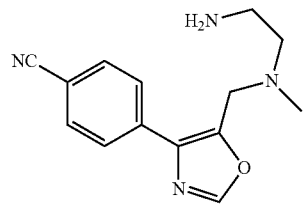 [SMILES: CN(CCN)Cc1ocnc1-c1ccc(C#N)cc1]

Step 1

N-((4-cyanophenyl)(tosyl)methyl)formamide

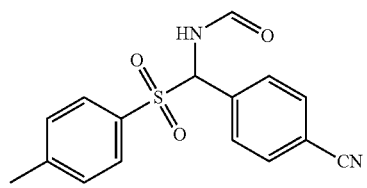 [SMILES: Cc1ccc(S(=O)(=O)C(NC=O)c2ccc(C#N)cc2)cc1]

A solution of 4-formylbenzonitrile (5.2 g, 39.65 mmol, 1.00 equiv), formamide (4.5 g, 99.91 mmol, 2.52 equiv), 4-methylbenzene-1-sulfinic acid (8.7 g, 55.70 mmol, 1.40 equiv) and chlorotrimethylsilane (6.5 g, 59.83 mmol, 1.51 equiv) in toluene (5 mL) and CH$_3$CN (5 mL) was stirred at 50° C. for 26 h. The resulting solution was diluted with 100 mL of water and then extracted with 3×50 mL of ethyl acetate. The organic layers were combined then washed with 3×50 mL of water and 2×50 mL of brine. It was then dried over anhydrous sodium sulfate and concentrated under vacuum to give 6 g of crude N-((4-cyanophenyl)(tosyl)methyl)formamide as a light brown solid.

Step 2

4-(isocyano(tosyl)methyl)benzonitrile

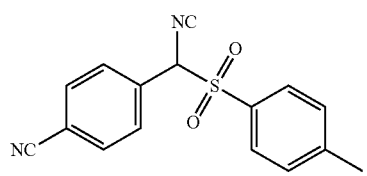

To a stirred solution of N-((4-cyanophenyl)(tosyl)methyl)formamide (3 g, 9.54 mmol, 1.00 equiv) in tetrahydrofuran (30 mL) at −10° C. was added dropwise phorphorus oxychloride (4.4 g, 28.70 mmol, 3.00 equiv) and TEA (4.8 g, 47.44 mmol, 5.00 equiv). The reaction mixture was stirred at room temperature for 3 h and then concentrated under vacuum. The residue was diluted with 100 mL of dichloromethane then washed with 3×50 mL of water and 2×50 mL of brine. The organic layer was dried over anhydrous sodium sulfate and concentrated under vacuum. The residue was purified on a silica gel column eluted with 0-30% of ethyl acetate in petroleum ether to give 1.5 g (53%) of 4-(isocyano(tosyl)methyl)benzonitrile as an off-white solid. $^1$H-NMR (300 MHz, DMSO-d6): δ 8.00-7.90 (m, 3H), 7.80-7.70 (m, 4H), 7.50-7.44 (m, 2H), 2.42 (s, 3H) ppm.

Step 3 ethyl 4-(4-cyanophenyl)oxazole-5-carboxylate

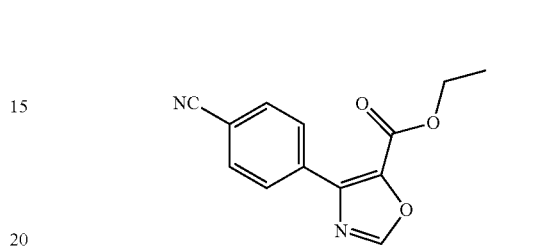

A solution of 4-(isocyano(tosyl)methyl)benzonitrile (1 g, 3.37 mmol, 1.00 equiv), ethyl 2-oxoacetate (1 g, 4.90 mmol, 1.45 equiv) and piperazine (500 mg, 5.80 mmol, 1.72 equiv) in tetrahydrofuran (20 mL) was stirred at room temperature overnight. The resulting mixture was concentrated under vacuum and the residue was purified on a silica gel column eluted with 0-30% of ethyl acetate in petroleum ether to afford 0.4 g (49%) of ethyl 4-(4-cyanophenyl)oxazole-5-carboxylate as a yellow solid. $^1$H-NMR (300 MHz, CDCl$_3$): δ 8.27-8.24 (m, 2H), 8.07 (s, 1H), 7.76-7.73 (m, 2H), 4.47-4.36 (m, 2H), 1.43-1.33 (m, 3H) ppm.

Step 4

4-(5-(hydroxymethyl)oxazol-4-yl)benzonitrile

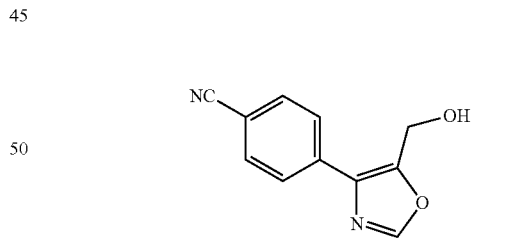

To a stirred solution of ethyl 4-(4-cyanophenyl)-1,3-oxazole-5-carboxylate (347 mg, 1.43 mmol, 1.00 equiv) in anhydrous THF (5 mL) maintained at −5° C. was added LiBH$_4$ (157 mg, 7.14 mmol, 4.98 equiv) in several portions. The resulting solution was stirred at room temperature for 3 h then quenched by the addition of 10 mL of saturated NH$_4$Cl solution. The mixture was extracted with 2×10 mL of ethyl acetate. The combined organic layers was dried over anhydrous sodium sulfate and concentrated under vacuum to give 190 mg (66%) of 4-(5-(hydroxymethyl)oxazol-4-yl)benzonitrile as a yellow solid. LCMS (method D, ESI): RT=1.13 min, m/z=201.0 [M+H]⁺.

Step 5

4-(5-formyloxazol-4-yl)benzonitrile

A mixture of 4-(5-(hydroxymethyl)oxazol-4-yl)benzonitrile (190 mg, 0.95 mmol, 1.00 equiv) and MnO₂ (1.9 g, 21.85 mmol, 23.03 equiv) in dichloromethane (5 mL) was refluxed for 2 h. The reaction mixture was cooled to room temperature and the solid material was removed by filtration. The filtrate was concentrated under vacuum and the residue was purified on a silica gel column eluted with 0-6% of ethyl acetate in petroleum ether to yield 20 mg (11%) of 4-(5-formyloxazol-4-yl)benzonitrile as a white solid. ¹H-NMR (300 MHz, CDCl₃): δ 10.02 (s, 1H), 8.90 (s, 1H), 8.25 (d, J=8.4 Hz, 1H), 8.08-8.02 (m, 2H) ppm.

Step 6 tert-butyl 2-(((4-(4-cyanophenyl)oxazol-5-yl)methyl)(methyl)amino)ethyl)carbamate

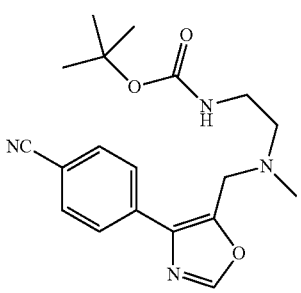 [SMILES: CN(CCNC(=O)OC(C)(C)C)Cc1ocnc1-c1ccc(C#N)cc1]

To a solution of 4-(5-formyloxazol-4-yl)benzonitrile (20 mg, 0.10 mmol, 1.00 equiv) and tert-butyl N-[2-(methylamino)ethyl]carbamate (21 mg, 0.12 mmol, 1.19 equiv) in 1,2-dichloroethane (3 mL) was added NaBH(OAc)₃ (45 mg, 0.21 mmol, 2.10 equiv). The resulting solution was stirred at room temperature for 2 h then quenched by the addition of 10 mL of saturated sodium bicarbonate solution. The mixture was extracted with 5 mL of dichloromethane. The organic layer was dried over anhydrous sodium sulfate and concentrated under vacuum to give 30 mg (83%) of tert-butyl 2-(((4-(4-cyanophenyl)oxazol-5-yl)methyl)(methyl)amino)ethyl) carbamate as a yellow oil. LCMS (method A, ESI): RT=1.13 min, m/z=357.0 [M+H]⁺.

Step 7

Compound 4 4-(5-(((2-aminoethyl)(methyl)amino)methyl)oxazol-4-yl)benzonitrile

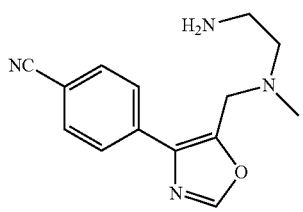 [SMILES: CN(CCN)Cc1ocnc1-c1ccc(C#N)cc1]

Hydrogen chloride gas was bubbled into a solution of tert-butyl 2-(((4-(4-cyanophenyl)oxazol-5-yl)methyl)(methyl)amino)ethyl)carbamate (30 mg, 0.08 mmol, 1.00 equiv) in dichloromethane (10 mL) at −5° C. The resulting solution was stirred at 0 to −5° C. for 2 h and then concentrated under vacuum. The crude product was purified by Prep-HPLC with the following conditions (2#-Waters 2767-2(HPLC-08)): Column, Xbridge Shield RP 18, 5 μm, 19×150 mm; mobile phase, water with 50 mmol NH₄HCO₃ and CH₃CN (10.0% CH₃CN up to 28.0% in 2 min, up to 46.0% in 10 min, up to 100.0% in 1 min, down to 10.0% in 1 min); Detector, UV 254 nm to give 4.5 mg (21%) of 4-(5-(((2-aminoethyl)(methyl)amino)methyl)oxazol-4-yl)benzonitrile as a light yellow oil. ¹H-NMR (300 MHz, CD₃OD): δ 8.31 (s, 1H), 7.98 (d, J=8.7 Hz, 2H), 7.86 (d, J=8.4 Hz, 2H), 4.02 (s, 2H), 3.08 (t, J~6 Hz, 2H), 2.78 (t, J~6 Hz, 2H), 2.36 (s, 3H) ppm. LCMS (method Q, ESI): RT=1.17 min, m/z=257.1 [M+H]⁺.

Compound 5

4-(5-(((2-aminoethyl)(methyl)amino)methyl)-1H-1,2,3-triazol-1-yl)benzonitrile

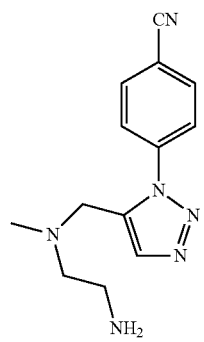

Step 1

4-azidobenzonitrile

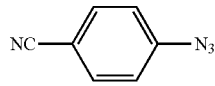

A solution of 4-fluorobenzonitrile (10.0 g, 82.57 mmol, 1.00 equiv) and NaN$_3$ (6.0 g, 92.29 mmol, 1.12 equiv) in DMSO (100 mL) was stirred at 100° C. for 2 h. The reaction was cooled to room temperature and then diluted with 700 mL of water. The precipitate was collected by filtration and air-dried to give 5.8 g (49%) of 4-azidobenzonitrile as a light yellow solid. $^1$H NMR (300 MHz, DMSO-d$_6$) δ: 7.88 (d, J=13.5 Hz, 2H), 7.31 (d, J=13.5 Hz, 2H) ppm.

Step 2 ethyl 3-(4-cyanophenyl)-3H-1,2,3-triazole-4-carboxylate

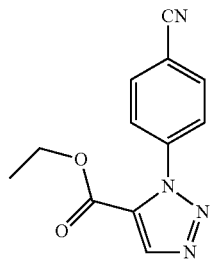 [SMILES: CCOC(=O)c1cnnn1-c1ccc(C#N)cc1]

A solution of 4-azidobenzonitrile (5.3 g, 36.77 mmol, 1.00 equiv) and ethyl prop-2-ynoate (10.82 g, 110.30 mmol, 3.00 equiv) in ethanol (160 mL) was stirred at room temperature overnight. The reaction mixture was concentrated under vacuum and the residue was purified on a silica gel column eluted with 0-20% of ethyl acetate in petroleum ether to give 650 mg (7%) of ethyl 1-(4-cyanophenyl)-1H-1,2,3-triazole-5-carboxylate as a white solid. $^1$H NMR (400 MHz, DMSO-d$_6$) δ: 8.54 (s, 1H), 8.11 (d, J=8.0 Hz, 2H), 7.90 (d, J=8.0 Hz, 2H), 4.27-4.22 (m, 2H), 1.20 (t, J=6.8 Hz, 3H) ppm. LCMS (method C, ESI): RT=0.87 min, m/z=243.1 [M+H]$^+$ and 2.4 g (26%) of ethyl 1-(4-cyanophenyl)-1H-1,2,3-triazole-4-carboxylate as a white solid. $^1$H NMR (400 MHz, DMSO-d$_6$) δ: 9.66 (s, 1H), 8.24 (d, J=8.8 Hz, 2H), 8.13 (d, J=8.8 Hz, 2H), 4.41-4.36 (m, 2H), 1.36 (t, J=7.2 Hz, 3H) ppm. LCMS (method D, ESI): RT=1.71 min, m/z=243.1 [M+H]$^+$.

Step 3

4-(5-(hydroxymethyl)-1H-1,2,3-triazol-1-yl)benzonitrile

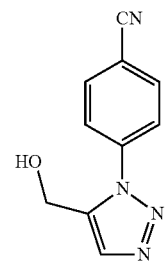

To a solution of ethyl 1-(4-cyanophenyl)-1H-1,2,3-triazole-5-carboxylate (650 mg, 2.68 mmol, 1.00 equiv) in THF (15 mL) at 0° C. was added LiBH$_4$ (177.3 mg, 8.06 mmol, 3.00 equiv) in portions. The resulting solution was stirred at room temperature for 3 h and then quenched with 100 mL of saturated NH$_4$Cl solution. The mixture was extracted with 3×100 mL of ethyl acetate. The combined organic layers was dried over anhydrous sodium sulfate and concentrated under vacuum. The residue was purified on a silica gel column eluted with 0-50% of ethyl acetate in petroleum ether to give 200 mg (37%) of 4-[5-(hydroxymethyl)-1H-1,2,3-triazol-1-yl]benzonitrile as a white solid. $^1$H NMR (400 MHz, DMSO-d$_6$) δ: 8.12 (d, J=8.0 Hz, 2H), 7.96 (d, J=8.0 Hz, 2H), 7.90 (s, 1H), 5.60 (t, J=5.2 Hz, 1H), 4.65 (d, J=5.2 Hz, 2H) ppm. LCMS (method A, ESI): RT=1.07 min, m/z=201.0 [M+H]$^+$.

Step 4

4-(5-formyl-1H-1,2,3-triazol-1-yl)benzonitrile

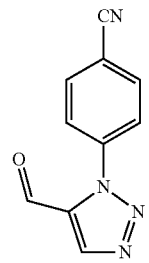 [SMILES: N#Cc1ccc(-n2nncc2C=O)cc1]

A mixture of 4-[5-(hydroxymethyl)-1H-1,2,3-triazol-1-yl]benzonitrile (225 mg, 1.12 mmol, 1.00 equiv) and MnO$_2$ (1958 mg, 22.52 mmol, 20.04 equiv) in dichloromethane (20 mL) was stirred at room temperature overnight. The solid material was removed by filtration. The filtrate was concentrated under vacuum and the residue was purified on a silica gel column eluted with 0-50% of ethyl acetate in petroleum ether to give 110 mg (49%) of 4-(5-formyl-1H-1,2,3-triazol-1-yl)benzonitrile as a white solid. $^1$H NMR (400 MHz, DMSO-d$_6$) δ: 9.96 (s, 1H), 8.70 (s, 1H), 8.15 (d, J=8.0 Hz, 2H), 7.97 (d, J=8.0 Hz, 2H) ppm.

Step 5 tert-butyl 2-(((3-(4-cyanophenyl)-3H-1,2,3-triazol-4-yl)methyl)(methyl)amino)ethyl)carbamate

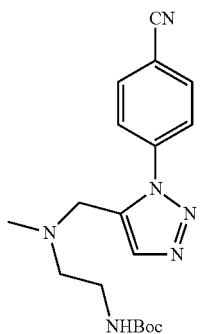 [SMILES: CN(CCNC(=O)OC(C)(C)C)Cc1cnnn1-c1ccc(C#N)cc1]

To a stirred solution of 4-(5-formyl-1H-1,2,3-triazol-1-yl) benzonitrile (110 mg, 0.56 mmol, 1.00 equiv) and tert-butyl N-[2-(methylamino)ethyl]carbamate (116 mg, 0.67 mmol, 1.20 equiv) in 1,2-dichloroethane (2 mL) was added NaBH(OAc)$_3$ (353.3 mg, 1.67 mmol, 3.00 equiv) in portions. The resulting mixture was stirred overnight at room temperature and then quenched by the addition of 20 mL of saturated NH$_4$Cl solution. The mixture was extracted with 3×50 mL of ethyl acetate. The combined organic layers was dried over anhydrous sodium sulfate and concentrated under vacuum. The residue was purified on a silica gel column eluted with 0-30% of ethyl acetate in petroleum ether to afford 100 mg (51%) of tert-butyl 2-(((3-(4-cyanophenyl)-3H-1,2,3-triazol-4-yl)methyl)(methyl)amino)ethyl)carbamate as a colorless oil. $^1$H NMR (300 MHz, DMSO-d$_6$) δ: 7.91 (d, J=9.0 Hz, 2H), 7.81 (d, J=9.0 Hz, 2H), 7.69 (s, 1H), 4.60 (s, 1H), 3.54 (s, 2H), 3.15 (t, J=5.4 Hz, 2H), 2.46 (t, J=5.4 Hz, 2H), 2.16 (s, 3H), 1.39 (s, 9H) ppm. LCMS (method C, ESI): RT=0.76 min, m/z=357.2 [M+H]$^+$.

Step 6

Compound 5: 4-(5-(((2-aminoethyl)(methyl)amino)methyl)-1H-1,2,3-triazol-1-yl)benzonitrile

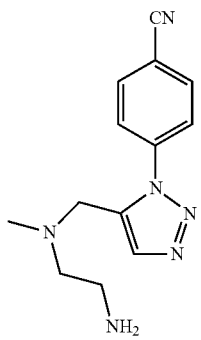 [SMILES: CN(CCN)Cc1cnnn1-c1ccc(C#N)cc1]

A solution of tert-butyl N-[2-([[1-(4-cyanophenyl)-1H-1,2,3-triazol-5-yl]methyl](methyl)amino)ethyl]carbamate (100 mg, 0.28 mmol, 1.00 equiv) in dichloromethane (4 mL) and trifluoroacetic acid (4 mL) was stirred at room temperature for 2 h. The resulting mixture was concentrated under vacuum and the crude product was purified by Prep-HPLC with the following conditions (2#-Waters 2767-2(HPLC-08)): Column, XBridge Shield RP 18, 5 μm, 19*×150 mm; mobile phase, water with 50 mmol NH$_4$HCO$_3$ and CH$_3$CN (10.0% CH$_3$CN up to 28.0% in 2 min, up to 46.0% in 10 min, up to 100.0% in 1 min, down to 10.0% in 1 min); Detector, UV 254 nm to give 41.6 mg (58%) of 4-(5-(((2-aminoethyl)(methyl)amino)methyl)-1H-1,2,3-triazol-1-yl)benzonitrile as a white solid. $^1$H NMR (400 MHz, CD$_3$OD) δ: 8.04-7.91 (s, 5H), 3.76 (s, 2H), 2.76 (t, J~6.2 Hz, 2H), 2.53 (t, J~6.2 Hz, 2H), 2.21 (s, 3H) ppm. LCMS (method H, ESI): RT=1.02 min, m/z=257.1 [M+H]$^+$.

Compound 6

4-(5-(((2-aminoethyl)(methyl)amino)methyl)-1H-imidazol-1-yl)benzonitrile

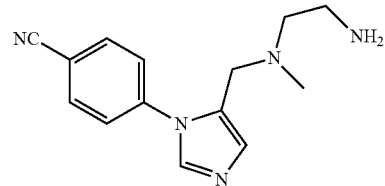 [SMILES: CN(CCN)Cc1cncn1-c1ccc(C#N)cc1]

Step 1 ethyl 1-(4-cyanophenyl)-1H-imidazole-5-carboxylate

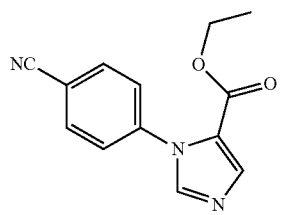 [SMILES: CCOC(=O)c1cncn1-c1ccc(C#N)cc1]

A mixture of ethyl 1H-imidazole-4-carboxylate (10 g, 71.36 mmol, 1.00 equiv), CuI (2.7 g, 14.18 mmol, 0.20 equiv), potassium carbonate (30 g, 217.06 mmol, 3.02 equiv), 4-iodobenzonitrile (25 g, 109.16 mmol, 1.53 equiv) and (1S,2S)-1-N,2-N-dimethylcyclohexane-1,2-diamine (2.0 g, 14.06 mmol, 0.20 equiv) in 1,4-dioxane (200 mL) was stirred under nitrogen at 95° C. overnight. The reaction was cooled to room temperature and the solid material was removed by filtration. The filtrate was diluted with 800 mL of ethyl acetate then washed with 3×400 mL of brine, dried over anhydrous sodium sulfate and concentrated under vacuum. The residue was purified on a silica gel column eluted with 1-3% of methanol in dichloromethane to give 450 mg (3%) of ethyl 1-(4-cyanophenyl)-1H-imidazole-5-carboxylate as a white solid. $^1$H-NMR (300 MHz, DMSO-d6): δ 8.19 (d, J=0.9 Hz, 2H), 7.84 (d, J=0.9 Hz, 2H), 4.15 (q, J=5.4 Hz, 2H), 1.16 (t, J=5.1 Hz, 3H) ppm. LCMS (method D, ESI): RT=1.19 min, m/z=242.0 [M+H]+ and 1.2 g (7%) of ethyl 1-(4-cyanophenyl)-1H-imidazole-4-carboxylate as a white solid. ¹H-NMR (300 MHz, CDCl₃): δ 7.90 (s, 1H), 7.82-7.76 (m, 3H), 7.50-7.47 (m, 2H), 4.24 (q, J=7.2 Hz, 2H), 1.28 (t, J=7.2 Hz, 3H) ppm. LCMS (method D, ESI): RT=1.16 min, m/z=242.0 [M+H]+.

Step 2

4-(5-(hydroxymethyl)-1H-imidazol-1-yl)benzonitrile

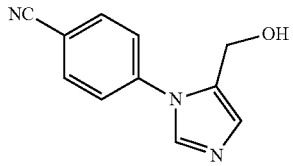 [SMILES: N#Cc1ccc(-n2cncc2CO)cc1]

To a stirred solution of ethyl 1-(4-cyanophenyl)-1H-imidazole-5-carboxylate (50 mg, 0.21 mmol, 1.00 equiv) in anhydrous tetrahydrofuran (10 mL) maintained under nitrogen at −40° C. was added LiAlH₄ (24 mg, 0.63 mmol, 3.05 equiv) in portions. The reaction was stirred at −40° C. for 1 h and then quenched by the addition of 2 mL of saturated aqueous NH₄Cl solution. The solid was removed by filtration and the filtrate was concentrated under vacuum. The residue was purified on a silica gel column eluted with 3.0-6.7% of methanol in dichloromethane to yield 36 mg (87%) of 4-(5-(hydroxymethyl)-1H-imidazol-1-yl)benzonitrile as a white solid. ¹H-NMR (300 MHz, CDCl₃): δ 10.11 (s, 1H), 8.07 (d, J=6.3 Hz, 2H), 7.85 (d, J=6.3 Hz, 2H), 7.77-7.72 (m, 4H), 7.24 (s, 1H), 4.63 (d, J=7.5 Hz, 2H) ppm. LCMS (method C, ESI): RT=0.25 min, m/z=200.0 [M+H]+.

Step 3

4-(5-formyl-1H-imidazol-1-yl)benzonitrile

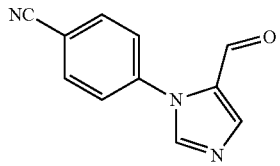 [SMILES: N#Cc1ccc(-n2cncc2C=O)cc1]

A mixture of 4-(5-(hydroxymethyl)-1H-imidazol-1-yl)benzonitrile (80 mg, 0.40 mmol, 1.00 equiv) and MnO₂ (525 mg, 6.04 mmol, 15.04 equiv) in dichloromethane (10 mL) was refluxed for 1 h. The reaction was cooled to room temperature and the solid material was removed by filtration. The filtrate was concentrated under vacuum to give 55 mg (69%) of 4-(5-formyl-1H-imidazol-1-yl)benzonitrile as a white solid. ¹H-NMR (300 MHz, CDCl₃): δ 9.80 (s, 1H), 8.03 (s, 1H), 7.99-7.80 (m, 3H), 7.56-7.49 (m, 2H) ppm. LCMS (method D, ESI): RT=1.06 min, m/z=198.0 [M+H]+.

Step 4 tert-butyl 2-(((1-(4-cyanophenyl)-1H-imidazol-5-yl)methyl)(methyl)amino)ethylcarbamate

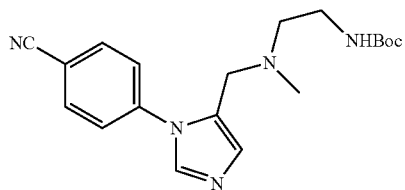 [SMILES: CN(CCNC(=O)OC(C)(C)C)Cc1cncn1-c1ccc(C#N)cc1]

To a solution of 4-(5-formyl-1H-imidazol-1-yl)benzonitrile (55 mg, 0.28 mmol, 1.00 equiv) and tert-butyl N-[2-(methylamino)ethyl]carbamate (58 mg, 0.33 mmol, 1.19 equiv) in 1,2-dichloroethane (20 mL) was added NaBH(OAc)₃ (178 mg, 0.82 mmol, 2.95 equiv). The reaction was stirred at room temperature for 2 h and then concentrated under vacuum. The residue was purified on a silica gel column eluted with 0-5.4% of methanol in dichloromethane to give 90 mg (91%) of tert-butyl 2-(((1-(4-cyanophenyl)-1H-imidazol-5-yl)methyl)(methyl)amino)ethylcarbamate as a colorless oil. LCMS (method D, ESI): RT=0.98 min, m/z=356.0 [M+H]+.

Step 5

Compound 6 4-(5-(((2-aminoethyl)(methyl)amino)methyl)-1H-imidazol-1-yl)benzonitrile

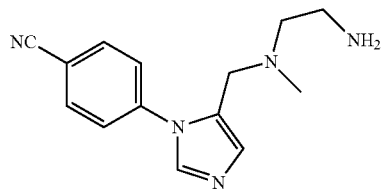 [SMILES: CN(CCN)Cc1cncn1-c1ccc(C#N)cc1]

A solution of tert-butyl N-[2-([[1-(4-cyanophenyl)-1H-imidazol-5-yl]methyl](methyl)amino)ethyl]carbamate (90 mg, 0.25 mmol, 1.00 equiv) in trifluoroacetic acid (5 mL) and dichloromethane (5 mL) was stirred at room temperature for 3 h. The resulting mixture was concentrated under vacuum and the crude product was purified by Prep-HPLC with the following conditions (waters-1): Column, XBridge Shield RP18 OBD Column, 5 μm, 19×150 mm; mobile phase, Phase A: water with 0.03% NH₄OH Phase B: water with 0.05% TFA; Gradient B (20%~50% 2 min~100% 11 min); Detector, UV 254 nm to afford 25.4 mg (39%) of 4-(5-(((2-aminoethyl)(methyl)amino)methyl)-1H-imidazol-1-yl)benzonitrile trifluoroacetate as a white solid. ¹H-NMR (300 MHz, CD₃OD): δ 7.98-7.95 (m, 3H), 7.83-7.80 (m, 2H), 7.15 (s, 1H), 3.60 (s, 2H), 2.76 (t, J=6.3 Hz, 2H), 2.50 (t, J=6.3 Hz, 2H), 2.16 (s, 3H) ppm. LCMS (method S, ESI): RT=1.18 min, m/z=256.3 [M+H]⁺.

Compound 7

4-(4-(((2-aminoethyl)(methyl)amino)methyl)-1,2,5-thiadiazol-3-yl)benzonitrile

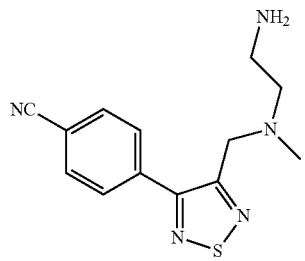 [SMILES: CN(CCN)Cc1nsnc1-c1ccc(C#N)cc1]

Step 1

4-(cyano(trimethylsilyloxy)methyl)benzonitrile

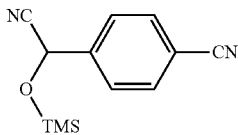 [SMILES: C[Si](C)(C)OC(C#N)c1ccc(C#N)cc1]

A mixture of 4-formylbenzonitrile (3 g, 22.88 mmol, 1.00 equiv), potassium phthalimide (106 mg, 0.57 mmol, 0.03 equiv) and trimethylsilyl cyanide (2.83 g, 28.53 mmol, 1.25 equiv) was stirred at room temperature for 1.5 h. The reaction was then quenched by the addition of 50 mL of water and the resulting mixture was extracted with 3×50 mL of ethyl acetate. The combined organic layers was washed with 3×100 mL of brine, dried over anhydrous sodium sulfate and concentrated under vacuum to give 5.1 g (97%) of 4-[cyano (trimethylsilyloxy)methyl]benzonitrile as a yellow oil. ¹H-NMR (300 MHz, CDCl₃): δ 7.81-7.78 (m, 2H), 7.68 (d, J=8.4 Hz, 2H), 5.62 (s, 1H), 0.34 (s, 9H) ppm.

Step 2

4-(amino(cyano)methyl)benzonitrile hydrochloride

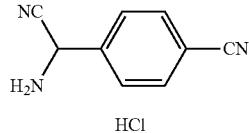 [SMILES: N#Cc1ccc(C(N)C#N)cc1 ; Cl]

A solution of 4-(cyano(trimethylsilyloxy)methyl)benzonitrile (6 g, 26.05 mmol, 1.00 equiv) in a saturated ammonia solution in methanol (20 mL) was stirred in a 50-mL sealed tube at 60° C. for 4 h. The resulting mixture was cooled to room temperature and concentrated under vacuum. The residue was dissolved in 60 mL of ether and then cooled to 0° C.

Hydrogen chloride gas was bubbled into the solution at 0° C. for 15 min. The precipitate was collected by filtration and then dried in a vacuum oven to yield 2.5 g (crude) of 4-(amino (cyano)methyl)benzonitrile hydrochloride as a yellow solid. ¹H-NMR (400 MHz, DMSO-d₆): δ 9.89 (br s, 2H), 8.09-8.00 (m, 2H), 7.91-7.89 (m, 2H), 6.14 (s, 1H) ppm.

Step 3

4-(4-chloro-1,2,5-thiadiazol-3-yl)benzonitrile

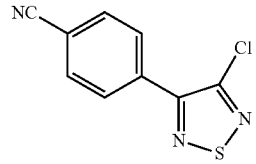 [SMILES: N#Cc1ccc(-c2nsnc2Cl)cc1]

To a solution of sulfur monochloride (5.2 g, 38.51 mmol, 2.98 equiv) in N,N-dimethylformamide (15 mL) at 0° C. was added 4-(amino(cyano)methyl)benzonitrile hydrochloride (2.5 g, 12.91 mmol, 1.00 equiv) portion-wise over 30 min. The resulting mixture was stirred at 0° C. for 20 min and then warmed to room temperature and stirred overnight before pouring into ice-water (200 mL). The resulting mixture was extracted with 3×100 mL of dichloromethane. The combined organic layers were washed with 3×200 mL of brine, dried over anhydrous sodium sulfate and concentrated under vacuum. The residue was purified on a silica gel column eluted with 0-5% of ethyl acetate in petroleum ether to give 1.2 g (42%) of 4-(4-chloro-1,2,5-thiadiazol-3-yl)benzonitrile as a white solid. ¹H-NMR (400 MHz, CDCl₃): δ 8.15 (d, J=8.0 Hz, 2H), 7.84 (d, J=8.0 Hz, 2H) ppm.

Step 4 methyl 4-(4-cyanophenyl)-1,2,5-thiadiazole-3-carboxylate

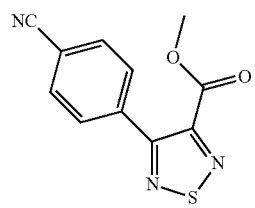 [SMILES: COC(=O)c1nsnc1-c1ccc(C#N)cc1]

A mixture of 4-(4-chloro-1,2,5-thiadiazol-3-yl)benzonitrile (400 mg, 1.80 mmol, 1.00 equiv), Pd(OAc)₂ (41 mg, 0.18 mmol, 0.10 equiv), triethylamine (546 mg, 5.40 mmol, 2.99 equiv) and 1,3-bis(diphenylphosphino)propane (74 mg, 0.18 mmol, 0.10 equiv) in methanol (10 mL) was stirred under 10 atm of carbon monoxide in a 50-mL pressure reactor at 80° C. overnight in an oil bath. The resulting mixture was cooled to room temperature and concentrated under vacuum. The residue was dissolved in 100 mL of dichloromethane and then washed with 2×100 mL of water and 2×100 mL of brine. The organic layer was dried over anhydrous sodium sulfate and concentrated under vacuum. The residue was purified on a silica gel column eluted with 5-20% of ethyl acetate in petroleum ether to yield 327 mg (74%) of methyl 4-(4-cyanophenyl)-1,2,5-thiadiazole-3-carboxylate as a white solid. $^1$H-NMR (300 MHz, CDCl$_3$): δ 7.88 (d, J=8.4 Hz, 2H), 7.81 (d, J=8.4 Hz, 2H), 4.01 (s, 3H) ppm.

Step 5

4-(4-(hydroxymethyl)-1,2,5-thiadiazol-3-yl)benzonitrile

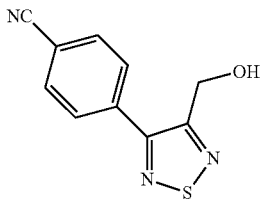 [SMILES: N#Cc1ccc(-c2nsnc2CO)cc1]

To a solution of methyl 4-(4-cyanophenyl)-1,2,5-thiadiazole-3-carboxylate (260 mg, 1.06 mmol, 1.00 equiv) in anhydrous tetrahydrofuran (20 mL) maintained under nitrogen at −5° C. was added LiBH$_4$ (117 mg, 5.32 mmol, 5.02 equiv) portion-wise. The reaction was stirred at room temperature for 1.5 h and then quenched with 5 mL of saturated NH$_4$Cl solution. The mixture was extracted with 3×20 mL of ethyl acetate. The combined organic layers were washed with 3×100 mL of brine, dried over anhydrous sodium sulfate and concentrated to afford 230 mg (100%) of 4-(4-(hydroxymethyl)-1,2,5-thiadiazol-3-yl)benzonitrile as a light yellow solid. $^1$H-NMR (400 MHz, DMSO-d$_6$): δ 8.12 (d, J=8.4 Hz, 2H), 8.03 (d, J=8.4 Hz, 2H), 4.81 (s, 2H) ppm.

Step 6

4-(4-formyl-1,2,5-thiadiazol-3-yl)benzonitrile

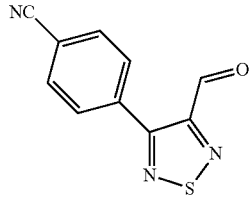 [SMILES: N#Cc1ccc(-c2nsnc2C=O)cc1]

A mixture of 4-[4-(hydroxymethyl)-1,2,5-thiadiazol-3-yl]benzonitrile (230 mg, 1.06 mmol, 1.00 equiv) and MnO$_2$ (922 mg, 10.61 mmol, 10.02 equiv) in dichloromethane (20 mL) was stirred at 40° C. for 1.5 h. The reaction was cooled to room temperature and the solids were removed by filtration. The filtrate was concentrated under vacuum and the residue was purified on a silica gel column eluted with 2.5-5% of ethyl acetate in petroleum ether to give 113 mg (50%) of 4-(4-formyl-1,2,5-thiadiazol-3-yl)benzonitrile as a white solid. $^1$H-NMR (300 MHz, CDCl$_3$): δ 10.34 (s, 1H), 8.00 (d, J=8.4 Hz, 1H), 7.80 (d, J=8.1 Hz, 1H) ppm.

Step 7 tert-butyl 2-(((4-(4-cyanophenyl)-1,2,5-thiadiazol-3-yl)methyl)(methyl)amino)ethyl)carbamate

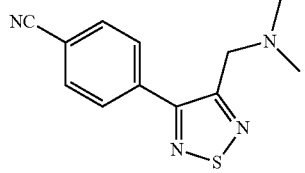
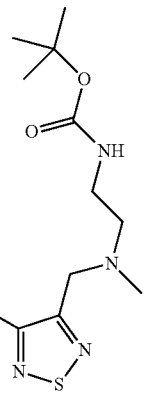

To a solution of 4-(4-formyl-1,2,5-thiadiazol-3-yl)benzonitrile (113 mg, 0.53 mmol, 1.00 equiv) and tert-butyl N-[2-(methylamino)ethyl]carbamate (137 mg, 0.79 mmol, 1.50 equiv) in 1,2-dichloroethane (5 mL) was added NaBH(OAc)$_3$ (223 mg, 1.05 mmol, 2.00 equiv). The reaction was stirred at room temperature for 2 h and then quenched by the addition of 10 mL of saturated NaHCO$_3$ solution. The resulting mixture was extracted with 3×10 mL of dichloromethane. The combined organic layers were washed with 3×30 mL of brine, dried over anhydrous sodium sulfate and concentrated under vacuum. The residue was purified on a silica gel column eluted with 5-20% of ethyl acetate in petroleum ether to give 129 mg (66%) of tert-butyl 2-(((4-(4-cyanophenyl)-1,2,5-thiadiazol-3-yl)methyl)(methyl)amino)ethyl)carbamate as a colorless oil. LCMS (method D, ESI): RT=1.15 min, m/z=374.0 [M+H]$^+$.

Step 8

Compound 7 4-(4-(((2-aminoethyl)(methyl)amino)methyl)-1,2,5-thiadiazol-3-yl)benzonitrile

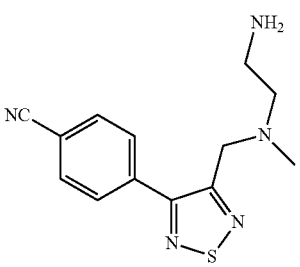 [SMILES: CN(CCN)Cc1nsnc1-c1ccc(C#N)cc1]

Hydrogen chloride gas was bubbled into a solution of tert-butyl 2-(((4-(4-cyanophenyl)-1,2,5-thiadiazol-3-yl)methyl)(methyl)amino)ethyl)carbamate (129 mg, 0.35 mmol, 1.00 equiv) in dichloromethane (10 mL) maintained at 0° C. for 15 min. The reaction was stirred at 0° C. for 1 h and then concentrated under vacuum. The solid was triturated with 3×20 mL of ether and 1×20 mL of n-hexane then dried in a vacuum oven to give 83 mg (69%) of 4-(4-(((2-aminoethyl)(methyl)amino)methyl)-1,2,5-thiadiazol-3-yl)benzonitrile hydrochloride as a white solid. $^1$H-NMR (400 MHz, D$_2$O): δ 7.91 (d, J=8.0 Hz, 2H), 7.77 (d, J=8.4 Hz, 2H), 4.85 (s, 2H), 3.62-3.38 (m, 4H), 2.94 (s, 3H) ppm. LCMS (method T, ESI): RT=0.79 min, m/z=274.1 [M+H]$^+$.

Compound 8

N$^1$-((1-(4-isopropoxyphenyl)-1H-pyrazol-5-yl)methyl)-N$^1$-methylethane-1,2-diamine

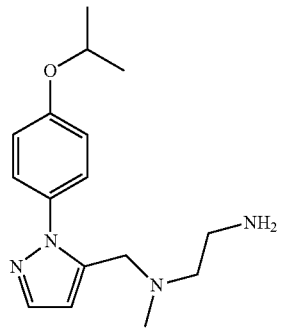 [SMILES: CC(C)Oc1ccc(-n2nccc2CN(C)CCN)cc1]

Step 1

(4-isopropoxyphenyl)hydrazine hydrochloride

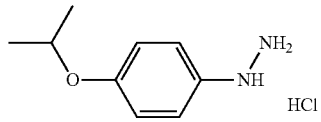

To a stirred solution of 4-(propan-2-yloxy)aniline (5.0 g, 33.07 mmol, 1.00 equiv) in 2N hydrochloric acid (35 mL) at 0° C. was added dropwise a solution of sodium nitrite (2.4 g, 34.78 mmol, 1.05 equiv) in water (8 mL). The reaction mixture was stirred at 0-5° C. for 1 h. A solution of SnCl$_2$.H$_2$O (15 g, 66.37 mmol, 2.01 equiv) in 12N hydrochloric acid (20 mL) was then added dropwise at 0-5° C. The resulting mixture was stirred at room temperature overnight. The precipitates was collected by filtration to give 4.7 g (70%) of crude (4-isopropoxyphenyl)hydrazine hydrochloride as a purple solid. The product was used in the next step without further purification.

Step 2

4-(dimethylamino)-1,1-dimethoxybut-3-en-2-one

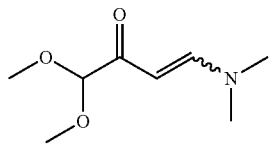

A mixture of 1,1-dimethoxypropan-2-one (10 g, 84.65 mmol, 1.00 equiv) and DMF-DMA (10 g, 84.03 mmol, 0.99 equiv) was stirred at 100° C. for 5 h. The resulting mixture was cooled to room temperature and concentrated under vacuum to give 18 g of crude 4-(dimethylamino)-1,1-dimethoxybut-3-en-2-one as a brown liquid. The crude product was used in the next step without further purification.

Step 3

1-(4-isopropoxyphenyl)-1H-pyrazole-5-carbaldehyde

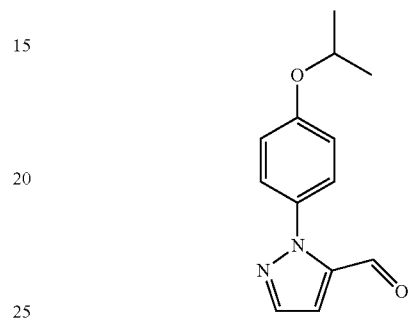

A solution of [4-(propan-2-yloxy)phenyl]hydrazine hydrochloride (1 g, 4.93 mmol, 1.00 equiv) and (4,4-dimethoxy-3-oxobut-1-en-1-yl)dimethylamine (1.4 g, 8.08 mmol, 1.64 equiv) in ethanol (20 mL) was refluxed for 3 h. The resulting mixture was cooled to room temperature and concentrated under vacuum. Acetone (10 mL) and 6N hydrochloric acid (10 mL) was added to dissolve the residue and the resulting solution was stirred at room temperature overnight. The reaction was diluted with 100 mL of dichloromethane and then washed with 3×50 mL of brine. The organic layer was dried over anhydrous sodium sulfate and concentrated under vacuum. The residue was purified on a silica gel column eluted with 3.0-7.0% of methanol in dichloromethane to yield 200 mg (18%) of 1-[4-(propan-2-yloxy)phenyl]-1H-pyrazole-5-carbaldehyde as a yellow oil. LCMS (method A, ESI): RT=1.48 min, m/z=230.9 [M+H]$^+$.

Step 4 tert-butyl 2-(((1-(4-isopropoxyphenyl)-1H-pyrazol-5-yl)methyl)(methyl)amino)ethyl)carbamate

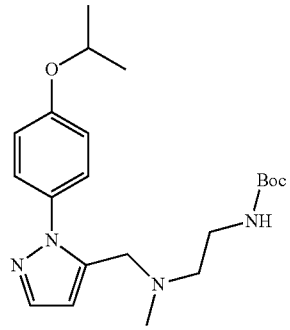 [SMILES: CC(C)Oc1ccc(-n2nccc2CN(C)CCNC(=O)OC(C)(C)C)cc1]

To a solution of 1-[4-(propan-2-yloxy)phenyl]-1H-pyrazole-5-carbaldehyde (200 mg, 0.87 mmol, 1.00 equiv) and tert-butyl N-[2-(methylamino)ethyl]carbamate (180 mg, 1.03 mmol, 1.19 equiv) in 1,2-dichloroethane (5 mL) was added NaBH(OAc)$_3$ (550 mg, 2.60 mmol, 2.99 equiv). The mixture was stirred at room temperature for 5 h and then diluted with 10 mL of H₂O. The resulting mixture was extracted with 3×20 mL of dichloromethane. The combined organic layers were dried over anhydrous sodium sulfate and concentrated under vacuum. The residue was purified on a silica gel column eluted with 0-10% of ethyl acetate in petroleum ether to give 0.18 g (53%) of tert-butyl 2-(((1-(4-isopropoxyphenyl)-1H-pyrazol-5-yl)methyl)(methyl)amino) ethyl)carbamate as a colorless oil. ¹H-NMR (300 MHz, CDCl₃): δ 7.62 (s, 1H), 7.45 (d, J=8.7 Hz, 2H), 7.69 (d, J=9.0 Hz, 2H), 6.52-6.20 (m, 1H), 4.63-4.59 (m, 1H), 3.75-3.40 (m, 2H), 3.29-3.00 (m, 2H), 2.62-2.38 (m, 2H), 2.21 (s, 3H), 1.48 (s, 9H), 1.39 (d, J=6.0 Hz, 2H) ppm. LCMS (method A, ESI): RT=1.64 min, m/z=389.1 [M+H]⁺.

Step 5

Compound 8 N¹-((1-(4-isopropoxyphenyl)-1H-pyrazol-5-yl)methyl)-N-methylethane-1,2-diamine

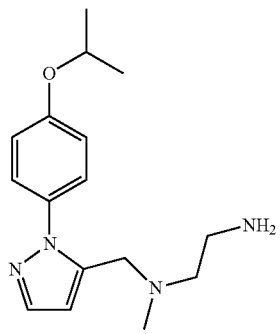 [SMILES: CC(C)Oc1ccc(-n2nccc2CN(C)CCN)cc1]

Hydrogen chloride gas was bubbled into a solution of tert-butyl 2-(((1-(4-isopropoxyphenyl)-1H-pyrazol-5-yl)methyl)(methyl)amino)ethyl)carbamate (180 mg, 0.46 mmol, 1.00 equiv) in methanol (20 mL) at 0° C. for 15 min. The reaction was stirred at room temperature for 5 h and then concentrated under vacuum to give 137.3 mg (82%) of N¹-((1-(4-isopropoxyphenyl)-1H-pyrazol-5-yl)methyl)-N¹-methylethane-1,2-diamine hydrochloride as an off-white solid. ¹H-NMR (300 MHz, D₂O): δ 7.77 (d, J=2.1 Hz, 1H), 7.36-7.33 (m, 2H), 7.12-7.09 (m, 2H), 6.77 (d, J=2.1 Hz, 1H), 4.70-4.65 (m), 4.52 (s, 2H), 3.38-3.20 (m, 4H), 2.66 (s, 3H), 1.28 (d, J=6.3 Hz, 6H) ppm. LCMS (method M, ESI): RT=1.21 min, m/z=289.0 [M+H]⁺.

Compound 10

4-(5-(((2-aminoethyl)(methyl)amino)methyl)-1H-imidazol-4-yl)benzonitrile

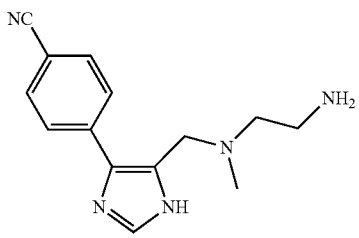 [SMILES: CN(CCN)Cc1[nH]cnc1-c1ccc(C#N)cc1]

Step 1 ethyl 2,4-dibromo-1H-imidazole-5-carboxylate

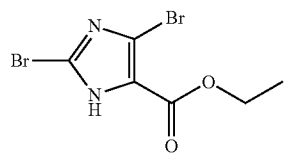

To a solution of ethyl 4H-imidazole-4-carboxylate (6.4 g, 50 mmol, 1.00 equiv) in ethanol (50 mL) was added NBS (17.8 g, 100 mmol, 2.00 equiv) in portions. The reaction was stirred at room temperature for 4 h and then concentrated under vacuum. The residue was purified on a silica gel column eluted with 0-10% of ethyl acetate in petroleum ether to give 3.6 g (74%) of ethyl 2,4-dibromo-1H-imidazole-5-carboxylate as a white solid. ¹H-NMR (300 MHz, CDCl₃): δ 4.45-4.38 (m, 2H), 1.41 (t, J=9.6 Hz, 3H) ppm.

Step 2 ethyl 4-bromo-1H-imidazole-5-carboxylate

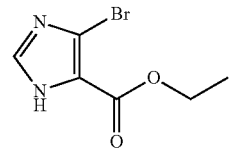

A mixture of ethyl 2,4-dibromo-1H-imidazole-5-carboxylate (9 g, 30.21 mmol, 1.00 equiv) and Na₂SO₃ (7.2 g, 2.00 equiv) in water (80 mL) was stirred at 90° C. for 10 h. The reaction was cooled to room temperature and the solid was collected by filtration, washed with 4×20 mL of water then air-dried to afford 4.0 g (60%) of ethyl 4-bromo-1H-imidazole-5-carboxylate as a white solid. ¹H-NMR (300 MHz, CD₃OD): δ 7.80 (s, 1H), 4.42-4.35 (m, 2H), 1.40 (t, J=9.6 Hz, 3H) ppm. LCMS (method A, ESI): RT=1.13 min, m/z=219.0 [M+H]⁺.

Step 3 ethyl 4-bromo-1-((2-(trimethylsilyl)ethoxy)methyl)-1H-imidazole-5-carboxylate

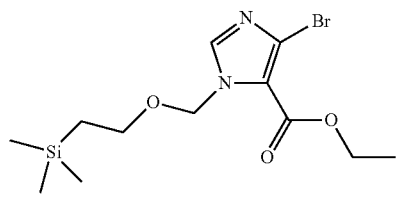 [SMILES: CCOC(=O)c1c(Br)ncn1COCC[Si](C)(C)C]

To a solution of ethyl 4-bromo-1H-imidazole-5-carboxylate (400 mg, 1.83 mmol, 1.00 equiv) in N,N-dimethylformamide (2 mL) was added sodium hydride (100 mg, 4.17 mmol, 1.00 equiv) in portions. The reaction was stirred at room temperature for 20 min then [2-(chloromethoxy)ethyl]trimethylsilane (300 mg, 1.80 mmol, 1.00 equiv) was added. The resulting solution was stirred at room temperature for 5 h and then diluted with 50 mL of ethyl acetate. The mixture was washed with 3×10 mL of brine then the organic layer was dried over anhydrous sodium sulfate and concentrated. The residue was purified on a silica gel column eluted with 0-10% of ethyl acetate in petroleum ether to give 330 mg (52%) of ethyl 4-bromo-1-((2-(trimethylsilyl)ethoxy)methyl)-1H-imidazole-5-carboxylate as a colorless oil. $^1$H-NMR (300 MHz, CDCl$_3$): δ 7.69 (s, 1H), 5.67 (s, 2H), 4.43-4.36 (m, 2H), 3.58 (t, J=10.8 Hz, 2H), 1.45-1.40 (m, 3H), 0.94 (t, J=10.8 Hz, 2H), 0.05 (s, 9H) ppm.

Step 4 ethyl 4-(4-cyanophenyl)-1-((2-(trimethylsilyl)ethoxy)methyl)-1H-imidazole-5-carboxylate

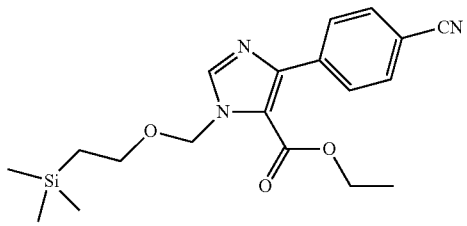 [SMILES: CCOC(=O)c1c(-c2ccc(C#N)cc2)ncn1COCC[Si](C)(C)C]

A mixture of ethyl 4-bromo-1-[[2-(trimethylsilyl)ethoxy]methyl]-1H-imidazole-5-carboxylate (3.48 g, 9.96 mmol, 1.00 equiv), (4-cyanophenyl)boronic acid (3.0 g, 20.42 mmol, 2.00 equiv), Pd(dppf)Cl$_2$.CH$_2$Cl$_2$ (0.42 g, 0.06 equiv) and potassium carbonate (4.0 g, 3.00 equiv) in N,N-dimethylformamide (20 mL) was stirred under nitrogen at 100° C. for 5 h. The reaction was cooled to room temperature and then diluted with 100 mL of ethyl acetate. The mixture was washed with 4×50 mL of brine. The organic layer was dried over anhydrous sodium sulfate and concentrated. The residue was purified on a silica gel column eluted with 0-20% of ethyl acetate in petroleum ether to give 3.05 g (82%) of ethyl 4-(4-cyanophenyl)-1-((2-(trimethylsilyl)ethoxy)methyl)-1H-imidazole-5-carboxylate as a yellow oil. LCMS (method A, ESI): RT=1.62 min, m/z=372.0 [M+H]$^+$.

Step 5

4-(5-(hydroxymethyl)-1-((2-(trimethylsilyl)ethoxy)methyl)-1H-imidazol-4-yl)benzonitrile

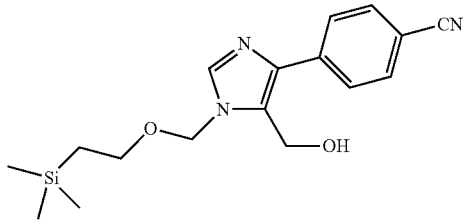 [SMILES: C[Si](C)(C)CCOCn1cnc(-c2ccc(C#N)cc2)c1CO]

To a solution of LiAlH$_4$ (114 mg, 3.36 mmol, 3.00 equiv) in anhydrous THF (5 mL) maintained under nitrogen at −50° C. was added dropwise a solution of ethyl 4-(4-cyanophenyl)-1-((2-(trimethylsilyl)ethoxy)methyl)-1H-imidazole-5-carboxylate (371 mg, 1.00 mmol, 1.00 equiv) in anhydrous THF (2 mL). The reaction was stirred at −50° C. for 1 h and then quenched by the addition of 1 mL of water. The resulting mixture was extracted with 4×20 mL of dichloromethane. The combined organic layers were dried over anhydrous sodium sulfate and concentrated. The residue was purified on a silica gel column eluted with 0-50% of ethyl acetate in petroleum ether to give 110 mg (33%) of 4-(5-(hydroxymethyl)-1-((2-(trimethylsilyl)ethoxy)methyl)-1H-imidazol-4-yl)benzonitrile as a pale yellow solid. $^1$H-NMR (300 MHz, CDCl$_3$): δ 7.92-7.85 (m, 2H), 7.71-7.65 (m, 3H), 5.39 (s, 2H), 4.79 (s, 2H), 3.56 (t, J=11.2 Hz, 2H), 0.94 (t, J=11.2 Hz, 2H), 0.01 (s, 9H) ppm. LCMS (method A, ESI): RT=1.27 min, m/z=330.0 [M+H]$^+$.

Step 6

4-(5-formyl-1-((2-(trimethylsilyl)ethoxy)methyl)-1H-imidazol-4-yl)benzonitrile

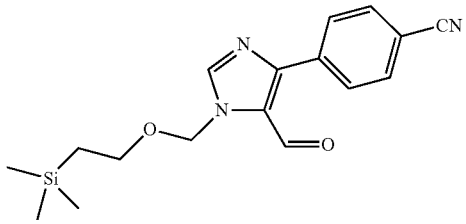 [SMILES: C[Si](C)(C)CCOCn1cnc(-c2ccc(C#N)cc2)c1C=O]

A mixture of 4-(5-(hydroxymethyl)-1-((2-(trimethylsilyl)ethoxy)methyl)-1H-imidazol-4-yl)benzonitrile (100 mg, 0.30 mmol, 1.00 equiv) and MnO$_2$ (260 mg, 2.99 mmol, 10.00 equiv) in dichloromethane (10 mL) was stirred at room temperature for 1 h. The solid material was removed by filtration. The filtrate was concentrated under vacuum to yield 64 mg (64%) of 4-(5-formyl-1-((2-(trimethylsilyl)ethoxy)methyl)-1H-imidazol-4-yl)benzonitrile as a yellow solid. $^1$H-NMR (300 MHz, CDCl$_3$): δ 9.94 (s, 1H), 7.93 (s, 1H), 7.76-7.56 (m, 4H), 5.75 (s, 2H), 3.66 (t, J=9.4 Hz, 2H), 0.94 (t, J=9.4 Hz, 2H), 0.04 (s, 9H) ppm. LCMS (method A, ESI): RT=1.57 min, m/z=328.0 [M+H]$^+$.

Step 7 tert-butyl 2-(((4-(4-cyanophenyl)-1-((2-(trimethylsilyl)ethoxy)methyl)-1H-imidazol-5-yl)methyl)(methyl)amino)ethyl)carbamate

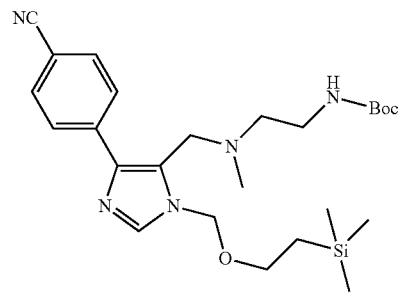 [SMILES: CN(CCNC(=O)OC(C)(C)C)Cc1c(-c2ccc(C#N)cc2)ncn1COCC[Si](C)(C)C]

To a solution of 4-(5-formyl-1-[[2-(trimethylsilyl)ethoxy]methyl]-1H-imidazol-4-yl)benzonitrile (54 mg, 0.16 mmol, 1.00 equiv) and tert-butyl N-[2-(methylamino)ethyl]carbamate (51 mg, 0.29 mmol, 2.00 equiv) in 1,2-dichloroethane (2 mL) was added NaBH(AcO)$_3$ (100 mg, 0.46 mmol, 3.00 equiv). The reaction was stirred at room temperature for 10 h. The pH value of the solution was adjusted to 10 with 5% potassium carbonate solution. The mixture was extracted with 3×10 mL of dichloromethane. The combined organic layers were dried over anhydrous sodium sulfate and concentrated. The residue was purified on a silica gel column eluted with 0-50% of ethyl acetate in petroleum ether to give 64 mg (80%) of tert-butyl 2-(((4-(4-cyanophenyl)-1-((2-(trimethylsilyl)ethoxy)methyl)-1H-imidazol-5-yl)methyl)(methyl)amino)ethyl)carbamate as a colorless oil. LCMS (method A, ESI): RT=1.33 min, m/z=486.0 [M+H]$^+$.

Step 8

Compound 10 4-(5-(((2-aminoethyl)(methyl)amino)methyl)-1H-imidazol-4-yl)benzonitrile

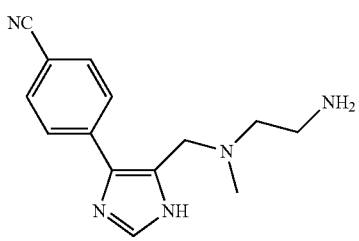 [SMILES: CN(CCN)Cc1[nH]cnc1-c1ccc(C#N)cc1]

A solution of tert-butyl 2-(((4-(4-cyanophenyl)-1-((2-(trimethylsilyl)ethoxy)methyl)-1H-imidazol-5-yl)methyl)(methyl)amino)ethyl)carbamate (60 mg, 0.12 mmol, 1.00 equiv) in trifluoroacetic acid (2 mL) and dichloromethane (1 mL) was stirred at room temperature for 4 h. The precipitated crude product was collected by filtration and then purified by Prep-HPLC with the following conditions: Column, XBridge Shield RP 18, 5 μm, 19×150 mm; mobile phase, water with 50 mmol CF$_3$COOH and CH$_3$CN (10.0% CH$_3$CN up to 28.0% in 2 min, up to 46.0% in 10 min, up to 100.0% in 1 min, down to 10.0% in 1 min); Detector, UV 254 nm to afford 37.3 mg (62%) of 4-(5-(((2-aminoethyl)(methyl)amino)methyl)-1H-imidazol-4-yl)benzonitrile trifluoroacetate as a colorless semi-solid. $^1$H-NMR (300 MHz, D$_2$O): δ 8.72 (s, 1H), 7.90 (d, J=8.4 Hz, 2H), 7.68 (d, J=8.4 Hz, 2H), 4.47 (s, 2H), 3.26-3.18 (m, 4H), 2.54 (s, 3H) ppm. LCMS (method M, ESI): RT=0.92 min, m/z=256.0 [M+H]$^+$.

Compound 11

N-((4-(4-fluorophenyl)isoxazol-5-yl)methyl)-N$^1$-methylethane-1,2-diamine

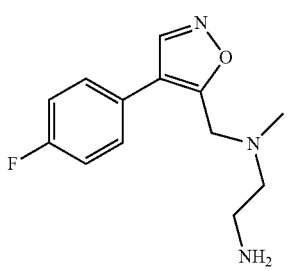 [SMILES: CN(CCN)Cc1oncc1-c1ccc(F)cc1]

Step 1

(4-fluorobenzyl)zinc(II) bromide

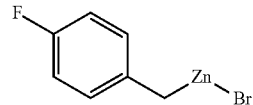

To a stirred mixture of Zn metal (18.5 g, 289.06 mmol, 1.09 equiv), I$_2$ (500 mg, 1.97 mmol, 0.01 equiv) and 1-(bromomethyl)-4-fluorobenzene (5 g, 0.10 equiv) in anhydrous tetrahydrofuran (50 mL) maintained under nitrogen at room temperature was added dropwise a solution of 1-(bromomethyl)-4-fluorobenzene (45 g, 211.6 mmol, 0.90 equiv) in tetrahydrofuran (200 mL). TMSCl (500 mg, 4.60 mmol, 0.02 equiv) was then added dropwise to the reaction. The resulting mixture was refluxed for 10 h. The solution was cooled to 0° C. and used in the next step immediately.

Step 2 ethyl 3-(4-fluorophenyl)-2-oxopropanoate

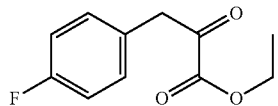

To a stirred mixture of ethyl 2-chloro-2-oxoacetate (35 g, 256.35 mmol, 1.00 equiv) and Pd(PPh$_3$)$_2$Cl$_2$ (9 g, 12.82 mmol, 0.05 equiv) in tetrahydrofuran (200 mL) maintained under nitrogen at 0° C. was added dropwise a solution of (4-fluorobenzyl)zinc(II) bromide (65 g, 255.47 mmol, 1.00 equiv) in tetrahydrofuran (500 mL). The reaction mixture was refluxed for 12 h then cooled to 0° C. and quenched by dropwise addition of 500 mL of saturated NH$_4$Cl solution. The resulting mixture was extracted with 2×500 mL of ethyl acetate. The combined organic layers was washed with 1×1 L of brine, dried over anhydrous sodium sulfate and concentrated under vacuum. The residue was purified on a silica gel column eluted with 0-5% of ethyl acetate in petroleum ether to give 18 g (34%) of ethyl 3-(4-fluorophenyl)-2-oxopropanoate as a yellow oil. $^1$H-NMR (300 MHz, DMSO): δ 7.36-7.33 (m, 2H), 7.18-7.12 (m, 2H), 4.50 (s, 1H), 4.26 (q, J=7.0 Hz, 2H), 1.20 (t, J=7.2 Hz, 3H) ppm.

Step 3

(E)-ethyl 4-ethoxy-3-(4-fluorophenyl)-2-oxobut-3-enoate

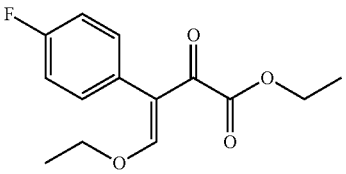 [SMILES: CCO/C=C(/C(=O)C(=O)OCC)c1ccc(F)cc1]

A solution of ethyl 3-(4-fluorophenyl)-2-oxopropanoate (4 g, 19.03 mmol, 1.00 equiv) and triethoxymethane (16 mL) in acetic anhydride (5 mL) was stirred at 130° C. overnight. The reaction mixture was cooled to room temperature and then concentrated under vacuum. The residue was purified on a silica gel column eluted with 0-10% of ethyl acetate in petroleum ether to give 700 mg (14%) of (E)-ethyl 4-ethoxy-3-(4-fluorophenyl)-2-oxobut-3-enoate as a yellow oil. $^1$H-NMR (300 MHz, DMSO-d6): δ 7.71 (s, 1H), 7.32-7.28 (m, 2H), 7.09-7.05 (m, 2H), 4.23 (q, J=7.0 Hz, 2H), 4.16 (q, J=8.0 Hz, 2H), 1.37-1.20 (m, 6H) ppm.

Step 4 ethyl 4-(4-fluorophenyl)isoxazole-5-carboxylate

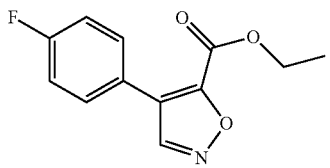 [SMILES: CCOC(=O)c1oncc1-c1ccc(F)cc1]

A solution of (E)-ethyl 4-ethoxy-3-(4-fluorophenyl)-2-oxobut-3-enoate (1.5 g, 5.63 mmol, 1.00 equiv) and hydroxylamine hydrochloride (2 g, 28.99 mmol, 5.15 equiv) in ethanol (10 mL) was refluxed for 3 h. The reaction mixture was cooled to room temperature and then quenched by 15 mL of saturated sodium bicarbonate solution. The resulting mixture was extracted with 2×10 mL of ethyl acetate. The combined organic layers was dried over anhydrous sodium sulfate and concentrated under vacuum. The residue was purified on a silica gel column eluted with 0-10% of ethyl acetate in petroleum ether to yield 340 mg (26%) of ethyl 4-(4-fluorophenyl)-1,2-oxazole-5-carboxylate as a yellow oil. $^1$H-NMR (300 MHz, CDCl$_3$): δ 8.57 (s, 1H), 7.47-7.43 (m, 2H), 7.11-7.03 (m, 2H), 4.43 (q, J=7.2 Hz, 2H), 1.30 (t, J=7.2 Hz, 3H) ppm.

Step 5

(4-(4-fluorophenyl)isoxazol-5-yl)methanol

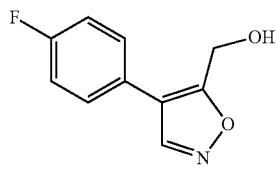 [SMILES: OCc1oncc1-c1ccc(F)cc1]

To a stirred mixture of LiAlH$_4$ (259 mg, 6.82 mmol, 2.01 equiv) in anhydrous tetrahydrofuran (10 mL) maintained under nitrogen at −60° C. was added dropwise a solution of ethyl 4-(4-fluorophenyl)-1,2-oxazole-5-carboxylate (800 mg, 3.40 mmol, 1.00 equiv) in tetrahydrofuran (10 mL). The reaction mixture was stirred at −35° C. for 1 h and then quenched by 2.5 mL of saturated NH$_4$Cl solution. The solid material was removed by filtration. The filtrate was dried over anhydrous sodium sulfate and concentrated under vacuum. The residue was purified on a silica gel column eluted with 10-15% of ethyl acetate in petroleum ether to give 300 mg (46%) of (4-(4-fluorophenyl)isoxazol-5-yl)methanol as a yellow oil. $^1$H-NMR (300 MHz, CDCl$_3$): δ 8.53 (s, 1H), 7.55-7.50 (m, 2H), 7.20-7.07 (m, 2H), 4.87 (s, 2H) ppm. LCMS (method C, ESI): RT=0.79 min, m/z=194.0 [M+H]$^+$.

Step 6 tert-butyl 2-(((4-(4-fluorophenyl)isoxazol-5-yl)methyl)methyl)amino)ethyl)carbamate

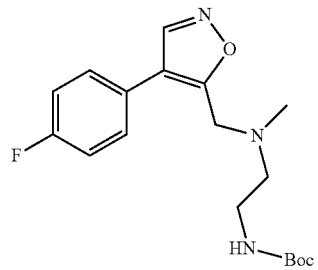 [SMILES: CN(CCNC(=O)OC(C)(C)C)Cc1oncc1-c1ccc(F)cc1]

To a stirred solution of (4-(4-fluorophenyl)isoxazol-5-yl)methanol (240 mg, 1.24 mmol, 1.00 equiv) and TEA (377 mg, 3.73 mmol, 3.00 equiv) in dichloromethane (20 mL) at 0° C. was added methanesulfonyl chloride (215 mg, 1.88 mmol, 1.51 equiv). The reaction mixture was stirred at room temperature for 2 h. tert-butyl N-[2-(methylamino)ethyl]carbamate (649 mg, 3.72 mmol, 3.00 equiv) was then added and the reaction was stirred at room temperature for another 2 h. The resulting mixture was concentrated under vacuum and the residue was purified on a silica gel column eluted with 7-15% of ethyl acetate in petroleum ether to yield 300 mg (69%) of tert-butyl 2-(((4-(4-fluorophenyl)isoxazol-5-yl)methyl)(methyl)amino)ethyl)carbamate as a yellow oil. LCMS (method A, ESI): RT=1.11 min, m/z=350 [M+H]$^+$.

Step 7

Compound 11 N$^1$-((4-(4-fluorophenyl)isoxazol-5-yl)methyl)-N$^1$-methylethane-1,2-diamine

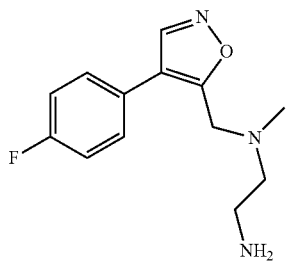 [SMILES: CN(CCN)Cc1oncc1-c1ccc(F)cc1]

A solution of tert-butyl 2-(((4-(4-fluorophenyl)isoxazol-5-yl)methyl)(methyl)amino)ethyl)carbamate (300 mg, 0.86 mmol, 1.00 equiv) in trifluoroacetic acid (5 mL) and dichloromethane (5 mL) was stirred at room temperature for 2 h. The resulting mixture was concentrated under vacuum and the crude product was purified by Prep-HPLC with the following conditions (Prep-HPLC-019): Column, XBridge Shield RP18 OBD Column, 5 µm, 19×150 mm; mobile phase, water with 0.05% TFA and MeCN (6.0% MeCN up to 10.0% in 10 min); Detector, UV 220/254 nm to give 74.9 mg (35%) of N$^1$-((4-(4-fluorophenyl)isoxazol-5-yl)methyl)-N$^1$-methylethane-1,2-diamine trifluoroacetate as a colorless oil. $^1$H-NMR (300 MHz, D$_2$O): δ 8.87 (s, 1H), 7.42-7.37 (m, 2H), 7.24-7.18 (m, 2H), 4.69-4.71 (m, 2H), 3.57-3.52 (m, 2H), 3.42-3.37 (m, 2H), 2.90 (s, 3H) ppm. LCMS (method O, ESI): RT=3.81 min, m/z=250.0 [M+H]$^+$.

Synthesis of Intermediates

Intermediate I tert-butyl (2-(((3-iodo-1-(tetrahydro-2H-pyran-2-yl)-1H-pyrazol-4-yl)methyl)(methyl)amino)ethyl)carbamate

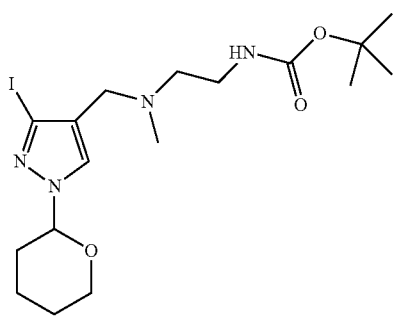 [SMILES: CN(CCNC(=O)OC(C)(C)C)Cc1cn(C2CCCCO2)nc1I]

Step 1 tert-butyl (2-(((3-iodo-1-(tetrahydro-2H-pyran-2-yl)-1H-pyrazol-4-yl)methyl)(methyl)amino)ethyl)carbamate

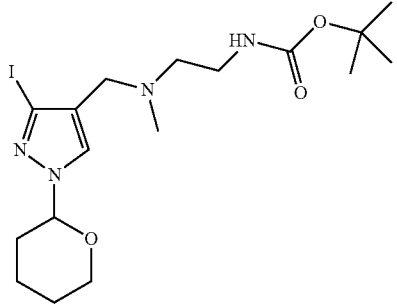 [SMILES: CN(CCNC(=O)OC(C)(C)C)Cc1cn(C2CCCCO2)nc1I]

A mixture of 3-iodo-1-(oxan-2-yl)-1H-pyrazole-4-carbaldehyde (3.2 g, 10.45 mmol, 1.00 equiv), tert-butyl N-[2-(methylamino)ethyl]carbamate (2.2 g, 12.63 mmol, 1.21 equiv) and NaBH(OAc)$_3$ (6.65 g, 31.38 mmol, 3.00 equiv) in dichloroethane (30 mL) was stirred for 2 h at room temperature. The reaction was quenched with 50 mL of saturated aqueous sodium bicarbonate solution. The resulting mixture was extracted with 3×200 mL of dichloromethane. The combined organic layers was dried over anhydrous sodium sulfate and concentrated under vacuum. The residue was purified on a silica gel column eluted with 30-100% ethyl acetate in petroleum ether to give 4.05 g (83%) of tert-butyl (2-(((3-iodo-1-(tetrahydro-2H-pyran-2-yl)-1H-pyrazol-4-yl)methyl)(methyl)amino)ethyl)carbamate as a light yellow oil. $^1$H NMR (300 MHz, CDCl$_3$): δ 7.48 (s, 1H), 5.35-5.30 (m, 1H), 4.13-4.03 (m, 1H), 3.71-3.63 (m, 1H), 3.36 (s, 2H), 3.26-3.25 (m, 2H), 2.52-2.49 (m, 2H), 2.21 (s, 3H), 2.09-2.01 (m, 3H), 1.68-1.58 (m, 3H), 1.44 (s, 9H) ppm. LCMS (method C, ESI): RT=0.58 min, m/z=465.0 [M+H]$^+$.

Intermediate II tert-butyl (2-(((3-iodo-1-(tetrahydro-2H-pyran-2-yl)-1H-pyrazol-4-yl)methyl)(methyl)amino)ethyl)(methyl)carbamate

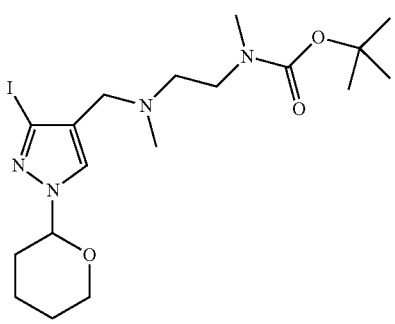 [SMILES: CN(CCN(C)C(=O)OC(C)(C)C)Cc1cn(C2CCCCO2)nc1I]

Step 1 ethyl 3-iodo-1H-pyrazole-4-carboxylate

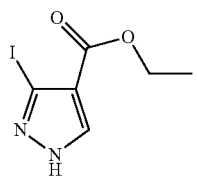

To a stirred solution of ethyl 3-amino-1H-pyrazole-4-carboxylate (10 g, 64.45 mmol, 1.00 equiv) in 50% sulfuric acid (90 mL) at 5° C. was added dropwise a solution of NaNO$_2$ (7.4 g, 107.25 mmol, 1.66 equiv) in water (15 mL). The reaction was stirred at 5° C. for another 30 min. A solution of KI (32.1 g, 193.37 mmol, 3.00 equiv) in water (15 mL) was added dropwise at 5° C. The reaction was allowed to stir at 5° C. for 1 h and then quenched by the addition of 50 mL of water. The precipitate was collected by filtration and then dissolved in 150 mL of ethyl acetate. The resulting solution was washed sequentially with 1×100 mL of saturated Na$_2$SO$_3$ solution, 1×100 mL of saturated sodium bicarbonate solution and 1×100 mL of brine. The organic layer was dried over anhydrous sodium sulfate and concentrated under vacuum to give 10.8 g (63%) of ethyl 3-iodo-1H-pyrazole-4-carboxylate as a yellow solid. $^1$H NMR (300 MHz, CDCl$_3$): δ 8.18 (s, 1H), 4.38-4.29 (m, 2H), 1.41-1.33 (m, 3H) ppm. LCMS (method B, ESI): RT=1.36 min, m/z=267.0 [M+H]+.

Step 2 ethyl 3-iodo-1-(tetrahydro-2H-pyran-2-yl)-1H-pyrazole-4-carboxylate

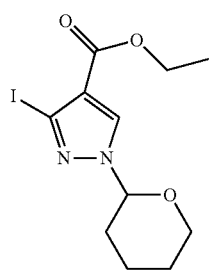 [SMILES: CCOC(=O)c1cn(C2CCCCO2)nc1I]

A solution of ethyl 3-iodo-1H-pyrazole-4-carboxylate (10.8 g, 40.60 mmol, 1.00 equiv), 3,4-dihydro-2H-pyran (10 g, 118.88 mmol, 2.93 equiv) and TsOH (780 mg, 4.53 mmol, 0.11 equiv) in THF (100 mL) was stirred for 2 h at 60° C. The reaction mixture was cooled to room temperature and quenched by the addition of 100 mL of saturated sodium bicarbonate solution. The resulting solution was extracted with 2×80 mL of dichloromethane. The combined organic layers was dried over anhydrous sodium sulfate and concentrated under vacuum. The residue was purified on a silica gel column eluted with ethyl acetate/petroleum ether (1:20) to give 13 g (91%) of ethyl 3-iodo-1-(oxan-2-yl)-1H-pyrazole-4-carboxylate as a yellow oil. $^1$H NMR (400 MHz, CDCl$_3$): δ 8.04 (s, 1H), 5.40-5.38 (m, 1H), 4.34-4.29 (m, 2H), 4.08-4.05 (m, 1H), 3.73-3.70 (m, 1H), 2.07-1.98 (m, 3H), 1.69-1.62 (m, 3H), 1.39-1.32 (m, 3H) ppm. LCMS (method C, ESI): RT=1.53 min, m/z=351.0 [M+H]+.

Step 3

3-iodo-1-(tetrahydro-2H-pyran-2-yl)-1H-pyrazole-4-carboxylic acid

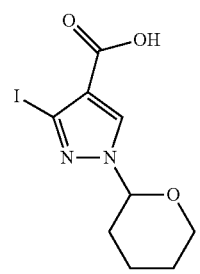 [SMILES: O=C(O)c1cn(C2CCCCO2)nc1I]

To a solution of ethyl 3-iodo-1-(oxan-2-yl)-1H-pyrazole-4-carboxylate (85 g, 242.75 mmol, 1.00 equiv) in THF (300 mL) and methanol (300 mL) was added a solution of LiOH (17.5 g, 730.69 mmol, 3.01 equiv) in water (400 mL). The resulting solution was stirred at room temperature overnight and then concentrated under vacuum to remove the organic solvent. The resulting solution was diluted with 400 mL of H$_2$O and then acidified to pH 6.0 with 1M hydrochloric acid. The mixture was extracted with 3×800 mL of dichloromethane. The combined organic layers was washed with 3×1000 mL of brine, dried over anhydrous sodium sulfate and concentrated under vacuum to give 75 g (96%) of 3-iodo-1-(oxan-2-yl)-1H-pyrazole-4-carboxylic acid as an off-white solid. LCMS (method D, ESI): RT=1.23 min, m/z=323.0 [M+H]+.

Step 4

(3-iodo-1-(tetrahydro-2H-pyran-2-yl)-1H-pyrazol-4-yl)methanol

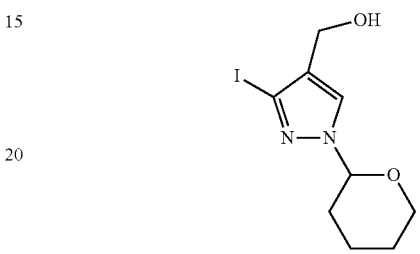

To a solution of 3-iodo-1-(oxan-2-yl)-1H-pyrazole-4-carboxylic acid (28 g, 86.93 mmol, 1.00 equiv) in anhydrous THF (300 mL) maintained under nitrogen at 5° C. was added a 1M solution of BH$_3$ in THF (300 mL) dropwise with stirring. The reaction was stirred overnight at room temperature and then quenched by the addition of 300 mL of saturated NH$_4$Cl solution. The resulting mixture was extracted with 3×1000 mL of dichloromethane. The combined organic layers was dried over anhydrous sodium sulfate and concentrated under vacuum. The residue was purified on a silica gel column eluted with ethyl acetate/petroleum ether (1:1) to give 12.67 g (47%) of (3-iodo-1-(oxan-2-yl)-1H-pyrazol-4-yl) methanol as a white solid. $^1$H NMR (400 MHz, DMSO-d6): δ 7.73 (s, 1H), 5.37-5.34 (m, 1H), 4.92 (s, 1H), 4.20 (d, J=3.6 Hz, 2H), 3.89-3.88 (m, 1H), 3.65-3.57 (m, 1H), 2.09-2.00 (m, 1H), 1.99-1.90 (m, 2H), 1.69-1.61 (m, 1H), 1.49-1.46 (m, 2H) ppm. LCMS (method A, ESI): RT=1.16 min, m/z=309.0 [M+H]+.

Step 5

3-iodo-1-(tetrahydro-2H-pyran-2-yl)-1H-pyrazole-4-carbaldehyde

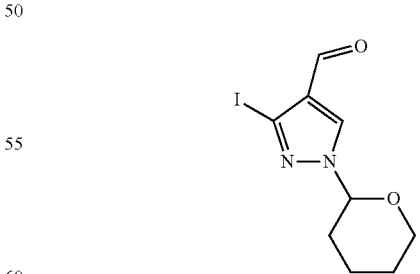

Into a 250-mL 3-necked round-bottom flask purged and. To a stirred solution of oxalyl chloride (18.576 g, 146.35 mmol, 3.01 equiv) in anhydrous dichloromethane (300 mL) maintained under nitrogen at −78° C. was added DMSO (15.138 g, 193.75 mmol, 3.98 equiv) dropwise. The reaction mixture was stirred at −65° C. for 30 min. A solution of (3-iodo-1-

(oxan-2-yl)-1H-pyrazol-4-yl)methanol (15.0 g, 48.68 mmol, 1.00 equiv) in dichloromethane (100 mL) was then added dropwise at −65° C. and the reaction was stirred for another 60 min at −65° C. Triethylamine (40.6 mL) was added dropwise at −65° C. and the reaction was stirred for 30 min at −65° C. The reaction was warmed to 0° C. then quenched by the addition of 100 mL of saturated NH$_4$Cl solution. The resulting mixture was extracted with 3×400 mL of dichloromethane. The combined organic layers was dried over anhydrous sodium sulfate and concentrated under vacuum. The residue was purified on a silica gel column eluted with ethyl acetate/petroleum ether (1:20) to give 13.48 g (90%) of 3-iodo-1-(oxan-2-yl)-1H-pyrazole-4-carbaldehyde as a golden oil. $^1$H NMR (300 MHz, DMSO-d6): δ 9.69 (s, 1H), 8.57 (s, 1H), 5.49 (dd, J=2.7 Hz, 9.9 Hz, 1H), 3.95-3.91 (m, 1H), 3.68-3.62 (m, 1H), 2.11-2.01 (m, 3H), 1.69-1.62 (m, 3H) ppm. LCMS (method A, ESI): RT=1.35 min, m/z=307.0 [M+H]$^+$.

Step 6 tert-butyl (2-(((3-iodo-1-(tetrahydro-2H-pyran-2-yl)-1H-pyrazol-4-yl)methyl)methyl)amino)ethyl)methyl)carbamate

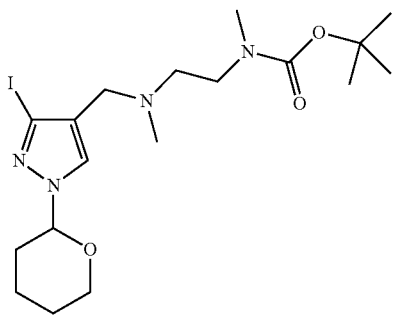 [SMILES: CN(CCN(C)C(=O)OC(C)(C)C)Cc1cn(C2CCCCO2)nc1I]

A mixture of 3-iodo-1-(oxan-2-yl)-1H-pyrazole-4-carbaldehyde (21.5 g, 70.24 mmol, 1.00 equiv), tert-butyl N-methyl-N-(2-(methylamino)ethyl)carbamate (20 g, 106.23 mmol, 1.51 equiv) and NaBH(OAc)$_3$ (29.8 g, 137.98 mmol, 1.96 equiv) in dichloroethane (300 mL) was stirred for 1 h at room temperature. The reaction was diluted with 300 mL of dichloromethane and then washed with 3×300 mL of brine. The organic layer was dried over anhydrous sodium sulfate and concentrated under vacuum. The residue was purified on a silica gel column eluted with 0-7% methanol in dichloromethane to give 31 g (92%) of tert-butyl (2-(((3-iodo-1-(tetrahydro-2H-pyran-2-yl)-1H-pyrazol-4-yl)methyl)(methyl)amino)ethyl)(methyl)carbamate as a yellow oil. $^1$H NMR (300 MHz, CDCl$_3$): δ 7.62 (s, 1H), 5.34-5.30 (m, 1H), 4.06-4.02 (m, 1H), 3.68-3.62 (m, 1H), 3.42-3.38 (m, 4H), 2.85 (s, 4H), 2.62-2.53 (m, 2H), 2.47-2.46 (m, 2H), 2.13-1.97 (m, 3H), 1.74-1.69 (m, 3H), 1.46 (s, 9H) ppm. LCMS (method A, ESI): RT=1.17 min, m/z=479.0 [M+H]$^+$.

Biological Methods
PRMT1 Biochemical Assay

General Materials. S-adenosylmethionine (SAM), S-adenosylhomocysteine (SAH), bicine, Tween20, dimethylsulfoxide (DMSO), bovine skin gelatin (BSG), and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates. Peptide representative of human histone H4 residues 36-50 was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-RLARRGGVKRIS-GLI-amide (SEQ ID NO.: 1).

Molecular Biology: Full-length human PRMT1 isoform 1 (NM_001536.5) transcript clone was amplified from an HEK 293 cDNA library, incorporating flanking 5' sequence encoding a FLAG tag (DYKDDDDK) (SEQ ID NO.:2) fused directly to Met 1 of PRMT1. The amplified gene was subcloned into pFastBacI (Life Technologies) modified to encode an N-terminal GST tag and a TEV cleavage sequence (MSPILGYWKIKGLVQPTRLLLEYLEEKY-EEHLYERDEGDKWRNKKFELGLEFPNLPYYI DGD-VKLTQSMAIIRYIADKHNMLGGCPKER-AEISMLEGAVLDIRYGVSRIAYSKDFETLK VDFLSKLPEMLKMFEDRLCHKTYLNGDH-VTHPDFMLYDALDVVLYMDPMCLDAFPKL VCFKKRIEAIPQIDKYLKSSKYIAW-PLQGWQATFGGGDHPPKSDENLYFQGGNS) (SEQ ID NO.:3) fused to Asp of the Flag tag of PRMT1.

Protein Expression. Recombinant baculovirus were generated according to Bac-to-Bac kit instructions (Life Technologies). Protein over-expression was accomplished by infecting exponentially growing High Five insect cell culture at 1.5× 10$^6$ cell/ml with 1:100 ratio of virus. Infections were carried out at 27° C. for 48 hours, harvested by centrifugation, and stored at −80° C. for purification.

Protein Purification. Expressed full-length human GST-tagged PRMT1 protein was purified from cell paste by glutathione sepharose affinity chromatography after equilibration of the resin with 50 mM phosphate buffer, 200 mM NaCl, 5% glycerol, 5 mM β-mercaptoethanol, pH7.8 (Buffer A). GST-tagged PRMT1 was eluted with 50 mM Tris, 2 mM glutathione, pH 7.8, dialysed in buffer A and concentrated to 1 mg/mL. The purity of recovered protein was 73%. Reference: Wasilko, D. J. and S. E. Lee: "TIPS: titerless infected-cells preservation and scale-up" Bioprocess J., 5 (2006), pp. 29-32.

Predicted Translations:

```
GST-tagged PRMT1
                                         (SEQ ID NO.: 4)
MSPILGYWKIKGLVQPTRLLLEYLEEKYEEHLYERDEGDKWRNKKFELG

LEFPNLPYYIDGDVKLTQSMAIIRYIADKHNMLGGCPKERAEISMLEGA

VLDIRYGVSRIAYSKDFETLKVDFLSKLPEMLKMFEDRLCHKTYLNGDH

VTHPDFMLYDALDVVLYMDPMCLDAFPKLVCFKKRIEAIPQIDKYLKSS

KYIAWPLQGWQATFGGGDHPPKSDENLYFQGGNSDYKDDDDKMAAAEAA

NCIMENFVATLANGMSLQPPLEEVSCGQAESSEKPNAEDMTSKDYYFDS

YAHFGIHEEMLKDEVRTLTYRNSMFHNRHLFKDKVVLDVGSGTGILCMF

AAKAGARKVIGIECSSISDYAVKIVKANKLDHVVTIIKGKVEEVELPVE

KVDIIISEWMGYCLFYESMLNTVLYARDKWLAPDGLIFPDRATLYVTAI

EDRQYKDYKIHWWENVYGFDMSCIKDVAIKEPLVDVVDPKQLVTNACLI
```

-continued
KEVDIYTVKVEDLTFTSPFCLQVKRNDYVHALVAYFNIEFTRCHKRTGF

STSPESPYTHWKQTVFYMEDYLTVKTGEEIFGTIGMRPNAKNNRDLDFT

IDLDFKGQLCELSCSTDYRMR

General Procedure for PRMT1 Enzyme Assays on Peptide Substrates. The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of PRMT1, was added to columns 11, 12, 23, 24, rows I-P for the minimum signal control. A cocktail (40 ul) containing the PRMT1 enzyme was added by Multidrop Combi (Thermo-Fisher). The compounds were allowed to incubate with PRMT1 for 30 min at room temperature, then a cocktail (10 ul) containing SAM and peptide was added to initiate the reaction (final volume=51 ul). The final concentrations of the components were as follows: PRMT1 was 0.5 nM, $^3$H-SAM was 200 nM, non-radiolabeled SAM was 1.5 uM, peptide was 20 nM, SAH in the minimum signal control wells was 1 mM, and the DMSO concentration was 2%. The assays were stopped by the addition of non-radiolabeled SAM (10 ul) to a final concentration of 300 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \, inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter IC50 Fit $$Y = Bottom + \frac{(Top - Bottom)}{\left(1 + \left(\frac{X}{IC_{50}}\right)^{Hill \, Coefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

PRMT6 Biochemical Assay

General Materials. S-adenosylmethionine (SAM), S-adenosylhomocysteine (SAH), bicine, Tween20, dimethylsulfoxide (DMSO), bovine skin gelatin (BSG), sodium butyrate and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates. Peptide representative of human histone H4 residues 36-50 was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-RLARRGGVKRIS-GLI-amide and contained a monomethylated lysine at position 44 (SEQ ID NO.:5).

Molecular Biology: Full-length human PRMT6 (NM_018137.2) transcript clone was amplified from an HEK 293 cDNA library, incorporating a flanking 5' sequence encoding a FLAG tag (MDYKDDDDK) (SEQ ID NO.:6) fused directly to Ser 2 of PRMT6 and a 3' sequence encoding a hexa His sequence (HHHHHH) fused directly to Asp 375. The amplified gene was subcloned into pFastBacMam (Viva Biotech).

Protein Expression. Recombinant baculovirus were generated according to Bac-to-Bac kit instructions (Life Technologies). Protein over-expression was accomplished by infecting exponentially growing HEK 293F cell culture at 1.3×10$^6$ cell/ml with virus (MOI=10) in the presence of 8 mM sodium butyrate. Infections were carried out at 37° C. for 48 hours, harvested by centrifugation, and stored at −80° C. for purification.

Protein Purification. Expressed full-length human Flag- and His-tagged PRMT6 protein was purified from cell paste by NiNTA agarose affinity chromatography after equilibration of the resin with buffer containing 50 mM Tris, 300 mM NaCl, 10% glycerol, pH 7.8 (Buffer Ni-A). Column was washed with 20 mM imidazole in the same buffer and Flag-PRMT6-His was eluted with 150 mM imidazole. Pooled fractions were dialysed against buffer Ni-A and further purified by anti-flag M2 affinity chromatography. Flag-PRMT6-His was eluted with 200 ug/ml FLAG peptide in the same buffer. Pooled fractions were dialysed in 20 mM Tris, 150 mM NaCl, 10% glycerol and 5 mM β-mercaptoethanol, pH 7.8. The purity of recovered protein was 95%.

Predicted Translations:

Flag-PRMT6-His
(SEQ ID NO.: 7)
MDYKDDDDKSQPKKRKLESGGGGEGGEGTEEEDGAEREAALERPRRTKR

ERDQLYYECYSDVSVHEEMIADRVRTDAYRLGILRNWAALRGKTVLDVG

AGTGILSIFCAQAGARRVYAVEASAIWQQAREVVRFNGLEDRVHVLPGP

VETVELPEQVDAIVSEWMGYGLLHESMLSSVLHARTKWLKEGGLLLPAS

AELFIAPISDQMLEWRLGFWSQVKQHYGVDMSCLEGFATRCLMGHSEIV

VQGLSGEDVLARPQRFAQLELSRAGLEQELEAGVGGRFRCSCYGSAPMH

GFAIWFQVTFPGGESEKPLVLSTSPFHPATHWKQALLYLNEPVQVEQDT

DVSGEITLLPSRDNPRRLRVLLRYKVGDQEEKTKDFAMEDHHHHHH

General Procedure for PRMT6 Enzyme Assays on Peptide Substrates. The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific).

DMSO (1 ul) was added to Columns 11, 12, 23, 24, rows A-H for the maximum signal control and 1 ul of SAH, a known product and inhibitor of PRMT6, was added to columns 11, 12, 23, 24, rows I-P for the minimum signal control. A cocktail (40 ul) containing the PRMT6 enzyme was added by Multidrop Combi (Thermo-Fisher). The compounds were allowed to incubate with PRMT6 for 30 min at room temperature, then a cocktail (10 ul) containing SAM and peptide was added to initiate the reaction (final volume=51 ul). The final concentrations of the components were as follows: PRMT6 was 1 nM, $^3$H-SAM was 200 nM, non-radiolabeled SAM was 250 nM, peptide was 75 nM, SAH in the minimum signal control wells was 1 mM, and the DMSO concentration was 2%. The assays were stopped by the addition of non-radiolabeled SAM (10 ul) to a final concentration of 400 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \; inh = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-Parameter IC50 Fit $$Y = \text{Bottom} + \frac{(\text{Top} - \text{Bottom})}{\left(1 + \left(\frac{X}{IC_{50}}\right)^{\text{Hill Coefficient}}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

PRMT8 Biochemical Assay

General Materials. S-adenosylmethionine (SAM), S-adenosylhomocysteine (SAH), bicine, Tween20, dimethylsulfoxide (DMSO), bovine skin gelatin (BSG), isopropyl-β-D-thiogalactopyranoside (IPTG), and Tris(2-carboxyethyl) phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates. Peptide representative of human histone H4 residues 31-45 was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-KPAIRRLARRG-GVKR-amide (SEQ ID NO.:8).

Molecular Biology: Full-length human PRMT8 (NM_019854.4) isoform 1 transcript clone was amplified from an HEK 293 cDNA library and subcloned into pGEX-4T-1 (GE Life Sciences). The resulting construct encodes an N-terminal GST tag and a thrombin cleavage sequence (MSPILGYWKIKGLVQPTRLLLEYLEEKY-EEHLYERDEGDKWRNKKFELGLEFPNLPYYI DGD-VKLTQSMAIIRYIADKHNMLGGCPKER-AEISMLEGAVLDIRYGVSRIAYSKDFETLK VDFLSKLPEMLKMFEDRLCHKTYLNGDH-VTHPDFMLYDALDVVLYMDPMCLDAFPKL VCFKKRIEAIPQIDKYLKSSKYIAW-PLQGWQATFGGGDHPPKSDLVPRGSPEF) (SEQ ID NO.:9) fused directly to Met 1 of PRMT8.

Protein Expression. *E. coli* (BL21(DE3) Gold, Stratagene) made competent by the CaCl$_2$ method were transformed with the PRMT8 construct and ampicillin selection. Protein overexpression was accomplished by growing the PRMT8 expressing *E. coli* clone and inducing expression with 0.3 mM IPTG at 16° C. The culture was grown for 12 hours, harvested by centrifugation, and stored at −80° C. for purification.

Protein Purification. Expressed full-length human GST-tagged PRMT8 protein was purified from cell paste by glutathione sepharose affinity chromatography after the resin was equilibrated with 50 mM phosphate buffer, 200 mM NaCl, 5% glycerol, 5 mM O-mercaptoethanol, pH7.8 (Buffer A). GST-tagged PRMT8 was eluted with 50 mM Tris, 2 mM glutathione, pH 7.8. Pooled fractions were cleaved by thrombin (10 U) and dialysed in buffer A. GST was removed by reloading the cleaved protein sample onto glutathione sepharose column and PRMT8 was collected in the flow-through fractions. PRMT8 was purified further by ceramic hydroxyapatite chromatography. The column was washed with 50 mM phosphate buffer, 100 mM NaCl, 5% glycerol, 5 mM β-mercaptoethanol, pH 7.8 and PRMT8 was eluted by 100 mM phosphate in the same buffer. Protein was concentrated and buffer was exchanged to 50 mM Tris, 300 mM NaCl, 10% glycerol, 5 mM β-mercaptoethanol, pH 7.8 by ultrafiltration. The purity of recovered protein was 89%.

Predicted Translations:

```
GST-tagged PRMT8
                                      (SEQ ID NO.: 10)
MSPILGYWKIKGLVQPTRLLLEYLEEKYEEHLYERDEGDKWRNKKFELG

LEFPNLPYYIDGDVKLTQSMAIIRYIADKHNMLGGCPKERAEISMLEGA

VLDIRYGVSRIAYSKDFETLKVDFLSKLPEMLKMFEDRLCHKTYLNGDH

VTHPDFMLYDALDVVLYMDPMCLDAFPKLVCFKKRIEAIPQIDKYLKSS

KYIAWPLQGWQATFGGGDHPPKSDLVPRGSPEFMGMKHSSRCLLLRRKM

AENAAESTEVNSPPSQPPQPVVPAKPVQCVHHVSTQPSCPGRGKMSKLL

NPEEMTSRDYYFDSYAHFGIHEEMLKDEVRTLTYRNSMYHNKHVFKDKV

VLDVGSGTGILSMFAAKAGAKKVFGIECSSISDYSEKIIKANHLDNIIT

IFKGKVEEVELPVEKVDIIISEWMGYCLFYESMLNTVIFARDKWLKPGG

LMFPDRAALYVVAIEDRQYKDFKIHWWENVYGFDMTCIRDVAMKEPLVD

IVDPKQVVTNACLIKEVDIYTVKTEELSFTSAFCLQIQRNDYVHALVTY

FNIEFTKCHKKMGFSTAPDAPYTHWKQTVFYLEDYLTVRRGEEIYGTIS

MKPNAKNVRDLDFTVDLDFKGQLCETSVSNDYKMR
```

General Procedure for PRMT8 Enzyme Assays on Peptide Substrates. The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of PRMT8, was added to columns 11, 12, 23, 24, rows I-P for the minimum signal control. A cocktail (40 ul) containing the PRMT8 enzyme was added by Multidrop Combi (Thermo-Fisher). The compounds were allowed to incubate with PRMT8 for 30 min at room temperature, then a cocktail (10 ul) containing $^3$H-SAM and peptide was added to initiate the reaction (final volume=51 ul). The final concentrations of the components were as follows: PRMT8 was 1.5 nM, $^3$H-SAM was 50 nM, non-radiolabeled SAM was 550 nM, peptide was 150 nM, SAH in the minimum signal control wells was 1 mM, and the DMSO concentration was 2%. The assays were stopped by the addition of non-radiolabeled SAM (10 ul) to a final concentration of 400 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).
% Inhibition Calculation $$\% \ inh = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.
Four-Parameter IC50 Fit $$Y = Bottom + \frac{(Top - Bottom)}{\left(1 + \left(\frac{X}{IC_{50}}\right)^{Hill \ Coefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.
PRMT3 Biochemical Assay
General Materials. S-adenosylmethionine (SAM), S-adenosylhomocysteine (SAH), bicine, Tween20, dimethylsulfoxide (DMSO), bovine skin gelatin (BSG), ), isopropyl-β-D-thiogalactopyranoside (IPTG), and Tris(2-carboxyethyl) phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates. Peptide containing the classic RMT substrate motif was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-GGRGGFGGRGGFG-GRGGFG-amide (SEQ ID NO.: 11).

Molecular Biology: Full-length human PRMT3 (NM_005788.3) isoform 1 transcript clone was amplified from an HEK 293 cDNA library and subcloned into pGEX-KG (GE Life Sciences). The resulting construct encodes an N-terminal GST tag and a thrombin cleavage sequence (MSPILGYWKIKGLVQPTRLLLEYLEEKY-EEHLYERDEGDKWRNKKFELGLEFPNLPYYI DGD-VKLTQSMAIIRYIADKHNMLGGCPKER-AEISMLEGAVLDIRYGVSRIAYSKDFETLK VDFLSKLPEMLKMFEDRLCHKTYLNGDH-VTHPDFMLYDALDVVLYMDPMCLDAFPKL VCFKKRIEAIPQIDKYLKSSKYIAW-PLQGWQATFGGGDHPPKSDLVPRGS) (SEQ ID NO.: 12) fused directly to Cys 2 of PRMT3.

Protein Expression. E. coli (BL21(DE3) Gold, Stratagene) made competent by the CaCl$_2$ method were transformed with the PRMT3 construct and ampicillin selection. Protein overexpression was accomplished by growing the PRMT3 expressing E. coli clone and inducing expression with 0.3 mM IPTG at 16° C. The culture was grown for 12 hours, harvested by centrifugation, and stored at −80° C. for purification.

Protein Purification. Expressed full-length human GST-tagged PRMT3 protein was purified from cell paste by glutathione sepharose affinity chromatography after equilibration of the resin with 50 mM phosphate buffer, 200 mM NaCl, 5% glycerol, 1 mM EDTA, 5 mM A-mercaptoethanol, pH6.5 (Buffer A). GST-tagged PRMT3 was eluted with 50 mM Tris, 2 mM glutathione, pH 7.1 and 50 mM Tris, 20 mM glutathione, pH 7.1. Pooled fractions were dialysed in 20 mM Tris, 50 mM NaCl, 5% glycerol, 1 mM EDTA, 1 mM DTT, pH7.5 (Buffer B) and applied to a Q Sepharose Fast Flow column. GST-tagged PRMT3 was eluted by 500 mM NaCl in buffer B. Pooled fractions were dialyzed in 25 mM phosphate buffer, 100 mM NaCl, 5% glycerol, 2 mM DTI, pH 6.8 (Buffer C) and loaded on to a ceramic hydroxyapatite column. GST-tagged PRMT3 eluted with 25-400 mM phosphate in buffer C. Protein was concentrated and buffer was exchanged to 20 mM Tris, 150 mM NaCl, 5% glycerol, 5 mM β-mercaptoethanol, pH7.8 by ultrafiltration. The purity of recovered protein was 70%.

Predicted Translations:

```
GST-tagged PRMT3
                                         (SEQ ID NO.: 13)
MSPILGYWKIKGLVQPTRLLLEYLEEKYEEHLYERDEGDKWRNKKFELG

LEFPNLPYYIDGDVKLTQSMAIIRYIADKHNMLGGCPKERAEISMLEGA

VLDIRYGVSRIAYSKDFETLKVDFLSKLPEMLKMFEDRLCHKTYLNGDH

VTHPDFMLYDALDVVLYMDPMCLDAFPKLVCFKKRIEAIPQIDKYLKSS

KYIAWPLQGWQATFGGGDHPPKSDLVPRGSCSLASGATGGRGAVENEED

LPELSDSGDEAAWEDEDDADLPHGKQQTPCLFCNRLFTSAEETFSHCKS

EHQFNIDSMVHKHGLEFYGYIKLINFIRLKNPTVEYMNSIYNPVPWEKE

EYLKPVLEDDLLLQFDVEDLYEPVSVPFSYPNGLSENTSVVEKLKHMEA
```

-continued

RALSAEAALARAREDLQKMKQFAQDFVMHTDVRTCSSSTSVIADLQEDE

DGVYFSSYGHYGIHEEMLKDKIRTESYRDFIYQNPHIFKDKVVLDVGCG

TGILSMFAAKAGAKKVLGVDQSEILYQAMDIIRLNKLEDTITLIKGKIE

EVHLPVEKVDVIISEWMGYFLLFESMLDSVLYAKNKYLAKGGSVYPDIC

TISLVAVSDVNKHADRIAFWDDVYGFKMSCMKKAVIPEAVVEVLDPKTL

ISEPCGIKHIDCHTTSISDLEFSSDFTLKITRTSMCTAIAGYFDIYFEK

NCHNRVVFSTGPQSTKTHWKQTVFLLEKPFSVKAGEALKGKVTVHKNKK

DPRSLTVTLTLNNSTQTYGLQ

General Procedure for PRMT3 Enzyme Assays on Peptide Substrates. The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of PRMT3, was added to columns 11, 12, 23, 24, rows I-P for the minimum signal control. A cocktail (40 ul) containing the PRMT3 enzyme was added by Multidrop Combi (Thermo-Fisher). The compounds were allowed to incubate with PRMT3 for 30 min at room temperature, then a cocktail (10 ul) containing SAM and peptide was added to initiate the reaction (final volume=51 ul). The final concentrations of the components were as follows: PRMT3 was 0.5 nM, $^3$H-SAM was 100 nM, non-radiolabeled SAM was 1.8 uM, peptide was 330 nM, SAH in the minimum signal control wells was 1 mM, and the DMSO concentration was 2%. The assays were stopped by the addition of potassium chloride (10 ul) to a final concentration of 100 mM. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \ inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter IC50 Fit $$Y = Bottom + \frac{(Top - Bottom)}{\left(1 + \left(\frac{X}{IC_{50}}\right)^{Hill \ Coefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

CARM1 Biochemical Assay

General Materials. S-adenosylmethionine (SAM), S-adenosylhomocysteine (SAH), bicine, Tween20, dimethylsulfoxide (DMSO), bovine skin gelatin (BSG), sodium butyrate and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates. Peptide representative of human histone H3 residues 16-30 was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-PRKQLATKAARK-SAP-amide and contained a monomethylated arginine at position 26 (SEQ ID NO.: 14).

Molecular Biology: Human CARM1 (PRMT4) (NM_199141.1) transcript clone was amplified from an HEK 293 cDNA library, incorporating a flanking 5' sequence encoding a FLAG tag (MDYKDDDDK) (SEQ ID NO.:6) fused directly to Ala 2 of CARM1 and 3' sequence encoding a hexa His sequence (EGHHHHHH) (SEQ ID NO.:15) fused directly to Ser 608. The gene sequence encoding isoform1 containing a deletion of amino acids 539-561 was amplified subsequently and subcloned into pFastBacMam (Viva Biotech).

Protein Expression. Recombinant baculovirus were generated according to Bac-to-Bac kit instructions (Life Technologies). Protein over-expression was accomplished by infecting exponentially growing HEK 293F cell culture at 1.3×10$^6$ cell/ml with virus (MOI=10) in the presence of 8 mM sodium butyrate. Infections were carried out at 37° C. for 48 hours, harvested by centrifugation, and stored at –80° C. for purification.

Protein Purification. Expressed full-length human Flag- and His-tagged CARM1 protein was purified from cell paste by anti-flag M2 affinity chromatography with resin equilibrated with buffer containing 20 mM Tris, 150 mM NaCl, 5% glycerol, pH 7.8. Column was washed with 500 mM NaCl in buffer A and Flag-CARM1-His was eluted with 200 ug/ml FLAG peptide in buffer A. Pooled fractions were dialyzed in 20 mM Tris, 150 mM NaCl, 5% glycerol and 1 mM DTI, pH 7.8. The purity of recovered protein was 94.

Predicted Translations:

Flag-CARM1-His (SEQ ID NO.: 16)

MDYKDDDDKAAAAAAVGPGAGGAGSAVPGGAGPCATVSVFPGARLLTIG

DANGEIQRHAEQQALRLEVRAGPDSAGIALYSHEDVCVFKCSVSRETEC

SRVGKQSFIITLGCNSVLIQFATPNDFCSFYNILKTCRGHTLERSVFSE

RTEESSAVQYFQFYGYLSQQQNMMQDYVRTGTYQRAILQNHTDFKDKIV

LDVGCGSGILSFFAAQAGARKIYAVEASTMAQHAEVLVKSNNLTDRIVV

IPGKVEEVSLPEQVDIIISEPMGYMLFNERMLESYLHAKKYLKPSGNMF

PTIGDVHLAPFTDEQLYMEQFTKANFWYQPSFHGVDLSALRGAAVDEYF

RQPVVDTFDIRILMAKSVKYTVNFLEAKEGDLHRIEIPFKFHMLHSGLV

HGLAFWFDVAFIGSIMTVWLSTAPTEPLTHWYQVRCLFQSPLFAKAGDT

LSGTCLLIANKRQSYDISIVAQVDQTGSKSSNLLDLKNPFFRYTGTTPS

-continued

PPPGSHYTSPSENMWNTGSTYNLSSGMAVAGMPTAYDLSSVIASGSSVG

HNNLIPLGSSGAQGSGGGSTSAHYAVNSQFTMGGPAISMASPMSIPTNT

MHYGSEGHHHHHH

General Procedure for CARM1 Enzyme Assays on Peptide Substrates. The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of CARM1, was added to columns 11, 12, 23, 24, rows I-P for the minimum signal control. A cocktail (40 ul) containing the CARM1 enzyme was added by Multidrop Combi (Thermo-Fisher). The compounds were allowed to incubate with CARM1 for 30 min at room temperature, then a cocktail (10 ul) containing $^3$H-SAM and peptide was added to initiate the reaction (final volume=51 ul). The final concentrations of the components were as follows: CARM1 was 0.25 nM, $^3$H-SAM was 30 nM, peptide was 250 nM, SAH in the minimum signal control wells was 1 mM, and the DMSO concentration was 2%. The assays were stopped by the addition of non-radiolabeled SAM (10 ul) to a final concentration of 300 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \, inh = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-Parameter IC50 Fit $$Y = Bottom + \frac{(Top - Bottom)}{\left(1 + \left(\frac{X}{IC_{50}}\right)^{Hill \, Coefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

The biochemical evaluation of the exemplary compounds are shown in Table 2.

TABLE 2

| | Biochemical evaluation (μM) | | | | |
|---|---|---|---|---|---|
| Cmpd No. | PRMT1 | PRMT6 | PRMT8 | PRMT3 | PRMT4 |
| 1 | B | B | D | E | E |
| 2 | B | A | C | E | E |
| 3 | A | A | C | E | — |
| 4 | B | B | B | — | — |
| 5 | E | E | — | — | — |
| 6 | C | C | D | — | — |
| 7 | B | B | B | — | — |
| 8 | A | A | A | — | — |
| 9 | A | A | A | — | — |
| 10 | B | B | D | — | — |
| 11 | C | C | E | — | — |

For Table 2,
"A" indicates an $IC_{50} \leq 0.100$ μM,
"B" indicates an $IC_{50}$ of 0.101-1.00 μM,
"C" indicates an $IC_{50}$ of 1.01-3.00 μM,
"D" indicates an $IC_{50}$ of 3.01-10 μM, and
$IC_{50} \geq 10.01$ μM.
"—" indicates no data provided.

RKO Methylation Assay

RKO adherent cells were purchased from ATCC (American Type Culture Collection), Manassas, Va., USA. DMEM/Glutamax medium, penicillin-streptomycin, heat inactivated fetal bovine serum, 0.05% trypsin and D-PBS were purchased from Life Technologies, Grand Island, N.Y., USA. Odyssey blocking buffer, 800CW goat anti-rabbit IgG (H+L) antibody, and Licor Odyssey infrared scanner were purchased from Licor Biosciences, Lincoln, Nebr., USA. Mono-methyl arginine antibody was purchased from Cell Signaling Technology, Danvers, Mass., USA. Methanol was purchased from VWR, Franklin, Mass., USA. 10% Tween 20 was purchased from KPL, Inc., Gaithersburg, Md., USA. DRAQ5 was purchased from Biostatus Limited, Leicestershire, UK.

RKO adherent cells were maintained in growth medium (DMEM/Glutamax medium supplemented with 10% v/v heat inactivated fetal bovine serum and 100 units/mL penicillin-streptomycin) and cultured at 37° C. under 5% $CO_2$.

Cell treatment, In Cell Western (ICW) for detection of mono-methyl arginine and DNA content. RKO cells were seeded in assay medium at a concentration of 20,000 cells per mL to a poly-D-lysine coated 384 well culture plate (BD Biosciences 356697) with 50 μL per well. Compound (100 nL) from a 96-well source plate was added directly to 384 well cell plate. Plates were incubated at 37° C., 5% $CO_2$ for 72 hours. After three days of incubation, plates were brought to room temperature outside of the incubator for ten minutes and blotted on paper towels to remove cell media. 50 μL of ice cold 100% methanol was added directly to each well and incubated for 30 min at room temperature. After 30 min, plates were transferred to a Biotek EL406 plate washer and washed 2 times with 100 μL per well of wash buffer (1×PBS). Next 60 μL per well of Odyssey blocking buffer (Odyssey Buffer with 0.1% Tween 20 (v/v)) were added to each plate and incubated 1 hour at room temperature. Blocking buffer was removed and 20 μL per well of primary antibody was added (mono-methyl arginine diluted 1:200 in Odyssey buffer with 0.1% Tween 20 (v/v)) and plates were incubated overnight (16 hours) at 4° C. Plates were washed 5 times with 100 μL per well of wash buffer. Next 20 μL per well of secondary antibody was added (1:200 800CW goat anti-rabbit IgG (H+L) antibody, 1:1000 DRAQ5 (Biostatus limited) in Odyssey buffer with 0.1% Tween 20 (v/v)) and incubated for 1 hour at room temperature. The plates were washed 5 times with 100 μL per well wash buffer then 2 times with 100 μL per well of water. Plates were allowed to dry at room temperature then imaged on the Licor Odyssey machine which measures integrated intensity at 700 nm and 800 nm wavelengths. Both 700 and 800 channels were scanned.

Calculations: First, the ratio for each well was determined by:

$$\left(\frac{\text{Monomethyl Arginine 800nm value}}{DRAQ5\ 700\text{nm value}}\right)$$

Each plate included fourteen control wells of DMSO only treatment (minimum activation) as well as fourteen control wells for maximum activation treated with 20 μM of a reference compound. The average of the ratio values for each control type was calculated and used to determine the percent activation for each test well in the plate. Reference compound was serially diluted three-fold in DMSO for a total of nine test concentrations, beginning at 20 μM. Percent activation was determined and $EC_{30}$ curves were generated using triplicate wells per concentration of compound.

Percent Activation =

$$100 - \left(\left(\frac{\text{(Individual Test Sample Ratio)} - \text{(Minimum Activation Ratio)}}{\text{(Maximum Activation Ratio)} - \text{(Minimum Activation Ratio)}}\right) * 100\right)$$

TABLE 3

| In Cell Western | |
| --- | --- |
| Cmpd No. | $EC_{30}$ |
| 1 | C |
| 2 | C |
| 3 | C |
| 4 | A |
| 5 | C |
| 6 | C |
| 7 | C |
| 8 | A |
| 9 | A |
| 10 | C |
| 11 | C |

Table 3,
"A" indicates an $EC_{30} \leq 3.00$ μM,
"B" indicates an $EC_{30}$ of 3.01-12.00 μM, and
"C" indicates an $EC_{30} \geq 12.01$ μM.

Other Embodiments

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A compound of Formula (II):

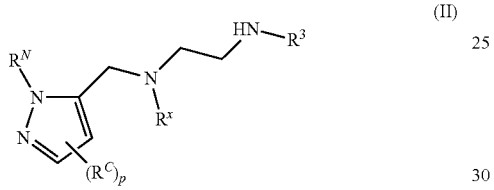

(II)

or a pharmaceutically acceptable salt thereof,
wherein:

$R^N$ is optionally substituted aryl or optionally substituted heteroaryl;

each instance of $R^C$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, —$OR^A$, —$N(R^B)_2$, —$SR^A$, —$C(=O)R^A$, —$C(=O)OR^A$, —$C(=O)SR^A$, —$C(=O)N(R^B)_2$, —$C(=O)N(R^B)N(R^B)_2$, —$OC(=O)R^A$, —$OC(=O)N(R^B)_2$, —$NR^BC(=O)R^A$, —$NR^BC(=O)N(R^B)_2$, —$NR^BC(=O)N(R^B)N(R^B)_2$, —$NR^BC(=O)OR^A$, —$SC(=O)R^A$, —$C(=NR^B)R^A$, —$C(=NNR^B)R^A$, —$C(=NOR^A)R^A$, —$C(=NR^B)N(R^B)_2$, —$NR^BC(=NR^B)R^B$, —$C(=S)R^A$, $C(=S)N(R^B)_2$, —$NR^BC(=S)R^A$, —$S(=O)R^A$, —$OS(=O)_2R^A$, —$SO_2R^A$, —$NR^BSO_2R^A$, and —$SO_2N(R^B)_2$;

each instance of $R^A$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, an oxygen protecting group when attached to an oxygen atom, and a sulfer protecting group when attached to a sulfur atom;

each instance of $R^B$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted alkyl-Cy, and a nitrogen protecting group, or two $R^B$ groups are taken together with their intervening atoms to form an optionally substituted heterocyclic ring;

each instance of Cy is independently optionally substituted $C_{3-7}$ cycloalkyl, optionally substituted 4- to 7-membered heterocyclyl, optionally substituted aryl, or optionally substituted heteroaryl;

$R^3$ is hydrogen, $C_{1-4}$ alkyl, or $C_{3-4}$ carbocyclyl;

$R^x$ is optionally substituted $C_{1-4}$ alkyl, or optionally substituted $C_{3-4}$ carbocyclyl; and p is 0, 1, or 2.

2. The compound of claim 1, wherein $R^x$ is methyl, ethyl, isopropyl, propyl, butyl, hydroxyethyl, methoxyethyl, cyclopropyl, or cyclobutyl.

3. The compound of claim 1, wherein $R^3$ is hydrogen, methyl, ethyl, propyl, butyl, cyclopropyl, or cyclobutyl.

4. The compound of claim 1, wherein the compound is selected from the group consisting of:

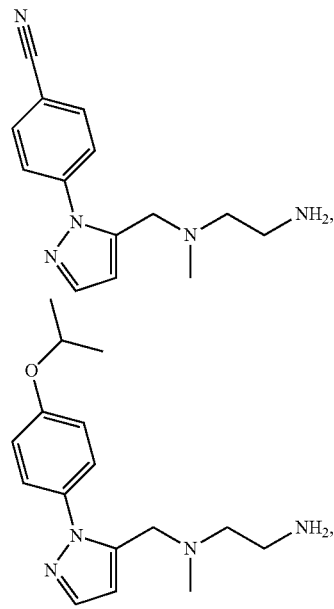

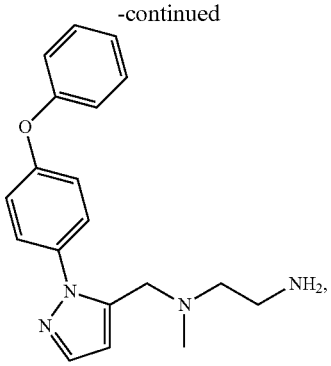

and pharmaceutically acceptable salts thereof.

5. A pharmaceutical composition comprising a compound of claim 1, or a pharmaceutically acceptable salt thereof, and optionally a pharmaceutically acceptable excipient.

6. A kit or packaged pharmaceutical comprising a compound of claim 1 or a pharmaceutically acceptable salt thereof, and instructions for use thereof.

7. A method of inhibiting an arginine methyl transferase (RMT) comprising contacting a cell with an effective amount of a compound of claim 1 or a pharmaceutically acceptable salt thereof.

8. The method of claim 7, wherein the arginine methyl transferase is PRMT1, PRMT3, PRMT6, PRMT8, or CARM1.

9. The method of claim 8, wherein the arginine methyl transferase is PRMT1.

10. A method of modulating gene expression comprising contacting a cell with an effective amount of a compound of claim 1 or a pharmaceutically acceptable salt thereof.

11. A method of modulating transcription comprising contacting a cell with an effective amount of a compound of claim 1 or a pharmaceutically acceptable salt thereof.

12. A method of treating an RMT-mediated disorder, comprising administering to a subject in need thereof a therapeutically effective amount of a compound of claim 1, or a pharmaceutically acceptable salt thereof.

13. The method of claim 12, wherein the RMT-mediated disorder is a PRMT1-mediated disorder, a PRMT3-mediated disorder, a PRMT6-mediated disorder, a PRMT8-mediated disorder, or a CARM1-mediated disorder.

14. The method of claim 13, wherein the RMT-mediated disorder is a PRMT1-mediated disorder.

15. The method of claim 12, wherein the disorder is a proliferative disorder, a neurological disorder, a muscular dystrophy, an autoimmune disorder, a vascular disorder, or a metabolic disorder.

16. The method of claim 15, wherein the proliferative disorder is cancer.

17. The method of claim 15, wherein the neurological disorder is amyotrophic lateral sclerosis.

18. The compound of claim 1, wherein $R^x$ is $CH_3$.

19. The compound of claim 1, wherein $R^3$ is hydrogen.

20. The compound of claim 1, wherein $R^N$ is optionally substituted aryl.

21. The compound of claim 1, wherein $R^N$ is independently of Formula (i):

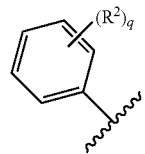

(i)

wherein:

each instance of $R^2$ is independently selected from the group consisting of hydrogen, halogen, $-N_3$, $-CN$, $-NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, optionally substituted alkyl-Cy, $-OR^A$, $-N(R^B)_2$, $-SR^A$, $-C(=O)OR^A$, $-C(=O)SR^A$, $-C(=O)N(R^B)_2$, $-C(=O)N(R^B)N(R^B)_2$, $-OC(=O)R^A$, $-OC(=O)N(R^B)_2$, $-NR^BC(=O)R^A$, $-NR^BC(=O)N(R^B)_2$, $-NR^BC(=O)N(R^B)N(R^B)_2$, $-NR^BC(=O)OR^A$, $-SC(=O)R^A$, $-C(=NR^B)R^A$, $-C(=NNR^B)R^A$, $-C(=NOR^A)R^A$, $-C(=NR^B)N(R^B)_2$, $-NR^BC(=NR^B)R^B$, $-C(=S)R^A$, $-(=S)N(R^B)_2$, $-NR^BC(=S)R^A$, $-S(=O)R^A$, $-OS(=O)_2R^A$, $-SO_2R^A$, $-NR^BSO_2R^A$, and $-SO_2N(R^B)_2$; and q is 0, 1, 2, 3, 4, or 5 as valence permits.

22. The compound of claim 21, wherein q is 1.

23. The compound of claim 21, wherein Formula (i) is of formula:

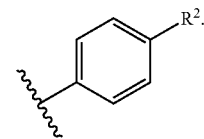

24. The compound of claim 21, wherein $R^N$ is selected from the group consisting of:

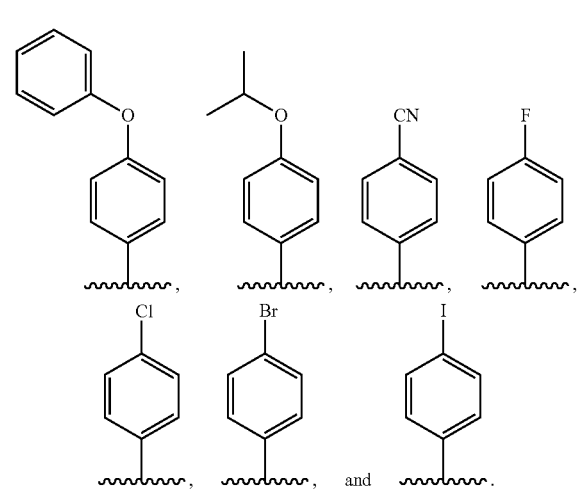

25. The compound of claim 1, wherein the compound is of Formula (II-a):

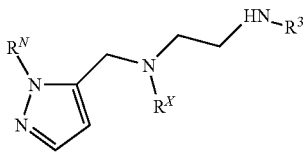

(II-a)

or a pharmaceutically acceptable salt thereof.

26. The compound of claim 25, wherein $R^X$ is methyl, ethyl, isopropyl, propyl, butyl, hydroxyethyl, methoxyethyl, cyclopropyl, or cyclobutyl.

27. The compound of claim 25, wherein $R^3$ is hydrogen, methyl, ethyl, propyl, butyl, cyclopropyl, or cyclobutyl.

28. The compound of claim 25, wherein $R^N$ is optionally substituted aryl.

29. The compound of claim 28, wherein $R^N$ is independently of Formula (i):

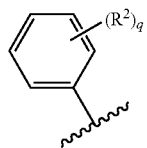

(i)

wherein:
each instance of $R^2$ is independently selected from the group consisting of hydrogen, halogen, $-N_3$, $-CN$, $-NO_2$, $C_{1-4}$ alkynyl, $C_{3-6}$ carbocyclyl, phenyl, 4- to 6-membered heterocyclyl, 5- to 6-membered heteroaryl, $C_{1-4}$ alkyl-Cy, $-OR^A$, $-N(R^B)_2$, $-SR^A$, $-C(=O)R^A$, $-C(=O)OR^A$, $-C(=O)N(R^B)_2$, $-OC(=O)R^A$, $-OC(=O)N(R^B)_2$, $-NR^BC(=O)R^A$, $-NR^BC(=O)N(R^B)_2$, $-NR^BC(=O)OR^A$, $-SO_2R^A$, $-NR^BSO_2R^A$, and $-SO_2N(R^B)_2$;

each instance of $R^A$ is independently selected from the group consisting of hydrogen, $C_{1-4}$ alkyl, $C_{3-6}$ carbocyclyl, 4- to 6-membered heterocyclyl, phenyl, and 5- to 6-membered heteroaryl;

each instance of $R^B$ is independently selected from the group consisting of hydrogen, $C_{1-4}$ alkyl, $C_{3-6}$ carbocyclyl, 4- to 6-membered heterocyclyl, phenyl, and 5- to 6-membered heteroaryl, or two $R^B$ groups are taken together with their intervening atoms to form a 4- to 6-membered heterocyclic ring;

each instance of Cy is independently $C^{3-6}$ cycloalkyl, 4- to 6-membered heterocyclyl, phenyl, or 5- to 6-membered heteroaryl; and q is 0, 1, 2, or 3 as valence permits.

30. The compound of claim 1, wherein:
each instance of $R^C$ is independently selected from the group consisting of hydrogen, $C_{1-4}$ alkyl, $C_{2-4}$ alkenyl, $C_{2-4}$ alkynyl, $C_{3-6}$ carbocyclyl, 4- to 6-membered heterocyclyl, phenyl, 5- to 6-membered heteroaryl, $C_{1-4}$ alkyl-Cy, $-OR^A$, $-N(R^B)_2$, and $-C(=O)R^A$;

each instance of $R^A$ is independently selected from the group consisting of hydrogen and $C_{1-4}$ alkyl;

each instance of $R^B$ is independently selected from the group consisting of hydrogen and $C_{1-4}$ alkyl, or two $R^B$ groups are taken together with their intervening atoms to form a 4- to 6-membered heterocyclic ring; and each instance of Cy is independently $C_{3-6}$ cycalkyl, 4- to 6-membered heterocyclyl, phenyl, or 5- to 6-membered heteroaryl.

31. A pharmaceutical composition comprising a compound of claim 4, or a pharmaceutically acceptable salt thereof, and optionally a pharmaceutically acceptable excipient.

32. The method of claim 16, wherein the cancer is breast cancer, prostate cancer, lung cancer, colon cancer, bladder cancer, or leukemia.

33. The method of claim 15, wherein the disorder is an autoimmune disorder, and the autoimmune disorder is rheumatoid arthritis.

* * * * *